(12) United States Patent
Martinant et al.

(10) Patent No.: US 11,445,671 B2
(45) Date of Patent: Sep. 20, 2022

(54) POLYNUCLEOTIDE RESPONSIBLE OF HAPLOID INDUCTION IN MAIZE PLANTS AND RELATED PROCESSES

(71) Applicants: INSTITUT NATIONAL DE LA RECHERCHE AGRONOMIQUE (INRA), Paris (FR); LIMAGRAIN EUROPE, Saint-Beauzire (FR); Centre national de la recherche scientifique, Paris (FR)

(72) Inventors: Jean-Pierre Martinant, Vertaizon (FR); Jordi Comadran, Riom (FR); Jean-Baptiste Laffaire, Mozac (FR); Peter Rogowsky, Lyons (FR); Thomas Widiez, Lyons (FR)

(73) Assignees: INSTITUT NATIONAL DE LA RECHERCHE AGRONOMIQUE (INRA), Paris (FR); LIMAGRAIN EUROPE, Saint-Beauzire (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 90 days.

(21) Appl. No.: 15/572,110

(22) PCT Filed: May 6, 2016

(86) PCT No.: PCT/EP2016/060202
§ 371 (c)(1),
(2) Date: Nov. 6, 2017

(87) PCT Pub. No.: WO2016/177887
PCT Pub. Date: Nov. 10, 2016

(65) Prior Publication Data
US 2018/0116142 A1      May 3, 2018

(30) Foreign Application Priority Data

May 7, 2015   (EP) .................................... 15305699

(51) Int. Cl.
| | | |
|---|---|---|
| *A01H 1/08* | (2006.01) | |
| *A01H 1/04* | (2006.01) | |
| *C07K 14/415* | (2006.01) | |
| *C12Q 1/6895* | (2018.01) | |
| *C12N 15/82* | (2006.01) | |

(52) U.S. Cl.
CPC ................ *A01H 1/08* (2013.01); *A01H 1/04* (2013.01); *C07K 14/415* (2013.01); *C12N 15/8218* (2013.01); *C12N 15/8287* (2013.01); *C12Q 1/6895* (2013.01); *C12Q 2600/13* (2013.01); *C12Q 2600/156* (2013.01)

(58) Field of Classification Search
CPC .................... A01H 1/08; A01H 1/04
See application file for complete search history.

(56) References Cited

U.S. PATENT DOCUMENTS

| | | | |
|---|---|---|---|
| 9,677,082 B2* | 6/2017 | Chintamanani | .... C12N 15/8287 |
| 10,631,482 B2 | 4/2020 | Bolduan et al. | |
| 2010/0209506 A1 | 8/2010 | Eisenreich | |
| 2012/0017292 A1 | 1/2012 | Kovalic et al. | |
| 2016/0017349 A1 | 1/2016 | Ayele et al. | |
| 2017/0240912 A1 | 8/2017 | Chintamanani et al. | |
| 2017/0327832 A1 | 11/2017 | Bolduan et al. | |
| 2018/0104249 A1 | 4/2018 | Eisenreich | |
| 2020/0229367 A1 | 7/2020 | Bouldan et al. | |

FOREIGN PATENT DOCUMENTS

| | | |
|---|---|---|
| CN | 104846104 | 8/2015 |
| WO | WO-2016/075255 | 5/2016 |

OTHER PUBLICATIONS

Dong et al., Fine mapping of qhir1 influencing in vivo haploid induction in maize. Theoretical and Applied Genetics, 126(7): 1713-1720, 2013.*
Barret et al., A major locus expressed in the male gametophyte with incomplete penetrance is responsible for in situ gynogenesis in maize, Theoretical and Applied Genetics, 117(4): 581-594, 2008.*
Xu et al., Gametophytic and zygotic selection leads to segregation distortion through in vivo induction of a maternal haploid in maize. Journal of Experimental Botany, 64(4): 1083-1096, 2013.*
Barret P et al: "A major locus expressed in the male gametophyte with incomplete penetrance is responsible for in situ gynogenesis in maize", Theoretical and Applied Genetics; International Journal of Plant Breeding Research, Springer, Berlin, DE, vol. 117, No. 4, May 31, 2008 (May 31, 2008), pp. 581-594, XP019618403, ISSN: 1432-2242 the whole document.
Andrea Gallavotte et al: "Positional Cloning in Maize ( *Zea mays* subsp. mays, Poaceae)", Applications in Plant Sciences, vol. 3, No. 1, Jan. 1, 2015 (Jan. 1, 2015), p. 1400092, XP055218553, DOI: 10.3732/apps.1400092 the whole document.
Dong X et al: "Fine mapping ofqhir1influencing in vivo haploid induction in maize", Theoretical and Applied Genetics, Springer, Berlin, DE, vol. 126, No. 7, Mar. 29, 2013 (Mar. 29, 2013), pp. 1713-1720, XP035333157, ISSN: 0040-5752, DOI: 10.1007/S00122-013-2086-9 [retrieved on Mar. 29, 2013].
Bortiri E et al: "Advances in maize genomics: the emergence of positional cloning", Current Opinion in Plant Biology, Quadrant Subscription Services, GB, vol. 9, No. 2, Apr. 1, 2006 (Apr. 1, 2006), pp. 164-171, XP028014917, ISSN: 1369-5266, DOI: 10.1016/J.PBI.2006.01.006 [retrieved on Apr. 1, 2006].

(Continued)

*Primary Examiner* — Russell Kallis
(74) *Attorney, Agent, or Firm* — B. Aaron Schulman, Esq.

(57) ABSTRACT

The present invention concerns an isolated polynucleotide responsible of haploid induction in maize plants and related processes. Additionally, the invention relates to plants that have been genetically transformed with the polynucleotide of the invention. The invention also relates to a process for screening a mutant plant population for enhanced haploid induction by using said isolated polynucleotide. The invention further relates to molecular markers associated with haploid induction in maize plants and their use in quality control for inducer lines.

4 Claims, 14 Drawing Sheets

Figure 1:
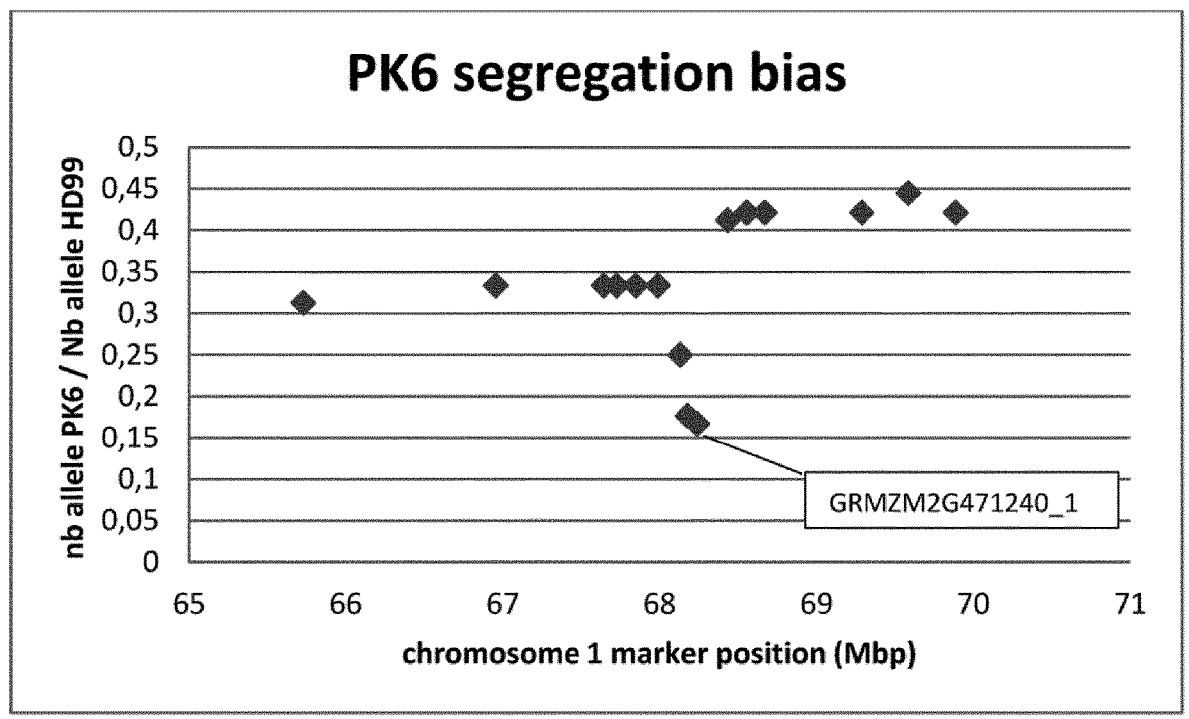

Specification includes a Sequence Listing.

(56) References Cited

OTHER PUBLICATIONS

Andrea Gallavotti et al: "sparse inflorescencel encodes a monocot-specific Yucca-like gene required for vegetative and reproductive development in maize", Proceedings of the National Academy of Sciences, vol. 105. No. 39, Jan. 1, 2008 (Jan. 1, 2008), XP055218572, US ISSN: 0027-8424.
International Search Report for PCT/EP2016/060202, dated Aug. 8, 2016.
Written Opinion for the International Searching Authority for PCT/EP2016/060202, dated Aug. 8, 2016.
Dong, et al, "Fine mapping of qhir1 influencing in vivo haploid induction in maize", 2013, vol. 126, pp. 1713-1720, Theor Appl Genet.
Coe, "A Line of Maize With High Haploid Frequency", vol. XCIII, No. 873, 1959, pp. 381-382, The American Naturalist.
Bordes, Jacques, Création de lignées haplöides doubles de maïs par gynogenèse induite in situ: amélioration de la méthode et intégration dans les schémas de selection. Biologie végetale. Université Blaise Pascal-Clermont-Ferrand II, 2006.
Geiger, et al., "Doubled Haploids in Hybrid Maize Breeding", 2009, pp. 485-499, vol. 54, Maydica.
Barret, et al, "A major locus expressed in the male gametophyte with incomplete penetrance is responsible for in situ gynogenesis in maize", 2008, pp. 581-594, vol. 117, Theor Appl Genet.
Röber, et al., "In Vivo Haploid Induction in Maize-Performance of New Inducers and Significance of Doubled Haploid Lines in Hybrid Breeding", 2005, pp. 275-283, vol. 50, Maydica.
Deimling, et al., Methodik und Genetik der in-vivo-Haploideninduktion bei Mais, 1997, pp. 203-224, vol. 38, Vortr. Pflanzenzüchtg.
Jackson, David, "No sex please, we're (in)breeding", 2017, pp. 703-704, vol. 36, No. 6, The EMBO Journal.
Gilles, et al., "Loss of pollen-specific phospholipase Not Like Dad triggers gynogenesis in maize", Feb. 22, 2017, The EMBO Journal.
Lashermes, et al., "Genetic control of maternal haploidy in maize (*Zea mays* L.) and selection of haploid inducing lines", 1988, pp. 405-410, vol. 76, No. 3, Theor Appl Genet.
Kelliher, et al., "Matrilineal, a sperm-specific phospholipase, triggers maize haploid induction", 2017, pp. 1-18, Nature.
Gilles, et al., "Haploid induction in plants", Oct. 23, 2017, pp. R1089-R1107, vol. 27, Current Biology.
Hu, et al., "The Genetic Basis of Haploid Induction in Maize Identified with a Novel Genome-Wide Association Method", Apr. 2016, pp. 1267-1276, vol. 202, Genetics.
Ren, et al., "Novel technologies in doubled haploid line development", 2017, pp. 1-10, Plant Biotechnology Journal.
Li, et al., "Single nucleus sequencing reveals spermatid chromosome fragmentation as a possible cause of maize haploid induction", 2017, pp. 1-9, vol. 8, No. 991, Nature Communications.
Weber, et al., "Today's Use of Haploids in Corn Plant Breeding", 2014, pp. 1-22, vol. 123, Advances in Agronomy.
Liu, et al., "New insight into the mechanism of heterofertilization during maize haploid induction", Jul. 13, 2017, vol. 213, pp. 1-11.
Xu, et al., "Gametophytic and zygotic selection leads to segregation distortion through in vivo induction of a maternal haploid in maize", 2013, pp. 1083-1096, vol. 64, No. 4, Journal of Experimental Botany.
Lui, et al., "A 4-bp Insertion at ZmPLA1 Encoding a Putative Phospholipase A Generates Haploid Induction in Maize", Mar. 2017, pp. 520-522, vol. 10, Molecular Plant.
Nair, et al., "Dissection of a major QTL qhir1 conferring maternal haploid induction ability in maize", Mar. 18, 2017, pp. 1-10, Theor Appl Genet.
Prigge, et al., "New Insights into the Genetics of in Vivo Induction of Maternal Haploids, the Backbone of Doubled Haploid Technology in Maize", Feb. 2012, pp. 781-793, vol. 190, Genetics.
Prigge, et al, "Doubled Haploids in Tropical Maize: I. Effects of Inducers and Source Germplasm on in vivo Haploid Induction Rates", Jul.-Aug. 2011, pp. 1498-1506, vol. 51, Crop Science.

\* cited by examiner

|  |  | 1 | 50 |
|---|---|---|---|
| GRMZM2G471240_B73_ACB | (1) | AGTTCATCACTAATCACACTTATTGTGCCCTCGACGAGTATCTATAGCTA | |
| GRMZM2G471240_HD99_ACB | (1) | -------------------------------------------------- | |
| GRMZM2G471240_PK6_ACD | (1) | -------------------------------------------------- | |
|  |  | 51 | 100 |
| GRMZM2G471240_B73_ACB | (51) | GCTCATTAATCGATTCGGGGGTGTGTTGTCGAAGGCGGCAATGGCGAGCT | |
| GRMZM2G471240_HD99_ACB | (1) | ---------------------------GTCGAAGGCGGCAATGGCGAGCT | |
| GRMZM2G471240_PK6_ACD | (1) | ---------------GGGGTGTGCGGTCGAAGGCGGCAATGGCGAGCT | |
|  |  | 101 | 150 |
| GRMZM2G471240_B73_ACB | (101) | ACTCGTCGCGGCGTCCATGCAATACCTGTAGCACGAAGGCGATGGCCGGG | |
| GRMZM2G471240_HD99_ACB | (24) | ACTCGTCGCGGCGTCCATGCAATACCTGTAGCACGAAGGCGATGGCCGGG | |
| GRMZM2G471240_PK6_ACD | (34) | ACTCGTCGCGGCGTCCATGCAATACCTGTAGCACGAAGGCGATGGCCGGG | |
|  |  | 151 | 200 |
| GRMZM2G471240_B73_ACB | (151) | AGCGTGGTCGGCGAGCCCGTCGTGCTGGGGCAGAGGGTGACGGTGCTGAC | |
| GRMZM2G471240_HD99_ACB | (74) | AGCGTGGTCGGCGAGCCCGTCGTGCTGGGGCAGAGGGTGACGGTGCTGAC | |
| GRMZM2G471240_PK6_ACD | (84) | AGCGTGGTCGGCGAGCCCGTCGTGCTGGGGCAGAGGGTGACGGTGCTGAC | |
|  |  | 201 | 250 |
| GRMZM2G471240_B73_ACB | (201) | GGTGGACGGCGGCGGCGTCCGGGGTCTCATCCCGGGAACCATCCTCGCCT | |
| GRMZM2G471240_HD99_ACB | (124) | GGTGGACGGCGGCGGCGTCCGGGGTCTCATCCCGGGAACCATCCTCGCCT | |
| GRMZM2G471240_PK6_ACD | (134) | GGTGGACGGCGGCGGCGTCCGGGGTCTCATCCCGGGAACCATCCTCGCCT | |
|  |  | 251 | 300 |
| GRMZM2G471240_B73_ACB | (251) | TCCTGGAGGCCAGGCTGCAGGAGCTGGACGGACCGGAGGCGAGGCTGGCG | |
| GRMZM2G471240_HD99_ACB | (174) | TCCTGGAGGCCAGGCTGCAGGAGCTGGACGGACCGGAGGCGAGGCTGGCG | |
| GRMZM2G471240_PK6_ACD | (184) | TCCTGGAGGCCAGGCTGCAGGAGCTGGACGGACCGGAGGCGAGGCTGGCG | |
|  |  | 301 | 350 |
| GRMZM2G471240_B73_ACB | (301) | GACTACTTCGACTACATCGCCGGAACCAGCACCGGCGGTCTCATCACCGC | |
| GRMZM2G471240_HD99_ACB | (224) | GACTACTTCGACTACATCGCCGGAACCAGCACCGGCGGTCTCATCACCGC | |
| GRMZM2G471240_PK6_ACD | (234) | GACTACTTCGACTACATCGCCGGAACCAGCACCGGCGGTCTCATCACCGC | |
|  |  | 351 | 400 |
| GRMZM2G471240_B73_ACB | (351) | CATGCTCACCGCGCCCGGCAAGGACAAGCGGCCTCTCTACGCTGCCAAGG | |
| GRMZM2G471240_HD99_ACB | (274) | CATGCTCACCGCGCCCGGCAAGGACAAGCGGCCTCTCTACGCTGCCAAGG | |
| GRMZM2G471240_PK6_ACD | (284) | CATGCTCACCGCGCCCGGCAAGGACAAGCGGCCTCTCTACGCTGCCAAGG | |
|  |  | 401 | 450 |
| GRMZM2G471240_B73_ACB | (401) | ACATCAACCACTTTTACATGCAGAACTGCCCGCGCATCTTTCCTCAGAAG | |
| GRMZM2G471240_HD99_ACB | (324) | ACATCAACCACTTTTACATGGAGAACTGCCCGCGCATCTTCCCTCAGAAG | |
| GRMZM2G471240_PK6_ACD | (334) | ACATCAACTACTTTTACATGGAGAACTGCCCGCGCATCTTCCCTCAGAAG | |
|  |  | 451 | 500 |
| GRMZM2G471240_B73_ACB | (451) | TGAGTCCGATGCTGCCGCCATTGTTCTTGCATCCATCCAGCATCGTACGT | |
| GRMZM2G471240_HD99_ACB | (374) | TGAGTCCGATGCTGCCGCCATTGTTCTTGCATCCATGCATCCAGCATCGT | |
| GRMZM2G471240_PK6_ACD | (384) | TGAGTCCGATGCTGCCGCCATTGTTCTCGCATCCATCCAGCAT----CGT | |
|  |  | 501 | 550 |
| GRMZM2G471240_B73_ACB | (501) | ACGTCCTCTATACATCTGCGGATCATCATGTGCGCATGTTTGTGGCATGC | |
| GRMZM2G471240_HD99_ACB | (424) | ACGTCCTCTATACATCTGCGGATGATCATTGCGCATGTTTGTGGCATGC | |
| GRMZM2G471240_PK6_ACD | (430) | ACGTCCTCTATACATCTGCGGATGATCATTGCGCATGTTTGTGGCATGC | |
|  |  | 551 | 600 |
| GRMZM2G471240_B73_ACB | (551) | ATGCATGC-ATGTGAGCAGGAGCAGGCTTGCGGCCGCCATGTCCGCGCTG | |
| GRMZM2G471240_HD99_ACB | (474) | ATGCATGTGATGTGAGCAGGAGCAGGCTTGCGGCCGCCATGTCCGCGCTG | |
| GRMZM2G471240_PK6_ACD | (480) | AT--------GTGAGCAGGAGCAGGCTTGCGGCCGCCATGTCCGCGCTG | |
|  |  | 601 | 650 |
| GRMZM2G471240_B73_ACB | (600) | AGGAAGCCAAAGTACAACGGCAAGTGCATGCGCAGCCTGATTAGGAGCAT | |
| GRMZM2G471240_HD99_ACB | (524) | AGGAAGCCAAAGTACAACGGCAAGTGCATGCGCAGCCTGATTAGGAGCAT | |
| GRMZM2G471240_PK6_ACD | (521) | AGGAAGCCAAAGTACAACGGCAAGTGCATGCGCAGCCTGATTAGGAGCAT | |
|  |  | 651 | 700 |
| GRMZM2G471240_B73_ACB | (650) | CCTCGGCGAGACGAGGGTAAGCGAGACGCTGACCAACGTCATCATCCCTG | |
| GRMZM2G471240_HD99_ACB | (574) | CCTCGGCGAGACGAGGGTAAGCGAGACGCTGACCAACGTCATCATCCCTG | |
| GRMZM2G471240_PK6_ACD | (571) | CCTCGGCGAGACGAGGGTAAGCGAGACGCTGACCAACGTCATCATCCCTG | |
|  |  | 701 | 750 |
| GRMZM2G471240_B73_ACB | (700) | CCTTCGACATCAGGCTGCTGCAGCCTATCATCTTCTCCTACCTACGACGTA | |
| GRMZM2G471240_HD99_ACB | (624) | CCTTCGACATCAGGCTGCTGCAGCCTATCATCTTCTCCTACCTACGACGTA | |
| GRMZM2G471240_PK6_ACD | (621) | CCTTCGACATCAGGCTGCTGCAGCCTATCATCTTCTCCTACCTACGACGTA | |
|  |  | 751 | 800 |
| GRMZM2G471240_B73_ACB | (750) | CGTACGTCGTCACGAATGATTCATCTGTACGTCGTCGCATGCGAATGGCT | |

FIG.2 (beginning)

```
GRMZM2G471240_HD99_ACB  (674)  CGTACGTCGTCACGAATGATTCATCTGTACGTCGTCGCATGCGAATGGCT
GRMZM2G471240_PK6_ACD   (671)  CGTACGTCGTCACGAATGATTCATCTGTACGTCGTCGCATGCGAATGGCT
                               801                                              850
GRMZM2G471240_B73_ACB   (800)  GCCTACGTACGCCGTGCGCTAACATACTCAGCTCTTTCCTATCTGCTGCG
GRMZM2G471240_HD99_ACB  (724)  GCCTACGTACGCCGTGCGCTAACATACTCAGCTCTTTCCTATCTGCTGCG
GRMZM2G471240_PK6_ACD   (721)  GCCT----ACGCCGTGCGCTAACATACTCAGCTCTTTCCGATCTGCTGCG
                               851                                              900
GRMZM2G471240_B73_ACB   (850)  CCAATTTGCAGGCCAAGAGCACGCCTCTGAAGAACGCTCTGCTCTCGGAC
GRMZM2G471240_HD99_ACB  (774)  CCAATTTGCAGGCCAAGAGCACGCCTCTGAAGAACGCTCTGCTCTCGGAC
GRMZM2G471240_PK6_ACD   (767)  CCAATTTGCAGGCCAAGAGCACGCCTCTGAAGAACGCGCTGCTCTCGGAC
                               901                                              950
GRMZM2G471240_B73_ACB   (900)  GTGTGCATTGGCACGTCCGCCGCGCCGACCTACCTCCCGGCGCACTACTT
GRMZM2G471240_HD99_ACB  (824)  GTGTGCATTGGCACGTCCGCCGCGCCGACCTACCTCCCGGCGCACTACTT
GRMZM2G471240_PK6_ACD   (817)  GTGTGCATTGGCACGTCCGCCGCGCCGACCTACCTCCCGGCGCACTACTT
                               951                                              1000
GRMZM2G471240_B73_ACB   (950)  CCAGACTGAAGACGCCAACGGCAAGGAGCGCGAATACAACCTCATCGACG
GRMZM2G471240_HD99_ACB  (874)  CCAGACTGAAGACGCCAACGGCAAGGAGCGCGAATACAACCTCATCGACG
GRMZM2G471240_PK6_ACD   (867)  CCAGACTGAAGACGCCAACGGCAAGGAGCGCGAATACAACCTCATCGACG
                               1001                                             1050
GRMZM2G471240_B73_ACB   (1000) GCGGTGTGGCGGCCAACAACCCGGTAACTGACTAGCTAACTGGAAAACGC
GRMZM2G471240_HD99_ACB  (924)  GCGGTGTGGCGGCCAACAACCCGGTAACTGACTAGCTAACTGGAAAACGC
GRMZM2G471240_PK6_ACD   (917)  GCGGTGTGGCGGCCAACAACCCGGTAACTGACTAGCTAACTGCAAAACGA
                               1051                                             1100
GRMZM2G471240_B73_ACB   (1050) ACGCACAGACTCCATGTCCATGGCGGCCCACAAGGTCGATGCTAATTGTT
GRMZM2G471240_HD99_ACB  (974)  ACGCACAGACTCCATGTCCATGGCGGCCCACAAGGTCGATGCTAATTGTT
GRMZM2G471240_PK6_ACD   (967)  ACGCACAGACTCCATGTCCATGGCGGCCCACAAGGTCGATGCTAATTGTT
                               1101                                             1150
GRMZM2G471240_B73_ACB   (1100) GCTTATGTATGTCGCCCGATTGCACATGCGTAGACGATGGTTGCGATGAC
GRMZM2G471240_HD99_ACB  (1024) GCTTATGTATGTCGCCCGATTGCACATGCGTAGACGATGGTTGCGATGAC
GRMZM2G471240_PK6_ACD   (1017) GCTTATGTATGTCGCCCGATTGCACATGCGTAGACGATGGTTGCGATGAC
                               1151                                             1200
GRMZM2G471240_B73_ACB   (1150) GCAGATCACCAAAAAGATGCTTGCCAGCAAGGACAAGGCCGAGGAGCTGT
GRMZM2G471240_HD99_ACB  (1074) GCAGATCACCAAAAAGATGCTTGCCAGCAAGGACAAGGCCGAGGAGCTGT
GRMZM2G471240_PK6_ACD   (1067) GCAGATCACCAAAAAGATGCTTGCCAGCAAGGACAAGGCCGAGGAGCTGT
                               1201                                             1250
GRMZM2G471240_B73_ACB   (1200) ACCCAGTGAAGCCGTCGAACTGCCGCAGGTTCCTGGTGCTGTCCATCGGG
GRMZM2G471240_HD99_ACB  (1124) ACCCAGTGAAGCCGTCGAACTGCCGCAGGTTCCTGGTGCTGTCCATCGGG
GRMZM2G471240_PK6_ACD   (1117) ACCCAGTGAACCCGTCGAACTGCCGCAGGTTCCTGGTGCTGTCCATCGGG
                               1251                                             1300
GRMZM2G471240_B73_ACB   (1250) ACGGGGTCGACGTCCGAGCAGGGCCTCTACACGGCGCGGCAGTGCTCCCG
GRMZM2G471240_HD99_ACB  (1174) ACGGGGTCGACGTCCGAGCAGGGCCTCTACACGGCGCGGCAGTGCTCCCG
GRMZM2G471240_PK6_ACD   (1167) ACGGGGTCGACGTCCGAGCAGGGCCTCTACACGGCGCGGCAGTGCTCCCG
                               1301                                             1350
GRMZM2G471240_B73_ACB   (1300) GTGGGGTATCTGCCGGTGGCTCCGCAACAACGGCATGGCCCCCATCATCG
GRMZM2G471240_HD99_ACB  (1224) GTGGGGTATCTGCCGGTGGCTCCGCAACAACGGCATGGCCCCCATCATCG
GRMZM2G471240_PK6_ACD   (1217) GTGGGGCATCTGCCGGTGGCTCCGCAACAACGGCATGGCCCCCATCATCG
                               1351                                             1400
GRMZM2G471240_B73_ACB   (1350) ACATCTTCATGGCGGCCAGCTCGGACCTGGTGGACATCCACGTCGCCGCG
GRMZM2G471240_HD99_ACB  (1274) ACATCTTCATGGCGGCCAGCTCGGACCTGGTGGACATCCACGTCGCCGCG
GRMZM2G471240_PK6_ACD   (1267) ACATCTTCATGGCGGCCAGCTCGGACCTGGTGGACATCCACGTCGCCGCG
                               1401                                             1450
GRMZM2G471240_B73_ACB   (1400) ATGTTCCAGTCGCTCCACAGCGACGGCGACTACCTGCGCATCCAGGACAA
GRMZM2G471240_HD99_ACB  (1324) ATGTTCCAGTCGCTCCACAGCGACGGCGACTACCTGCGCATCCAGGACAA
GRMZM2G471240_PK6_ACD   (1317) ATGTTCCAGTCGCTCCACAGCGACGGCGACTACCTACGCATCCAGGACAA
                               1451                                             1500
GRMZM2G471240_B73_ACB   (1450) CTCGCTCCGTGGCGCCGCGGCCACCGTGGACGCGGCGACGCCGGAGAACA
GRMZM2G471240_HD99_ACB  (1374) CTCGCTCCGTGGCGCCGCGGCCACCGTGGACGCGGCGACGCCGGAGAACA
GRMZM2G471240_PK6_ACD   (1367) CTCGCTCCGTGGCGCCGCGGCAACCGTGGACGCGGCGACGCCGGAGAACA
```

FIG.2 (continuation 1)

```
                                    1501                                        1550
GRMZM2G471240_B73_ACB  (1500)  TGCGGACGCTCGTCGGGATCGGGGAGCGGATGCTGGCACAGAGGGTGTCC
GRMZM2G471240_HD99_ACB (1424)  TGCGGACGCTCGTCGGGATCGGGGAGCGGATGCTGGCACAGAGGGTGTCC
GRMZM2G471240_PK6_ACD  (1417)  TGCGGACGCTCGTCGGGATCGGGGAGCGGATGCTGGCACAGCGGGTGTCC
                                    1551                                        1600
GRMZM2G471240_B73_ACB  (1550)  AGGGTCAACGTGGAGACAGGGAG----GTACGAACCGGTGACTGGCGAAG
GRMZM2G471240_HD99_ACB (1474)  AGGGTCAACGTGGAGACAGGGAG----GTACGAACCGGTGACTGGCGAAG
GRMZM2G471240_PK6_ACD  (1467)  AGGGTCAACGTGGAGACAGGGAGCGAGGTACGAACCGGTGACCGGAGAAG
                                    1601                                        1650
GRMZM2G471240_B73_ACB  (1596)  GAAGCAATGCCGATGCCCTCGGTGGGCTCGCTAGGCAGCTCTCCGAGGAG
GRMZM2G471240_HD99_ACB (1520)  GAAGCAATGCCGATGCCCTCGGTGGGCTCGCTAGGCAGCTCTCCGAGGAG
GRMZM2G471240_PK6_ACD  (1517)  GAAGCAATGCCGATGCCCTCGGTGGGCTCGCTAGGCAGCTCTCCGAGGAG
                                    1651                                        1700
GRMZM2G471240_B73_ACB  (1646)  AGGAGAACAAGGCTCGCGCGCCGCGTCTCTGCCATCAACCCAAGAGGCTC
GRMZM2G471240_HD99_ACB (1570)  AGGAGAACAAGGCTCGCGCGCCGCGTCTCTGCCATCAACCCAAGAGGCTC
GRMZM2G471240_PK6_ACD  (1567)  AGGAGAACAAGGCTCGCGCGCCGCGTCTCTGCCATCAACCCCAGAAGCTC
                                    1701                                        1750
GRMZM2G471240_B73_ACB  (1696)  TAGATGTGCGTCGTACGATATCTAAGACAAGTGGCTTTACTGTCAGTCAC
GRMZM2G471240_HD99_ACB (1620)  TAGATGTGCGTCGTACGATATCTAAGACAAGTGGCTTTACTGTCAGTCAC
GRMZM2G471240_PK6_ACD  (1617)  TAGATGTGCGCCCTACGATATCTAAGACAAGTGGCTTTACTGTCAATCAC
                                    1751                                        1800
GRMZM2G471240_B73_ACB  (1746)  ATGCTTGTAAATAAGTAGACTTTATTTTAATAAAACATAAAAATATATAT
GRMZM2G471240_HD99_ACB (1670)  ATGCTTGTAAATAAGTAGACTTTATTTTAATAAAACATAAAAATATATAT
GRMZM2G471240_PK6_ACD  (1667)  ATGCTTGTAAATAAGTAGACTTTATTTTAATAAAATATAA--ATATATAT
                                    1801                                        1850
GRMZM2G471240_B73_ACB  (1796)  ATGTTCTTGAATATAAAATTGATAACCAAATTAAAATTCGAACCATCACT
GRMZM2G471240_HD99_ACB (1720)  ATGTTCTTGAATATAAAATTGATAACCAAATTAAAA--------------
GRMZM2G471240_PK6_ACD  (1715)  ATATTCT-------------GATAACCAAG-----ATTCGAACCCTCACT
                                    1851                             1897
GRMZM2G471240_B73_ACB  (1846)  TATACATAATTTTACTTATTTTTTATAAAACGTGAACGGGAAGGAC
GRMZM2G471240_HD99_ACB (1756)  ----------------------------------------------
GRMZM2G471240_PK6_ACD  (1747)  TATACACAATTTTATCTTATTTTTTATAAAACGTGAACG-------
```

FIG.2 (continuation 2)

```
                          1                                                          60
CDS_B73_T01      (1)    MASYSSRRPCNTCSTKAMAGSVVGEPVVLGQRVTVLTVDGGGVRGLIPGTILAFLEARLQ
CDS_B73_T02      (1)    MASYSSRRPCNTCSTKAMAGSVVGEPVVLGQRVTVLTVDGGGVRGLIPGTILAFLEARLQ
CDS_HD99_ACB     (1)    MASYSSRRPCNTCSTKAMAGSVVGEPVVLGQRVTVLTVDGGGVRGLIPGTILAFLEARLQ
CDS_PK6_ACD      (1)    MASYSSRRPCNTCSTKAMAGSVVGEPVVLGQRVTVLTVDGGGVRGLIPGTILAFLEARLQ
                          61                                                         120
CDS_B73_T01     (61)    ELDGPEARLADYFDYIAGTSTGGLITAMLTAPGKDKRPLYAAKDINHFYMQNCPRIFPQK
CDS_B73_T02     (61)    ELDGPEARLADYFDYIAGTSTGGLITAMLTAPGKDKRPLYAAKDINHFYMQNCPRIFPQK
CDS_HD99_ACB    (61)    ELDGPEARLADYFDYIAGTSTGGLITAMLTAPGKDKRPLYAAKDINHFYMENCPRIFPQK
CDS_PK6_ACD     (61)    ELDGPEARLADYFDYIAGTSTGGLITAMLTAPGKDKRPLYAAKDINYFYMENCPRIFPQK
                          121                                                        180
CDS_B73_T01    (121)    SRLAAAMSALRKPKYNGKCMRSLIRSILGETRVSETLTNVIIPAPDIRLLQPIIFSTYDA
CDS_B73_T02    (121)    SRLAAAMSALRKPKYNGKCMRSLIRSILGETR----------------------------A
CDS_HD99_ACB   (121)    SRLAAAMSALRKPKYNGKCMRSLIRSILGETRVSETLTNVIIPAPDIRLLQPIIFSTYDA
CDS_PK6_ACD    (121)    SRLAAAMSALRKPKYNGKCMRSLIRSILGETRVSETLTNVIIPAPDIRLLQPIIFSTYDA
                          181                                                        240
CDS_B73_T01    (181)    KSTPLKNALLSDVCIGTSAAPTYLPAHYFQTEDANGKEREYNLIDGGVAANNPTMVAMTQ
CDS_B73_T02    (154)    KSTPLKNALLSDVCIGTSAAPTYLPAHYFQTEDANGKEREYNLIDGGVAANNPTMVAMTQ
CDS_HD99_ACB   (181)    KSTPLKNALLSDVCIGTSAAPTYLPAHYFQTEDANGKEREYNLIDGGVAANNPTMVAMTQ
CDS_PK6_ACD    (181)    KSTPLKNALLSDVCIGTSAAPTYLPAHYFQTEDANGKEREYNLIDGGVAANNPTMVAMTQ
                          241                                                        300
CDS_B73_T01    (241)    ITKKMLASKDKAEELYPVKPSNCRRFLVLSIGTGSTSEQGLYTARQCSRWGICRWLRNNG
CDS_B73_T02    (214)    ITKKMLASKDKAEELYPVKPSNCRRFLVLSIGTGSTSEQGLYTARQCSRWGICRWLRNNG
CDS_HD99_ACB   (241)    ITKKMLASKDKAEELYPVKPSNCRRFLVLSIGTGSTSEQGLYTARQCSRWGICRWLRNNG
CDS_PK6_ACD    (241)    ITKKMLASKDKAEELYPVNPSNCRRFLVLSIGTGSTSEQGLYTARQCSRWGICRWLRNNG
                          301                                                        360
CDS_B73_T01    (301)    MAPIIDIFMAASSDLVDIHVAAMFQSLHSDGDYLRIQDNSLRGAAATVDAATPENMRTLV
CDS_B73_T02    (274)    MAPIIDIFMAASSDLVDIHVAAMFQSLHSDGDYLRIQDNSLRGAAATVDAATPENMRTLV
CDS_HD99_ACB   (301)    MAPIIDIFMAASSDLVDIHVAAMFQSLHSDGDYLRIQDNSLRGAAATVDAATPENMRTLV
CDS_PK6_ACD    (301)    MAPIIDIFMAASSDLVDIHVAAMFQSLHSDGDYLRIQDNSLRGAAATVDAATPENMRTLV
                          361                                                        420
CDS_B73_T01    (361)    GIGERMLAQRVSRVNVETGRYEPVTGEGSNADALGGLARQLSEERRTRLARRVSAINPRG
CDS_B73_T02    (334)    GIGERMLAQRVSRVNVETGRYEPVTGEGSNADALGGLARQLSEERRTRLARRVSAINPRG
CDS_HD99_ACB   (361)    GIGERMLAQRVSRVNVETGRYEPVTGEGSNADALGGLARQLSEERRTRLARRVSAINPRG
CDS_PK6_ACD    (361)    GIGERMLAQRVSRVNVETGSEVRTGDRRRKQCRCPRWAR---------------------
                          421
CDS_B73_T01    (421)    SRCASYDI
CDS_B73_T02    (394)    SRCASYDI
CDS_HD99_ACB   (421)    SRCASYDI
CDS_PK6_ACD    (400)    --------
```

FIG.3

SEQUENCE LISTING

```
<160> NUMBER OF SEQ ID NOS: 54

<210> SEQ ID NO 1
<211> LENGTH: 1785
<212> TYPE: DNA
<213> ORGANISM: maize

<400> SEQUENCE: 1
ggggtgtgcg gtcgaaggcg gcaatggcga gctactcgtc gcggcgtcca tgcaatacct      60
gtagcacgaa ggcgatggcc gggagcgtgg tcggcgagcc cgtcgtgctg gggcagaggg     120
tgacggtgct gacggtggac ggcggcggcg tccggggtct catcccggga accatcctcg     180
ccttcctgga ggccaggctg caggagctgg acggaccgga ggcgaggctg gcggactact     240
tcgactacat cgccggaacc agcaccggcg gtctcatcac cgccatgctc accgcgcccg     300
gcaaggacaa gcggcctctc tacgctgcca aggacatcaa ctacttttac atggagaact     360
```

```
gcccgcgcat cttccctcag aagtgagtcc gatgctgccg ccattgttct cgcatccatc    420
cagcatcgta cgtcctctat acatctgcgg atgatcattt gcgcatgttt gtggcatgca    480
tgtgagcagg agcaggcttg cggccgccat gtccgcgctg aggaagccaa agtacaacgg    540
caagtgcatg cgcagcctga ttaggagcat cctcggcgag acgagggtaa gcgagacgct    600
gaccaacgtc atcatccctg ccttcgacat caggctgctg cagcctatca tcttctctac    660
ctacgacgta cgtacgtcgt cacgaatgat tcatctgtac gtcgtcgcat gcgaatggct    720
gcctacgccg tgcgctaaca tactcagctc tttccgatct gctgcgccaa tttgcaggcc    780
aagagcacgc ctctgaagaa cgcgctgctc tcggacgtgt gcattggcac gtccgccgcg    840
ccgacctacc tcccggcgca ctacttccag actgaagacg ccaacggcaa ggagcgcgaa    900
tacaacctca tcgacggcgg tgtggcggcc aacaacccgg taactgacta gctaactgca    960
aaacgaacgc acagactcca tgtccatggc ggcccacaag gtcgatgcta attgttgctt   1020
atgtatgtcg cccgattgca catgcgtaga cgatggttgc gatgacgcag atcaccaaaa   1080
agatgcttgc cagcaaggac aaggccgagg agctgtaccc agtgaacccg tcgaactgcc   1140
gcaggttcct ggtgctgtcc atcgggacgg ggtcgacgtc cgagcagggc ctctacacgg   1200
cgcggcagtg ctcccggtgg ggcatctgcc ggtggctccg caacaacggc atggccccca   1260
tcatcgacat cttcatggcg gccagctcgg acctggtgga catccacgtc gccgcgatgt   1320
tccagtcgct ccacagcgac ggcgactacc tacgcatcca ggacaactcg ctccgtggcg   1380
ccgcggcaac cgtggacgcg gcgacgccgg agaacatgcg gacgctcgtc gggatcgggg   1440
agcggatgct ggcacagcgg gtgtccaggt caacgtgga cagggagc gaggtacgaa   1500 ccggtgaccg gagaaggaag caatgccgat gccctcggtg ggctcgctag gcagctctcc   1560
gaggagagga gaacaaggct cgcgcgccgc gtctctgcca tcaaccccag aagctctaga   1620
tgtgcgccct acgatatcta agacaagtgg ctttactgtc aatcacatgc ttgtaaataa   1680
gtagacttta ttttaataaa atataaatat atatatattc tgataaccaa gattcgaacc   1740
ctcacttata cacaattttta tcttattttt tataaaacgt gaacg              1785
```

```
<210> SEQ ID NO 2
<211> LENGTH: 1755
<212> TYPE: DNA
<213> ORGANISM: maize

<400> SEQUENCE: 2
```

```
gtcgaaggcg gcaatggcga gctactcgtc gcggcgtcca tgcaatacct gtagcacgaa     60
ggcgatggcc gggagcgtgg tcggcgagcc cgtcgtgctg gggcagaggg tgacggtgct    120
gacggtggac ggcggcggcg tccggggtct catcccggga accatcctcg ccttcctgga    180
ggccaggctg caggagctgg acggaccgga ggcgaggctg gcggactact cgactacat    240 cgccggaacc agcaccggcg gtctcatcac cgccatgctc accgcgcccg gcaaggacaa    300
gcggcctctc tacgctgcca aggacatcaa ccacttttac atggagaact gcccgcgcat    360
cttccctcag aagtgagtcc gatgctgccg ccattgttct gcatccatg catccagcat    420 cgtacgtcct ctatacatct gcggatgatc atttgcgcat gtttgtggca tgcatgcatg    480
tgatgtgagc aggagcaggc ttgcggccgc catgtccgcg ctgaggaagc caaagtacaa    540
cggcaagtgc atgcgcagcc tgattaggag catcctcggc gagacgaggg taagcgagac    600
gctgaccaac gtcatcatcc ctgccttcga catcaggctg ctgcagccta tcatcttctc    660
tacctacgac gtacgtacgt cgtcacgaat gattcatctg tacgtcgtcg catgcgaatg    720
```

| | |
|---|---|
| gctgcctacg tacgccgtgc gctaacatac tcagctcttt cctatctgct gcgccaattt | 780 |
| gcaggccaag agcacgcctc tgaagaacgc tctgctctcg dacgtgtgca ttggcacgtc | 840 |
| cgccgcgccg acctacctcc cggcgcacta cttccagact gaagacgcca acggcaagga | 900 |
| gcgcgaatac aacctcatcg acggcggtgt ggcggccaac aacccggtaa ctgactagct | 960 |
| aactggaaaa cggacgcaca gactccatgt ccatggcggc ccacaaggtc gatgctaatt | 1020 |
| gttgcttatg tatgtcgccc gattgcacat gcgtagacga tggttgcgat gacgcagatc | 1080 |
| accaaaaaga tgcttgccag caaggacaag gccgaggagc tgtacccagt gaagccgtcg | 1140 |
| aactgccgca ggttcctggt gctgtccatc gggacggggt cgacgtccga gcagggcctc | 1200 |
| tacacggcgc ggcagtgctc ccggtggggt atctgccggt ggctccgcaa caacggcatg | 1260 |
| gcccccatca tcgacatctt catggcggcc agctcggacc tggtggacat ccacgtcgcc | 1320 |
| gcgatgttcc agtcgctcca cagcgacggc gactacctgc gcatccagga caactcgctc | 1380 |
| cgtggcgccg cggccaccgt ggacgcgcg acgccggaga acatgcggac gctcgtcggg | 1440 |
| atcggggagc ggatgctggc acagagggtg tccagggtca acgtggagac agggaggtac | 1500 |
| gaaccggtga ctggcgaagg aagcaatgcc gatgccctcg gtgggctcgc taggcagctc | 1560 |
| tccgaggaga ggagaacaag gctcgcgcgc gcgtctctg ccatcaaccc aagaggctct | 1620 |
| agatgtgcgt cgtacgatat ctaagacaag tggctttact gtcagtcaca tgcttgtaaa | 1680 |
| taagtagact ttattttaat aaaacataaa aatatatata tgttcttgaa tataaaattg | 1740 |
| ataaccaaat taaaa | 1755 |

<210> SEQ ID NO 3
<211> LENGTH: 1410
<212> TYPE: DNA
<213> ORGANISM: maize

<400> SEQUENCE: 3

| | |
|---|---|
| agttcatcac taatcacact tattgtgccc tcgacgagta tctagctagc tcattaatcg | 60 |
| atcaatcggg gtgtgcggtc gaaggcggca atggcgagct actcgtcgcg gcgtccatgc | 120 |
| aataccttgta gcacgaaggc gatggccggg agcgtggtcg gcgagcccgt cgtgctgggg | 180 |
| cagagggtga cggtgctgac ggtggacggc ggcggcgtcc ggggtctcat cccgggaacc | 240 |
| atcctcgcct tcctggaggc caggctgcag gagctggacg gaccggaggc gaggctggcg | 300 |
| gactacttcg actacatcgc cggaaccagc accggcggtc tcatcaccgc catgctcacc | 360 |
| gcgcccggca aggacaagcg gcctctctac gctgccaagg acatcaacta cttttacatg | 420 |
| gagaactgcc cgcgcatctt ccctcagaag agcaggcttg cggccgccat gtccgcgctg | 480 |
| aggaagccaa agtacaacgg caagtgcatg cgcagcctga ttaggagcat cctcggcgag | 540 |
| acgagggtaa gcgagacgct gaccaacgtc atcatccctg ccttcgacat caggctgctg | 600 |
| cagcctatca tcttctctac ctacgacgcc aagagcacgc ctctgaagaa cgcgctgctc | 660 |
| tcggacgtgt gcattggcac gtccgccgcg ccgacctacc tcccggcgca ctacttccag | 720 |
| actgaagacg ccaacggcaa ggagcgcgaa tacaacctca tcgacggcgg tgtggcggcc | 780 |
| aacaacccga cgatggttgc gatgacgcag atcaccaaaa agatgcttgc cagcaaggac | 840 |
| aaggccgagg agctgtaccc agtgaacccg tcgaactgcc gcaggttcct ggtgctgtcc | 900 |
| atcgggacgg ggtcgacgtc cgagcagggc ctctacacgg cgcggcagtg ctcccggtgg | 960 |
| ggcatctgcc ggtggctccg caacaacggc atggcccca tcatcgacat cttcatggcg | 1020 |
| gccagctcgg acctggtgga catccacgtc gccgcgatgt tccagtcgct ccacagcgac | 1080 |

```
ggcgactacc tacgcatcca ggacaactcg ctccgtggcg ccgcggcaac cgtggacgcg    1140
gcgacgccgg agaacatgcg gacgctcgtc gggatcgggg agcggatgct ggcacagcgg    1200
gtgtccaggg tcaacgtgga gacagggagc gaggtacgaa ccggtgaccg gagaaggaag    1260
caatgccgat gccctcggtg ggctcgctag gcagctctcc gaggagagga gaacaaggct    1320
cgcgcgccgc gtctctgcca tcaaccccag aagctctaga tgtgcgccct acgatatcta    1380
agacaagtgg ctttactgtc aatcacatgc                                     1410
```

<210> SEQ ID NO 4
<211> LENGTH: 1406
<212> TYPE: DNA
<213> ORGANISM: maize

<400> SEQUENCE: 4

```
agttcatcac taatcacact tattgtgccc tcgacgagta tctatagcta gctcattaat     60
cgattcgggg gtgtgttgtc gaaggcggca atggcgagct actcgtcgcg gcgtccatgc    120
aatacctgta gcacgaaggc gatggccggg agcgtggtcg gcgagcccgt cgtgctgggg    180
cagagggtga cggtgctgac ggtggacggc ggcggcgtcc ggggtctcat cccgggaacc    240
atcctcgcct tcctggaggc caggctgcag gagctggacg gaccggaggc gaggctggcg    300
gactacttcg actacatcgc cggaaccagc accggcggtc tcatcaccgc catgctcacc    360
gcgcccggca aggacaagcg gcctctctac gctgccaagg acatcaacca cttttacatg    420
gagaactgcc cgcgcatctt ccctcagaag agcaggcttg cggccgccat gtccgcgctg    480
aggaagccaa agtacaacgg caagtgcatg cgcagcctga ttaggagcat cctcggcgag    540
acgagggtaa gcgagacgct gaccaacgtc atcatccctg ccttcgacat caggctgctg    600
cagcctatca tcttctctac ctacgacgcc aagagcacgc ctctgaagaa cgctctgctc    660
tcggacgtgt gcattggcac gtccgccgcg ccgacctacc tcccggcgca ctacttccag    720
actgaagacg ccaacggcaa ggagcgcgaa tacaacctca tcgacggcgg tgtggcggcc    780
aacaacccga cgatggttgc gatgacgcag atcaccaaaa agatgcttgc cagcaaggac    840
aaggccgagg agctgtaccc agtgaagccg tcgaactgcc gcaggttcct ggtgctgtcc    900
atcgggacgg ggtcgacgtc cgagcagggc ctctacacgg cgcggcagtg ctcccggtgg    960
ggtatctgcc ggtggctccg caacaacggc atggcccccca tcatcgacat cttcatggcg   1020
gccagctcgg acctggtgga catccacgtc gccgcgatgt ccagtcgct ccacagcgac    1080 ggcgactacc tgcgcatcca ggacaactcg ctccgtggcg ccgcggccac cgtggacgcg    1140
gcgacgccgg agaacatgcg gacgctcgtc gggatcgggg agcggatgct ggcacagagg    1200
gtgtccaggg tcaacgtgga gacagggagg tacgaaccgg tgactggcga aggaagcaat    1260
gccgatgccc tcggtgggct cgctaggcag ctctccgagg agaggagaac aaggctcgcg    1320
cgccgcgtct ctgccatcaa cccaagaggc tctagatgtg cgtcgtacga tatctaagac   1380
aagtggcttt actgtcagtc acatgc                                         1406
```

<210> SEQ ID NO 5
<211> LENGTH: 154
<212> TYPE: DNA
<213> ORGANISM: maize
<220> FEATURE:
<221> NAME/KEY: misc_feature
<222> LOCATION: (41)..(41)
<223> OTHER INFORMATION: n is a, c, g, or t

```
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t

<400> SEQUENCE: 5
gcggacgctc gtcgggatcg gggagcggat gctggcacag ngggtgtcca gggtcaacgt      60
ggagacaggg agcgaggtac gaaccggtga cnggngaagg aagcaatgcc gatgccctcg     120
gtgggctcgc taggcagctc tccgaggaga ggag                                 154

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
gagaaggaag caatgccgat gcc                                              23

<210> SEQ ID NO 7
<211> LENGTH: 33
<212> TYPE: DNA
<213> ORGANISM: Artificial Sequence
<220> FEATURE:
<223> OTHER INFORMATION: PRIMER

<400> SEQUENCE: 7
tgattgacag taaagccact tgtcttagat atc                                   33

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
tacccgattg agcatggca                                                   19

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
tcttcaggcg aaacacgga                                                   19

<210> SEQ ID NO 10
<211> LENGTH: 29
<212> TYPE: DNA
<213> ORGANISM: Artificial Sequence
<220> FEATURE:
<223> OTHER INFORMATION: primer

<400> SEQUENCE: 10
agttcatcac taatcacact tattgtgcc                                        29
```

```
<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
ggcggacgtg ccaatgca                                                18

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
atgtccgcgc tgaggaagcc a                                            21

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gagcactgcc gcgccgtgta                                              20

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
ggagctgtac ccagtgaagc cg                                           22

<210> SEQ ID NO 15
<211> LENGTH: 27
<212> TYPE: DNA
<213> ORGANISM: Artificial Sequence
<220> FEATURE:
<223> OTHER INFORMATION: primer

<400> SEQUENCE: 15
ttagatatcg tacgacgcac atctaga                                      27

<210> SEQ ID NO 16
<211> LENGTH: 18
<212> TYPE: DNA
<213> ORGANISM: Artificial Sequence
<220> FEATURE:
<223> OTHER INFORMATION: primer

<400> SEQUENCE: 16
tatattcaag aacatata                                                18

<210> SEQ ID NO 17
<211> LENGTH: 20
<212> TYPE: DNA
<213> ORGANISM: Artificial Sequence
<220> FEATURE:
<223> OTHER INFORMATION: primer
```

<400> SEQUENCE: 17
gaacgctctg ctctcggacg                                              20

<210> SEQ ID NO 18
<211> LENGTH: 49
<212> TYPE: DNA
<213> ORGANISM: Artificial Sequence
<220> FEATURE:
<223> OTHER INFORMATION: primer

<400> SEQUENCE: 18
ggggacaagt ttgtacaaaa aagcaggctt tcgacgtccg agcagggcc              49

<210> SEQ ID NO 19
<211> LENGTH: 55
<212> TYPE: DNA
<213> ORGANISM: Artificial Sequence
<220> FEATURE:
<223> OTHER INFORMATION: primer

<400> SEQUENCE: 19
ggggaccact ttgtacaaga aagctgggtt caccgagggc atcggcattg cttcc       55

<210> SEQ ID NO 20
<211> LENGTH: 49
<212> TYPE: DNA
<213> ORGANISM: Artificial Sequence
<220> FEATURE:
<223> OTHER INFORMATION: primer

<400> SEQUENCE: 20
ggggacaagt ttgtacaaaa aagcaggctt aggcaatggc gagctactc              49

<210> SEQ ID NO 21
<211> LENGTH: 48
<212> TYPE: DNA
<213> ORGANISM: Artificial Sequence
<220> FEATURE:
<223> OTHER INFORMATION: primer

<400> SEQUENCE: 21
ggggaccact ttgtacaaga aagctgggta gccttgttct cctctcct               48

<210> SEQ ID NO 22
<211> LENGTH: 48
<212> TYPE: DNA
<213> ORGANISM: Artificial Sequence
<220> FEATURE:
<223> OTHER INFORMATION: primer

<400> SEQUENCE: 22
ggggaccact ttgtacaaga aagctgggta gccacttgtc ttagatat               48

<210> SEQ ID NO 23
<211> LENGTH: 1892
<212> TYPE: DNA
<213> ORGANISM: maize

<400> SEQUENCE: 23
agttcatcac taatcacact tattgtgccc tcgacgagta tctatagcta gctcattaat   60
cgattcgggg gtgtgttgtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240

-continued

```
atcctcgcct tcctggaggc caggctgcag gagctggacg gaccggaggc gaggctggcg    300
gactacttcg actacatcgc cggaaccagc accggcggtc tcatcaccgc catgctcacc    360
gcgcccggca aggacaagcg gcctctctac gctgccaagg acatcaacca cttttacatg    420
cagaactgcc cgcgcatctt tcctcagaag tgagtccgat gctgccgcca ttgttcttgc    480
atccatccag catcgtacgt acgtcctcta tacatctgcg gatcatcatg tgcgcatgtt    540
tgtggcatgc atgcatgcat gtgagcagga gcaggcttgc ggccgccatg tccgcgctga    600
ggaagccaaa gtacaacggc aagtgcatgc gcagcctgat taggagcatc ctcggcgaga    660
cgagggtaag cgagacgctg accaacgtca tcatccctgc cttcgacatc aggctgctgc    720
agcctatcat cttctctacc tacgacgtac gtacgtcgtc acgaatgatt catctgtacg    780
tcgtcgcatg cgaatggctg cctacgtacg ccgtgcgcta acatactcag ctctttccta    840
tctgctgcgc caatttgcag gccaagagca cgcctctgaa gaacgctctg ctctcggacg    900
tgtgcattgg cacgtccgcc gcgccgacct acctcccggc gcactacttc cagactgaag    960
acgccaacgg caaggagcgc gaatacaacc tcatcgacgg cggtgtggcg ccaacaacc    1020
cggtaactga ctagctaact ggaaaacgga cgcacagact ccatgtccat ggcggcccac    1080
aaggtcgatg ctaattgttg cttatgtatg tcgcccgatt gcacatgcgt agacgatggt    1140
tgcgatgacg cagatcacca aaaagatgct tgccagcaag gacaaggccg aggagctgta    1200
cccagtgaag ccgtcgaact gccgcaggtt cctggtgctg tccatcggga cggggtcgac    1260
gtccgagcag ggcctctaca cggcgcggca gtgctcccgg tggggtatct gccggtggct    1320
ccgcaacaac ggcatggccc ccatcatcga catcttcatg cggccagct cggacctggt    1380
ggacatccac gtcgccgcga tgttccagtc gctccacagc gacggcgact acctgcgcat    1440
ccaggacaac tcgctccgtg cgccgcggc caccgtggac gcggcgacgc cggagaacat    1500
gcggacgctc gtcgggatcg gggagcggat gctggcacag agggtgtcca gggtcaacgt    1560
ggagacaggg aggtacgaac cggtgactgg cgaaggaagc aatgccgatg ccctcggtgg    1620
gctcgctagg cagctctccg aggagaggag aacaaggctc gcgcgccgcg tctctgccat    1680
caacccaaga ggctctagat gtgcgtcgta cgatatctaa gacaagtggc tttactgtca    1740
gtcacatgct tgtaaataag tagactttat tttaataaaa cataaaaata tatatatgtt    1800
cttgaatata aaattgataa ccaaattaaa attcgaacca tcacttatac ataattttac    1860
tttattttt ataaaacgtg aacgggaagg ac                                  1892
```

<210> SEQ ID NO 24
<211> LENGTH: 399
<212> TYPE: PRT
<213> ORGANISM: maize

<400> SEQUENCE: 24

```
Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Val Arg Gly Leu Ile Pro
        35                  40                  45

Gly Thr Ile Leu Ala Phe Leu Glu Ala Arg Leu Gln Glu Leu Asp Gly
    50                  55                  60

Pro Glu Ala Arg Leu Ala Asp Tyr Phe Asp Tyr Ile Ala Gly Thr Ser
65                  70                  75                  80
```

```
Thr Gly Gly Leu Ile Thr Ala Met Leu Thr Ala Pro Gly Lys Asp Lys
                85                  90                  95

Arg Pro Leu Tyr Ala Ala Lys Asp Ile Asn Tyr Phe Tyr Met Glu Asn
            100                 105                 110

Cys Pro Arg Ile Phe Pro Gln Lys Ser Arg Leu Ala Ala Ala Met Ser
        115                 120                 125

Ala Leu Arg Lys Pro Lys Tyr Asn Gly Lys Cys Met Arg Ser Leu Ile
    130                 135                 140

Arg Ser Ile Leu Gly Glu Thr Arg Val Ser Glu Thr Leu Thr Asn Val
145                 150                 155                 160

Ile Ile Pro Ala Phe Asp Ile Arg Leu Leu Gln Pro Ile Ile Phe Ser
                165                 170                 175

Thr Tyr Asp Ala Lys Ser Thr Pro Leu Lys Asn Ala Leu Leu Ser Asp
            180                 185                 190

Val Cys Ile Gly Thr Ser Ala Ala Pro Thr Tyr Leu Pro Ala His Tyr
        195                 200                 205

Phe Gln Thr Glu Asp Ala Asn Gly Lys Glu Arg Glu Tyr Asn Leu Ile
    210                 215                 220

Asp Gly Gly Val Ala Ala Asn Asn Pro Thr Met Val Ala Met Thr Gln
225                 230                 235                 240

Ile Thr Lys Lys Met Leu Ala Ser Lys Asp Lys Ala Glu Glu Leu Tyr
                245                 250                 255

Pro Val Asn Pro Ser Asn Cys Arg Arg Phe Leu Val Leu Ser Ile Gly
            260                 265                 270

Thr Gly Ser Thr Ser Glu Gln Gly Leu Tyr Thr Ala Arg Gln Cys Ser
        275                 280                 285

Arg Trp Gly Ile Cys Arg Trp Leu Arg Asn Asn Gly Met Ala Pro Ile
    290                 295                 300

Ile Asp Ile Phe Met Ala Ala Ser Ser Asp Leu Val Asp Ile His Val
305                 310                 315                 320

Ala Ala Met Phe Gln Ser Leu His Ser Asp Gly Asp Tyr Leu Arg Ile
                325                 330                 335

Gln Asp Asn Ser Leu Arg Gly Ala Ala Ala Thr Val Asp Ala Ala Thr
            340                 345                 350

Pro Glu Asn Met Arg Thr Leu Val Gly Ile Gly Glu Arg Met Leu Ala
        355                 360                 365

Gln Arg Val Ser Arg Val Asn Val Glu Thr Gly Ser Glu Val Arg Thr
    370                 375                 380

Gly Asp Arg Arg Arg Lys Gln Cys Arg Cys Pro Arg Trp Ala Arg
385                 390                 395

<210> SEQ ID NO 25
<211> LENGTH: 428
<212> TYPE: PRT
<213> ORGANISM: maize

<400> SEQUENCE: 25

Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Val Arg Gly Leu Ile Pro
        35                  40                  45

Gly Thr Ile Leu Ala Phe Leu Glu Ala Arg Leu Gln Glu Leu Asp Gly
    50                  55                  60
```

Pro Glu Ala Arg Leu Ala Asp Tyr Phe Asp Tyr Ile Ala Gly Thr Ser
65                  70                  75                  80

Thr Gly Gly Leu Ile Thr Ala Met Leu Thr Ala Pro Gly Lys Asp Lys
            85                  90                  95

Arg Pro Leu Tyr Ala Ala Lys Asp Ile Asn His Phe Tyr Met Glu Asn
            100                 105                 110

Cys Pro Arg Ile Phe Pro Gln Lys Ser Arg Leu Ala Ala Ala Met Ser
            115                 120                 125

Ala Leu Arg Lys Pro Lys Tyr Asn Gly Lys Cys Met Arg Ser Leu Ile
        130                 135                 140

Arg Ser Ile Leu Gly Glu Thr Arg Val Ser Glu Thr Leu Thr Asn Val
145                 150                 155                 160

Ile Ile Pro Ala Phe Asp Ile Arg Leu Leu Gln Pro Ile Ile Phe Ser
                165                 170                 175

Thr Tyr Asp Ala Lys Ser Thr Pro Leu Lys Asn Ala Leu Leu Ser Asp
            180                 185                 190

Val Cys Ile Gly Thr Ser Ala Ala Pro Thr Tyr Leu Pro Ala His Tyr
            195                 200                 205

Phe Gln Thr Glu Asp Ala Asn Gly Lys Glu Arg Glu Tyr Asn Leu Ile
        210                 215                 220

Asp Gly Gly Val Ala Ala Asn Asn Pro Thr Met Val Ala Met Thr Gln
225                 230                 235                 240

Ile Thr Lys Lys Met Leu Ala Ser Lys Asp Lys Ala Glu Glu Leu Tyr
                245                 250                 255

Pro Val Lys Pro Ser Asn Cys Arg Arg Phe Leu Val Leu Ser Ile Gly
            260                 265                 270

Thr Gly Ser Thr Ser Glu Gln Gly Leu Tyr Thr Ala Arg Gln Cys Ser
            275                 280                 285

Arg Trp Gly Ile Cys Arg Trp Leu Arg Asn Asn Gly Met Ala Pro Ile
        290                 295                 300

Ile Asp Ile Phe Met Ala Ala Ser Ser Asp Leu Val Asp Ile His Val
305                 310                 315                 320

Ala Ala Met Phe Gln Ser Leu His Ser Asp Gly Asp Tyr Leu Arg Ile
                325                 330                 335

Gln Asp Asn Ser Leu Arg Gly Ala Ala Ala Thr Val Asp Ala Ala Thr
            340                 345                 350

Pro Glu Asn Met Arg Thr Leu Val Gly Ile Gly Glu Arg Met Leu Ala
            355                 360                 365

Gln Arg Val Ser Arg Val Asn Val Glu Thr Gly Arg Tyr Glu Pro Val
        370                 375                 380

Thr Gly Glu Gly Ser Asn Ala Asp Ala Leu Gly Gly Leu Ala Arg Gln
385                 390                 395                 400

Leu Ser Glu Glu Arg Arg Thr Arg Leu Ala Arg Arg Val Ser Ala Ile
                405                 410                 415

Asn Pro Arg Gly Ser Arg Cys Ala Ser Tyr Asp Ile
            420                 425

<210> SEQ ID NO 26
<211> LENGTH: 428
<212> TYPE: PRT
<213> ORGANISM: maize

<400> SEQUENCE: 26

```
Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Val Arg Gly Leu Ile Pro
        35                  40                  45

Gly Thr Ile Leu Ala Phe Leu Glu Ala Arg Leu Gln Glu Leu Asp Gly
    50                  55                  60

Pro Glu Ala Arg Leu Ala Asp Tyr Phe Asp Tyr Ile Ala Gly Thr Ser
65                  70                  75                  80

Thr Gly Gly Leu Ile Thr Ala Met Leu Thr Ala Pro Gly Lys Asp Lys
                85                  90                  95

Arg Pro Leu Tyr Ala Ala Lys Asp Ile Asn His Phe Tyr Met Gln Asn
            100                 105                 110

Cys Pro Arg Ile Phe Pro Gln Lys Ser Arg Leu Ala Ala Ala Met Ser
        115                 120                 125

Ala Leu Arg Lys Pro Lys Tyr Asn Gly Lys Cys Met Arg Ser Leu Ile
    130                 135                 140

Arg Ser Ile Leu Gly Glu Thr Arg Val Ser Glu Thr Leu Thr Asn Val
145                 150                 155                 160

Ile Ile Pro Ala Phe Asp Ile Arg Leu Leu Gln Pro Ile Ile Phe Ser
                165                 170                 175

Thr Tyr Asp Ala Lys Ser Thr Pro Leu Lys Asn Ala Leu Leu Ser Asp
            180                 185                 190

Val Cys Ile Gly Thr Ser Ala Ala Pro Thr Tyr Leu Pro Ala His Tyr
        195                 200                 205

Phe Gln Thr Glu Asp Ala Asn Gly Lys Glu Arg Glu Tyr Asn Leu Ile
    210                 215                 220

Asp Gly Gly Val Ala Ala Asn Asn Pro Thr Met Val Ala Met Thr Gln
225                 230                 235                 240

Ile Thr Lys Lys Met Leu Ala Ser Lys Asp Lys Ala Glu Glu Leu Tyr
                245                 250                 255

Pro Val Lys Pro Ser Asn Cys Arg Arg Phe Leu Val Leu Ser Ile Gly
            260                 265                 270

Thr Gly Ser Thr Ser Glu Gln Gly Leu Tyr Thr Ala Arg Gln Cys Ser
        275                 280                 285

Arg Trp Gly Ile Cys Arg Trp Leu Arg Asn Asn Gly Met Ala Pro Ile
    290                 295                 300

Ile Asp Ile Phe Met Ala Ala Ser Ser Asp Leu Val Asp Ile His Val
305                 310                 315                 320

Ala Ala Met Phe Gln Ser Leu His Ser Asp Gly Asp Tyr Leu Arg Ile
                325                 330                 335

Gln Asp Asn Ser Leu Arg Gly Ala Ala Ala Thr Val Asp Ala Ala Thr
            340                 345                 350

Pro Glu Asn Met Arg Thr Leu Val Gly Ile Gly Glu Arg Met Leu Ala
        355                 360                 365

Gln Arg Val Ser Arg Val Asn Val Glu Thr Gly Arg Tyr Glu Pro Val
    370                 375                 380

Thr Gly Glu Gly Ser Asn Ala Asp Ala Leu Gly Gly Leu Ala Arg Gln
385                 390                 395                 400
```

```
Leu Ser Glu Glu Arg Arg Thr Arg Leu Ala Arg Val Ser Ala Ile
                405                 410                 415
Asn Pro Arg Gly Ser Arg Cys Ala Ser Tyr Asp Ile
            420                 425

<210> SEQ ID NO 27
<211> LENGTH: 401
<212> TYPE: PRT
<213> ORGANISM: maize

<400> SEQUENCE: 27

Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Val Arg Gly Leu Ile Pro
            35                  40                  45

Gly Thr Ile Leu Ala Phe Leu Glu Ala Arg Leu Gln Glu Leu Asp Gly
    50                  55                  60

Pro Glu Ala Arg Leu Ala Asp Tyr Phe Asp Tyr Ile Ala Gly Thr Ser
65                  70                  75                  80

Thr Gly Gly Leu Ile Thr Ala Met Leu Thr Ala Pro Gly Lys Asp Lys
                85                  90                  95

Arg Pro Leu Tyr Ala Ala Lys Asp Ile Asn His Phe Tyr Met Gln Asn
            100                 105                 110

Cys Pro Arg Ile Phe Pro Gln Lys Ser Arg Leu Ala Ala Ala Met Ser
        115                 120                 125

Ala Leu Arg Lys Pro Lys Tyr Asn Gly Lys Cys Met Arg Ser Leu Ile
130                 135                 140

Arg Ser Ile Leu Gly Glu Thr Arg Ala Lys Ser Thr Pro Leu Lys Asn
145                 150                 155                 160

Ala Leu Leu Ser Asp Val Cys Ile Gly Thr Ser Ala Ala Pro Thr Tyr
                165                 170                 175

Leu Pro Ala His Tyr Phe Gln Thr Glu Asp Ala Asn Gly Lys Glu Arg
            180                 185                 190

Glu Tyr Asn Leu Ile Asp Gly Gly Val Ala Ala Asn Pro Thr Met
        195                 200                 205

Val Ala Met Thr Gln Ile Thr Lys Lys Met Leu Ala Ser Lys Asp Lys
210                 215                 220

Ala Glu Glu Leu Tyr Pro Val Lys Pro Ser Asn Cys Arg Arg Phe Leu
225                 230                 235                 240

Val Leu Ser Ile Gly Thr Gly Ser Thr Ser Glu Gln Gly Leu Tyr Thr
                245                 250                 255

Ala Arg Gln Cys Ser Arg Trp Gly Ile Cys Arg Trp Leu Arg Asn Asn
            260                 265                 270

Gly Met Ala Pro Ile Ile Asp Ile Phe Met Ala Ala Ser Ser Asp Leu
        275                 280                 285

Val Asp Ile His Val Ala Ala Met Phe Gln Ser Leu His Ser Asp Gly
290                 295                 300

Asp Tyr Leu Arg Ile Gln Asp Asn Ser Leu Arg Gly Ala Ala Ala Thr
305                 310                 315                 320

Val Asp Ala Ala Thr Pro Glu Asn Met Arg Thr Leu Val Gly Ile Gly
                325                 330                 335

Glu Arg Met Leu Ala Gln Arg Val Ser Arg Val Asn Val Glu Thr Gly
            340                 345                 350
```

-continued

```
Arg Tyr Glu Pro Val Thr Gly Glu Gly Ser Asn Ala Asp Ala Leu Gly
            355                 360                 365

Gly Leu Ala Arg Gln Leu Ser Glu Glu Arg Arg Thr Arg Leu Ala Arg
    370                 375                 380

Arg Val Ser Ala Ile Asn Pro Arg Gly Ser Arg Cys Ala Ser Tyr Asp
385                 390                 395                 400

Ile

<210> SEQ ID NO 28
<211> LENGTH: 422
<212> TYPE: PRT
<213> ORGANISM: Hordeum vulgare

<400> SEQUENCE: 28

Met Ala Ser Tyr Trp Cys Arg Arg Pro Cys Glu Ser Cys Ser Thr Arg
1               5                   10                  15

Ala Met Ala Gly Ser Val Val Gly Gln Pro Val Ala Pro Gly Gln Arg
            20                  25                  30

Val Thr Val Leu Thr Ile Asp Gly Gly Ile Arg Gly Leu Ile Pro
        35                  40                  45

Gly Thr Ile Leu Ala Phe Leu Glu Ala Arg Leu Gln Glu Leu Asp Gly
    50                  55                  60

Pro Asp Ala Arg Leu Ala Asp Tyr Phe Asp Cys Ile Ala Gly Thr Ser
65                  70                  75                  80

Thr Gly Gly Leu Ile Thr Ala Met Leu Thr Ala Pro Gly Gln Asp Gly
                85                  90                  95

Arg Pro Leu Phe Ala Ala Lys Asp Val Asn Arg Phe Tyr Leu Asp Asn
            100                 105                 110

Gly Pro Tyr Ile Phe Pro Gln Arg Arg Cys Ala Leu Ala Ala Val Thr
        115                 120                 125

Ala Ser Leu Arg Arg Pro Arg Tyr Ser Gly Lys Tyr Leu His Gly Lys
    130                 135                 140

Ile Arg Ser Met Leu Gly Glu Thr Arg Leu Cys Asp Ala Leu Thr Asp
145                 150                 155                 160

Val Val Ile Pro Thr Phe Asp Val Lys Leu Leu Gln Pro Ile Ile Phe
                165                 170                 175

Ser Thr Tyr Asp Ala Arg Asn Met Pro Leu Lys Asn Ala Arg Leu Ala
            180                 185                 190

Asp Ile Cys Ile Gly Thr Ser Ala Ala Pro Thr Tyr Leu Pro Ala His
        195                 200                 205

His Phe His Thr Gln Asp Asp Asn Gly Lys Glu Arg Glu Tyr Asn Leu
    210                 215                 220

Ile Asp Gly Gly Val Ala Ala Asn Asn Pro Thr Met Val Thr Met Thr
225                 230                 235                 240

Gln Ile Thr Lys Lys Met Met Val Lys Asp Arg Glu Glu Leu Tyr Pro
                245                 250                 255

Val Lys Pro Ser Asp Cys Gly Lys Phe Leu Val Leu Ser Ile Gly Thr
            260                 265                 270

Gly Ser Thr Ser Asp Gln Gly Leu Tyr Thr Ala Lys Gln Cys Ser Gln
        275                 280                 285

Trp Gly Ile Ile Arg Trp Leu Arg Asn Lys Gly Met Ala Pro Ile Ile
    290                 295                 300

Asp Ile Phe Met Ala Ala Ser Ser Asp Leu Val Asp Ile His Ala Ala
305                 310                 315                 320
```

Val Leu Phe Gln Ser Leu His Ser Asp Gly Asn Tyr Leu Arg Ile Gln
            325                 330                 335

Asp Asn Ser Leu His Gly Pro Ala Ala Thr Val Asp Ala Ala Thr Pro
            340                 345                 350

Glu Asn Met Ala Glu Leu Leu Arg Ile Gly Glu Arg Met Leu Ala Gln
            355                 360                 365

Arg Val Ser Arg Val Asn Val Glu Thr Gly Arg Tyr Glu Glu Ile Arg
            370                 375                 380

Gly Ala Gly Ser Asn Ala Asp Ala Leu Ala Gly Phe Ala Lys Gln Leu
385                 390                 395                 400

Ser Asp Glu Arg Arg Thr Arg Leu Gly Arg Arg Val Gly Ala Gly
                405                 410                 415

Arg Leu Lys Ser Arg Arg
            420

<210> SEQ ID NO 29
<211> LENGTH: 423
<212> TYPE: PRT
<213> ORGANISM: Brachypodium distachyon

<400> SEQUENCE: 29

Met Ala Ser Tyr Ala Cys Arg Arg Pro Cys Glu Ser Cys Arg Thr Arg
1               5                   10                  15

Ala Met Ala Gly Val Val Gly Glu Pro Thr Thr Pro Gly Gln Arg
            20                  25                  30

Val Thr Val Leu Thr Ile Asp Gly Gly Ile Arg Gly Leu Ile Pro
            35                  40                  45

Gly Thr Ile Leu Ala Phe Leu Glu Asp Arg Leu Gln Glu Leu Asp Gly
        50                  55                  60

Pro Asp Ala Arg Leu Ala Asp Tyr Phe Asp Cys Ile Ala Gly Thr Ser
65                  70                  75                  80

Thr Gly Gly Leu Ile Thr Ala Met Ile Thr Ala Pro Gly Glu Glu Gly
                85                  90                  95

Arg Pro Leu Phe Ala Ala Glu Asp Ile Asn Arg Phe Tyr Leu Asp Asn
            100                 105                 110

Gly Pro Gln Ile Phe Pro Gln Lys Arg Ser Ser Leu Met Ser Val Leu
        115                 120                 125

Ala Ser Leu Thr Arg Pro Arg Tyr Asn Gly Lys Phe Leu His Gly Lys
130                 135                 140

Ile Arg Ser Met Leu Gly Glu Thr Arg Val Cys Asp Thr Leu Thr Asp
145                 150                 155                 160

Val Val Ile Pro Thr Phe Asp Val Arg Leu Leu Gln Pro Ile Ile Phe
                165                 170                 175

Ser Thr Tyr Asp Ala Lys Ser Met Pro Leu Lys Asn Ala Leu Leu Ser
            180                 185                 190

Asp Val Cys Ile Ser Thr Ser Ala Ala Pro Thr Phe Leu Pro Ala His
        195                 200                 205

Tyr Phe Gln Thr Glu Asp Asp Asn Gly Lys Val Arg Glu Tyr Asn Leu
    210                 215                 220

Ile Asp Gly Gly Val Ala Ala Asn Asn Pro Thr Met Val Ala Met Thr
225                 230                 235                 240

Gln Ile Thr Lys Lys Ile Met Ala Lys Asp Lys Glu Glu Leu Tyr Pro
                245                 250                 255

Val Lys Pro Ser Asp Cys Gly Lys Phe Leu Val Leu Ser Ile Gly Thr
            260                 265                 270

Gly Ser Thr Ser Asp Gln Gly Leu Tyr Thr Ala Lys Gln Cys Ser Arg
            275                 280                 285

Trp Gly Ile Ile Arg Trp Leu Arg Asn Lys Gly Met Ala Pro Ile Ile
290                 295                 300

Asp Ile Phe Met Ala Ala Ser Ser Asp Leu Val Asp Ile His Ala Ala
305                 310                 315                 320

Val Leu Phe Gln Ser Leu His Ser Asp Gly Asp Cys Tyr Leu Arg Ile
                325                 330                 335

Gln Asp Asn Ser Leu Arg Gly Ala Ala Thr Val Asp Thr Ala Thr
            340                 345                 350

Pro Asp Asn Met Arg Glu Leu Val Arg Ile Gly Glu Arg Met Leu Ala
            355                 360                 365

Gln Arg Val Ser Lys Val Asn Val Glu Thr Gly Arg Tyr Glu Glu Met
370                 375                 380

Gln Gly Ala Gly Thr Asn Ala Asp Ala Leu Ala Gly Phe Ala Arg Gln
385                 390                 395                 400

Leu Ser Asp Glu Arg Arg Ala Arg Phe Gly Pro Arg Asp Gly Ala Pro
                405                 410                 415

Ala Asn Gly Lys Ser Arg Cys
            420

<210> SEQ ID NO 30
<211> LENGTH: 437
<212> TYPE: PRT
<213> ORGANISM: Sorghum bicolor

<400> SEQUENCE: 30

Met Ala Thr Tyr Tyr Ser Ser Arg Arg Pro Cys Asn Ala Cys Ser Thr
1               5                   10                  15

Lys Ala Met Ala Gly Ser Val Val Gly Glu Pro Val Val Leu Gly Gln
            20                  25                  30

Arg Val Thr Val Leu Thr Val Asp Gly Gly Ile Arg Gly Leu Ile
            35                  40                  45

Pro Gly Thr Ile Leu Ala Phe Leu Glu Ala Arg Leu Gln Glu Leu Asp
50                  55                  60

Gly Pro Glu Val Arg Leu Ala Asp Tyr Phe Asp Tyr Ile Ala Gly Thr
65                  70                  75                  80

Ser Thr Gly Gly Leu Ile Thr Ala Met Leu Thr Ala Pro Gly Lys Asp
                85                  90                  95

Arg Arg Pro Leu Tyr Ala Ala Lys Asp Ile Asn Gln Phe Tyr Met Glu
            100                 105                 110

Asn Cys Pro Arg Ile Phe Pro Gln Lys Ser Ser Arg Leu Ala Ala Ala
            115                 120                 125

Met Ser Ala Leu Arg Lys Pro Arg Tyr Asn Gly Lys Cys Leu Arg Asn
130                 135                 140

Leu Ile Met Ser Met Leu Gly Glu Thr Arg Val Ser Asp Thr Leu Thr
145                 150                 155                 160

Asn Val Ile Ile Pro Thr Phe Asp Val Arg Leu Leu Gln Pro Ile Ile
                165                 170                 175

Phe Ser Thr Tyr Asp Ala Lys Ser Met Pro Leu Lys Asn Ala Leu Leu
            180                 185                 190

Ser Asp Val Cys Ile Gly Thr Ser Ala Ala Pro Thr Tyr Leu Pro Ala
            195                 200                 205

His Tyr Phe Gln Thr Lys Asp Ala Gly Ser Gly Lys Glu Arg Glu Tyr
            210                 215                 220

```
Asn Leu Ile Asp Gly Gly Val Ala Ala Asn Asn Pro Thr Met Val Ala
225                 230                 235                 240

Met Thr Gln Ile Thr Lys Lys Met Leu Ala Ser Lys Glu Lys Ala Glu
            245                 250                 255

Glu Leu Tyr Pro Val Lys Pro Trp Asn Cys Arg Lys Phe Leu Val Leu
        260                 265                 270

Ser Ile Gly Thr Gly Ser Thr Ser Glu Gln Gly Leu Tyr Thr Ala Arg
    275                 280                 285

Gln Cys Ser Arg Trp Gly Ile Cys Arg Trp Ile Arg Asn Asn Gly Met
290                 295                 300

Ala Pro Ile Ile Asp Ile Phe Met Ala Ala Ser Ser Asp Leu Val Asp
305                 310                 315                 320

Ile His Val Ala Ala Met Phe Gln Ser Leu His Ser Asp Gly Asp Tyr
                325                 330                 335

Leu Arg Ile Gln Asp Asn Ser Leu His Gly Ala Ala Ala Thr Val Asp
            340                 345                 350

Ala Ala Thr Pro Glu Asn Met Arg Thr Leu Val Gly Ile Gly Glu Arg
        355                 360                 365

Met Leu Ala Gln Arg Val Ser Arg Val Asn Val Glu Thr Gly Arg Tyr
370                 375                 380

Glu Pro Val Pro Gly Glu Gly Ser Asn Ala Asp Ala Leu Ala Gly Ile
385                 390                 395                 400

Ala Arg Gln Leu Ser Glu Arg Arg Thr Arg Leu Ala Arg Arg Thr
                405                 410                 415

Ser Ala Ile Val Ser Ser Gly Gly Ala Ser Arg Arg Thr Cys Ala Ser
            420                 425                 430

Lys Val Ser Asn Val
        435

<210> SEQ ID NO 31
<211> LENGTH: 429
<212> TYPE: PRT
<213> ORGANISM: Panicum virgatum

<400> SEQUENCE: 31

Met Ala Ser Tyr Ser Ser Arg Arg Pro Cys Ser Val Cys Arg Thr Lys
1               5                   10                  15

Ala Met Ala Gly Ser Val Val Gly Glu Pro Val Pro Gly Gln Arg
            20                  25                  30

Val Thr Val Leu Thr Ile Asp Gly Gly Ile Arg Gly Leu Ile Pro
            35                  40                  45

Gly Thr Ile Leu Ala Phe Leu Glu Ala Arg Leu Gln Glu Gln Asp Gly
    50                  55                  60

Pro Glu Ala Arg Leu Ala Asp Tyr Phe Asp Cys Ile Ala Gly Thr Ser
65                  70                  75                  80

Thr Gly Gly Leu Ile Thr Ser Met Ile Thr Thr Pro Gly Glu Asp Lys
                85                  90                  95

Arg Pro Leu Phe Ala Ala Arg Asp Ile Asn Arg Phe Tyr Phe Asp Asn
            100                 105                 110

Cys Pro Arg Ile Phe Pro Gln Ser Arg Ser Ser Leu Ala Ala Ala Met
        115                 120                 125

Leu Ala Leu Arg Lys Pro Arg Tyr Ser Gly Lys Tyr Leu Arg Ser Thr
    130                 135                 140

Ile Arg Ser Met Leu Gly Glu Thr Arg Val Ser Asp Thr Leu Thr Asn
145                 150                 155                 160
```

Val Val Ile Pro Thr Phe Asp Ile Lys Leu Leu Gln Pro Ile Ile Phe
            165                 170                 175

Ser Thr Tyr Asp Ala Arg Ser Thr Pro Leu Lys Asn Ala Leu Leu Ser
            180                 185                 190

Asp Val Cys Ile Ser Thr Ser Ala Ala Pro Thr Tyr Leu Pro Ala His
            195                 200                 205

Tyr Phe Lys Thr Gln Asp Ala Gly Gly Lys Ala Arg Glu Tyr Asn Leu
            210                 215                 220

Ile Asp Gly Gly Val Ala Ala Asn Asn Pro Thr Met Val Ala Met Thr
225                 230                 235                 240

Gln Ile Ile Lys Lys Met Leu Gly Lys Asp Lys Glu Glu Leu Phe Pro
            245                 250                 255

Val Arg Pro Ala Asp Cys Arg Lys Phe Leu Val Leu Ser Ile Gly Thr
            260                 265                 270

Gly Ser Ala Ser Asp Glu Gly Leu Phe Thr Ala Arg Gln Cys Ser Arg
            275                 280                 285

Trp Gly Val Val Arg Trp Leu Arg Asn Lys Gly Met Ala Pro Ile Ile
            290                 295                 300

Asp Ile Phe Met Ala Ala Ser Ser Asp Leu Val Asp Ile His Ala Gly
305                 310                 315                 320

Val Leu Phe Gln Ser Leu His Ser Asp Arg Asp Tyr Leu Arg Ile Gln
            325                 330                 335

Asp Ser Ser Leu Arg Gly Ala Ala Thr Val Asp Ala Ala Thr Pro
            340                 345                 350

Glu Asn Met Arg Thr Leu Val Gly Ile Gly Glu Arg Met Leu Ala Gln
            355                 360                 365

Arg Val Ser Arg Val Asn Val Glu Thr Gly Arg Asn Glu Pro Val Pro
            370                 375                 380

Gly Glu Gly Ser Asn Ala Asp Ala Leu Ala Gly Leu Ala Arg Gln Leu
385                 390                 395                 400

Ser Glu Glu Arg Arg Thr Arg Leu Ala Arg Arg Ala Ala Gly Ala
            405                 410                 415

Ala Gly Gly Ser Arg Cys Cys Ser Pro Val Lys Leu Tyr
            420                 425

<210> SEQ ID NO 32
<211> LENGTH: 428
<212> TYPE: PRT
<213> ORGANISM: Panicum virgatum

<400> SEQUENCE: 32

Met Ala Ser Tyr Ser Ser Arg Arg Pro Cys Ser Val Cys Arg Thr Lys
1               5                   10                  15

Ala Met Ala Arg Ser Val Val Gly Glu Pro Val Pro Gly Gln Arg
            20                  25                  30

Val Thr Val Leu Thr Ile Asp Gly Gly Gly Ile Arg Gly Leu Ile Pro
            35                  40                  45

Gly Thr Ile Leu Ala Phe Leu Glu Ala Arg Leu Gln Glu Leu Asp Gly
        50                  55                  60

Pro Glu Ala Arg Leu Ala Asp Tyr Phe Asp Cys Val Ala Gly Thr Ser
65                  70                  75                  80

Thr Gly Gly Leu Ile Thr Ser Met Ile Thr Thr Pro Gly Glu Asp Lys
            85                  90                  95

Arg Pro Leu Phe Ala Ala Arg Asp Ile Asn Arg Phe Tyr Phe Asp Asn
            100                 105                 110

```
Cys Pro Arg Ile Phe Pro Gln Ser Arg Ser Leu Ala Ala Met
            115                 120                 125

Ser Ala Leu Arg Lys Pro Arg Tyr Arg Gly Lys Tyr Leu Arg Thr Thr
130                 135                 140

Ile Arg Ser Met Leu Gly Glu Thr Arg Val Ser Asp Thr Leu Thr Asn
145                 150                 155                 160

Val Val Ile Pro Thr Phe Asp Ile Lys Leu Leu Gln Pro Ile Ile Phe
                165                 170                 175

Ser Thr Tyr Asp Ala Arg Ser Thr Pro Leu Lys Asn Ala Leu Leu Ser
            180                 185                 190

Asp Val Cys Ile Ser Thr Ser Ala Ala Pro Thr Tyr Leu Pro Ala His
                195                 200                 205

Tyr Phe Gln Thr Gln Asp Thr Gly Gly Lys Val Arg Glu Tyr Asn Leu
            210                 215                 220

Ile Asp Gly Gly Val Ala Ala Asn Asn Pro Thr Met Val Ala Met Thr
225                 230                 235                 240

Gln Ile Ile Lys Lys Met Leu Gly Lys Asp Arg Glu Glu Leu Phe Pro
                245                 250                 255

Val Arg Pro Ala Asp Cys Arg Lys Phe Leu Val Leu Ser Ile Gly Thr
            260                 265                 270

Gly Ser Ala Ser Asp Glu Gly Leu Phe Thr Ala Arg Gln Cys Ser Arg
            275                 280                 285

Trp Gly Val Val Arg Trp Leu Arg Asn Lys Gly Met Ala Pro Ile Ile
            290                 295                 300

Asp Ile Phe Met Ala Ala Ser Ala Asp Leu Val Asp Ile His Ala Ala
305                 310                 315                 320

Ala Leu Phe Gln Ser Leu His Ser Asp Arg Asp Tyr Leu Arg Ile Gln
                325                 330                 335

Asp Ser Ser Leu Arg Gly Ala Ala Thr Val Asp Ala Ala Thr Pro
            340                 345                 350

Glu Asn Met Arg Ala Leu Val Gly Ile Gly Glu Arg Met Leu Ala Gln
            355                 360                 365

Arg Val Ser Arg Val Asn Val Glu Thr Gly Arg Asn Glu Pro Val Pro
370                 375                 380

Gly Glu Gly Ser Asn Ala Asp Ala Leu Ala Gly Leu Ala Arg Gln Leu
385                 390                 395                 400

Ser Glu Glu Arg Arg Thr Arg Leu Ala Arg Ala Ala Ala Gly Cys
            405                 410                 415

Ala Gly Gly Ser Thr Cys Cys Ser Pro Val Lys Thr
            420                 425

<210> SEQ ID NO 33
<211> LENGTH: 421
<212> TYPE: PRT
<213> ORGANISM: Setaria italica

<400> SEQUENCE: 33

Met Ala Ser Tyr Ser Ser Arg Arg Pro Cys Asn Ala Cys Arg Thr Lys
1               5                   10                  15

Ala Met Ala Gly Ser Val Val Gly Glu Pro Val Pro Gly Gln Arg
                20                  25                  30

Val Thr Val Leu Thr Ile Asp Gly Gly Ile Arg Gly Leu Ile Pro
                35                  40                  45

Gly Thr Ile Leu Ala Phe Leu Glu Ala Arg Leu Gln Glu Leu Asp Gly
            50                  55                  60
```

```
Pro Glu Ala Arg Leu Ala Asp Tyr Phe Asp Cys Ile Ala Gly Thr Ser
 65                  70                  75                  80

Thr Gly Gly Leu Ile Thr Ala Met Ile Thr Pro Gly Glu Asp Lys
             85                  90                  95

Arg Pro Leu Phe Ala Ala Arg Asp Ile Asn Arg Phe Tyr Phe Asp Asn
            100                 105                 110

Cys Pro Arg Ile Phe Pro Gln Ser Arg Ser Leu Ala Ala Ala Met
        115                 120                 125

Ser Ala Leu Arg Lys Pro Arg Tyr Asn Gly Lys Tyr Leu Arg Ser Thr
130                 135                 140

Ile Arg Ser Met Leu Gly Glu Thr Arg Val Ser Asp Ala Leu Thr Asn
145                 150                 155                 160

Val Val Ile Pro Thr Phe Asp Ile Lys Leu Ile Gln Pro Ile Ile Phe
                165                 170                 175

Ser Thr Tyr Asp Val Lys Asn Met Pro Leu Lys Asn Ala Leu Leu Ser
            180                 185                 190

Asp Val Cys Ile Ser Thr Ser Ala Ala Pro Thr Tyr Leu Pro Ala His
        195                 200                 205

Tyr Phe Gln Ile Gln Asp Ala Gly Gly Lys Thr Arg Glu Tyr Asn Leu
210                 215                 220

Ile Asp Gly Gly Val Ala Ala Asn Asn Pro Thr Met Val Ala Met Thr
225                 230                 235                 240

Gln Ile Thr Lys Met Met Leu Ala Lys Asp Lys Glu Glu Leu Tyr Pro
                245                 250                 255

Val Lys Pro Glu Asp Cys Arg Lys Phe Leu Val Leu Ser Ile Gly Thr
            260                 265                 270

Gly Ser Thr Ser Asp Glu Gly Leu Phe Thr Ala Arg Gln Cys Ser Arg
        275                 280                 285

Trp Gly Val Val Arg Trp Leu Arg Asn Asn Gly Met Ala Pro Ile Ile
290                 295                 300

Asp Ile Phe Met Ala Ala Ser Ser Asp Leu Val Asp Ile His Ala Ala
305                 310                 315                 320

Val Leu Phe Gln Ser Leu His Ser Asp Gly His Ser Leu Arg Gly Ala
                325                 330                 335

Ala Ala Thr Val Asp Ala Ala Thr Pro Glu Asn Met Arg Thr Leu Val
            340                 345                 350

Gly Ile Gly Glu Arg Met Leu Ala Gln Arg Val Ser Arg Val Asn Val
        355                 360                 365

Glu Thr Gly Arg Tyr Glu Pro Val Pro Gly Gly Ser Asn Ala Asp
370                 375                 380

Ala Leu Val Ala Leu Ala Arg Gln Leu Ser Asp Glu Arg Ala Arg
385                 390                 395                 400

Ile Ala Arg Arg Ala Ala Ala Cys Ala Gly Gly Ser Arg Cys Cys
                405                 410                 415

Ser Pro Val Lys Thr
            420

<210> SEQ ID NO 34
<211> LENGTH: 432
<212> TYPE: PRT
<213> ORGANISM: Oryza sativa
```

<400> SEQUENCE: 34

```
Met Ala Ala Ser Tyr Ser Cys Arg Arg Thr Cys Glu Ala Cys Ser Thr
1               5                   10                  15

Arg Ala Met Ala Gly Cys Val Val Gly Glu Pro Ala Ser Ala Pro Gly
            20                  25                  30

Gln Arg Val Thr Leu Leu Ala Ile Asp Gly Gly Ile Arg Gly Leu
        35                  40                  45

Ile Pro Gly Thr Ile Leu Ala Phe Leu Glu Ala Arg Leu Gln Glu Leu
    50                  55                  60

Asp Gly Pro Asp Ala Arg Leu Ala Asp Tyr Phe Asp Cys Ile Ala Gly
65                  70                  75                  80

Thr Ser Thr Gly Gly Leu Ile Thr Ala Met Leu Ala Ala Pro Gly Asp
                85                  90                  95

His Gly Arg Pro Leu Phe Ala Ala Ser Asp Ile Asn Arg Phe Tyr Leu
            100                 105                 110

Asp Asn Gly Pro Leu Ile Phe Pro Gln Lys Arg Cys Gly Met Ala Ala
        115                 120                 125

Ala Met Ala Ala Leu Thr Arg Pro Arg Tyr Asn Gly Lys Tyr Leu Gln
130                 135                 140

Gly Lys Ile Arg Lys Met Leu Gly Glu Thr Arg Val Arg Asp Thr Leu
145                 150                 155                 160

Thr Asn Val Val Ile Pro Thr Phe Asp Val Arg Leu Leu Gln Pro Thr
                165                 170                 175

Ile Phe Ser Thr Tyr Asp Ala Lys Ser Met Pro Leu Lys Asn Ala Leu
            180                 185                 190

Leu Ser Asp Ile Cys Ile Ser Thr Ser Ala Ala Pro Thr Tyr Leu Pro
        195                 200                 205

Ala His Cys Phe Gln Thr Thr Asp Asp Ala Thr Gly Lys Val Arg Glu
210                 215                 220

Phe Asp Leu Ile Asp Gly Gly Val Ala Ala Asn Asn Pro Thr Met Val
225                 230                 235                 240

Ala Met Thr Gln Ile Thr Lys Lys Ile Met Val Lys Asp Lys Glu Glu
                245                 250                 255

Leu Tyr Pro Val Lys Pro Ser Asp Cys Gly Lys Phe Leu Val Leu Ser
            260                 265                 270

Val Gly Thr Gly Ser Thr Ser Asp Gln Gly Met Tyr Thr Ala Arg Gln
        275                 280                 285

Cys Ser Arg Trp Gly Ile Val Arg Trp Leu Arg Asn Lys Gly Met Ala
290                 295                 300

Pro Ile Ile Asp Ile Phe Met Ala Ala Ser Ser Asp Leu Val Asp Ile
305                 310                 315                 320

His Ala Ala Val Met Phe Gln Ser Leu His Ser Asp Gly Asp Tyr Leu
                325                 330                 335

Arg Ile Gln Asp Asn Thr Leu His Gly Asp Ala Ala Thr Val Asp Ala
            340                 345                 350

Ala Thr Arg Asp Asn Met Arg Ala Leu Val Gly Ile Gly Glu Arg Met
        355                 360                 365

Leu Ala Gln Arg Val Ser Arg Val Asn Val Glu Thr Gly Arg Tyr Val
370                 375                 380

Glu Val Pro Gly Ala Gly Ser Asn Ala Asp Ala Leu Arg Gly Phe Ala
385                 390                 395                 400
```

```
          Arg Gln Leu Ser Glu Glu Arg Arg Ala Arg Leu Gly Arg Arg Asn Ala
                          405                 410                 415

Cys Gly Gly Gly Gly Glu Gly Glu Pro Ser Gly Val Ala Cys Lys Arg
                      420                 425                 430

<210> SEQ ID NO 35
<211> LENGTH: 1269
<212> TYPE: DNA
<213> ORGANISM: Hordeum vulgare

<400> SEQUENCE: 35
atggcaagct actggtgccg gcgaccgtgc gagtcgtgca gcacgagggc gatggcgggc      60
agcgtggtcg gccagccggt ggcgccgggg cagagggtga cggtgctgac catcgacggg     120
ggcggcatcc gcggcctcat cccgggcacc atcctcgcct tcctcgaggc caggctgcag     180
gagctggacg ggcggacgc gcgcctggcc gactacttcg actgcatcgc cggcaccagc      240
accggcgggc tcatcaccgc catgctcacc gcgcccggcc aggacggccg cccgctcttc     300
gccgccaagg acgtcaaccg cttctacctc gacaacgggc cctacatctt cccccaaagg     360
aggtgcgcgc tcgccgcggt gaccgcgtcg ctgaggcggc cgaggtacag cggcaagtac     420
ctgcacggca agatcaggag catgctgggc gagacgaggc tgtgcgacgc gctcaccgac     480
gtcgtcatcc ccaccttcga cgtcaagctt ctccagccca tcatcttctc cacatacgac     540
gccaggaaca tgccctgaa gaacgcgcgg cttgccgaca tctgcatcgg cacctccgcc      600
gccccgacct acctcccggc gcaccacttc acacccaag acgacaacgg taaggagcgc      660
gagtacaacc tcatcgacgg cggcgtcgcc gccaacaatc cgacgatggt gaccatgacg     720
cagatcacca agaagatgat ggtcaaggac agggaggagc tgtacccggt gaagccgtcg     780
gactgcggca agttcctggt gctgtccatc gggaccggct cgacgtcgga ccaggggctg     840
tacacggcca gcagtgctc ccagtggggc atcatccgct ggctgcgcaa caagggcatg      900
gcgcccatca tcgacatctt catggcgccc agctccgacc tcgtcgacat ccacgccgcc     960
gtgctcttcc agtcgctgca gcgacggt aactacctcc gcatccagga caactcgctc      1020
cacgccccag ccgcgacggt ggacgccgcc acgcccgaga acatggcgga gctcctcagg     1080
atcggcgagc ggatgttggc acagagggtg tccagggtga acgtcgagac cgggaggtac     1140
gaggagatac ggggcgccgg gagcaacgcc gacgcgctcg ccggcttcgc caaacagctc     1200
tccgacgaga ggaggacaag gctcggccgc cggcgcgttg gcgccggccg tctgaaatcc     1260
agacgctga                                                             1269

<210> SEQ ID NO 36
<211> LENGTH: 1286
<212> TYPE: DNA
<213> ORGANISM: Brachypodium distachyon

<400> SEQUENCE: 36
atggcgagct acgcgtgccg gcggccgtgc gagtcctgcc gcacgagggc gatggcgggc      60
ggcgtggtgg gcgagccgac gacgccgggg cagagggtga cggtgctgac catcgacggg     120
ggcggcatcc ggggcctcat cccgggcacc atcctcgcct tcctcgagga caggctccag     180
gagctggacg ggcggacgc gaggctggcg gactacttcg attgcatagc cggcacgagc      240
accggcgggc tcatcaccgg catgatcacc gcgcccggcg aggagggcg cccgctcttc      300 gccgccgagg acatcaaccg cttctacctc gacaacgggc cgcaaatctt ccccaaaag      360 aggagctcgc tgatgtcggt gctggcgtcg ctgacgcggc cgaggtacaa cggcaagttc     420
```

```
ctgcatggca agatcaggag catgctgggc gagacgaggg tgtgcgacac gctcacggac      480
gtcgtcatcc ccaccttcga cgtcaggctc ctccagccca tcatcttctc cacctacgac      540
gccaagagca tgcccctgaa gaacgcgctg ctctccgacg tgtgcatcag tacgtccgcc      600
gccccgacct ttctccccgc gcactacttc cagaccgaag acgacaacgg caaggtgcgc      660
gagtacaacc tcatcgacgg cggtgtcgcc gccaacaatc cgacgatggt tgccatgact      720
cagatcacca agaagataat ggccaaggac aaggaggagc tgtacccggt gaagccgtcg      780
gactgcggca agttcctggt gctgtccatc gggacgggtt cgacgtccga ccaggggctg      840
tacacggcga agcagtgctc ccggtggggc atcatccggt ggctccggaa caagggcatg      900
gcgccaatca tcgacatctt catggccgcc agctccgacc tcgtggacat ccacgccgcc      960
gtgctcttcc agtcgctgca cagcgacggc gactgctacc tccgcatcca ggacaactcg     1020
ctccggggcg ccgccgccac ggtggacacg gccacgccgg acaacatgag ggagctcgtc     1080
aggatcggcg agaggatgct ggcgcagcgg gtgtccaagg tcaacgtgga gaccgggcgc     1140
tacgaggaga tgcagggcgc cgggaccaac gccgacgcgc tagcgggctt cgccaggcag     1200
ctgtctgacg agaggagggc caggttcggc ccacgggacg gcgcgccggc gaatggcaaa     1260
tcaagatgct gatcttcttc ttgtaa                                          1286

<210> SEQ ID NO 37
<211> LENGTH: 1314
<212> TYPE: DNA
<213> ORGANISM: Sorghum bicolor

<400> SEQUENCE: 37
atggcgacct actactcttc gcggcgtcca tgcaacgcct gcagcacgaa ggcgatggcc       60
gggagcgtgg tcggcgagcc cgtcgtgctg gggcagaggg tgacggtgct gacggtggac      120
ggcggcggca tccgtggtct catccccgga accatccttg ccttcctcga ggcccggctg      180
caggagctgg acgggccgga ggttaggctc gcggactact tcgactacat cgccgggacg      240
agcaccggcg ggctcatcac cgccatgctc accgcgcccg gcaaggacag gcggcctctc      300
tacgctgcca aggacatcaa ccaattctac atggagaatt gccctcgcat cttccctcaa      360
aagagcagca ggcttgcggc cgccatgtcc gcgctgagga agccaaggta caacggcaag      420
tgcctccgta acctgatcat gagcatgctc ggcgagacga gggtgagcga cacgctcacc      480
aacgtcatca tccctaccct tcgacgtcagg ctgctgcagc ccatcatctt ctccacctac      540
gacgccaaga gcatgcctct gaagaacgcg ctgctctccg acgtgtgcat cggcacgtcc      600
gccgcgccga cctacctccc ggcgcactac ttccagacca aggacgccgg cagtggcaag      660
gaacgcgagt acaacctcat cgacggcggt gtcgccgcca acaatccgac gatggttgcg      720
atgacgcaga tcaccaagaa gatgcttgcc agcaaggaga aggccgagga gctgtaccca      780
gtgaagccgt ggaactgccg caagttcctg gtgctgtcca tcgggacggg tcgacgtcg       840 gagcagggcc tgtacacggc gcggcagtgc tcgcggtggg gcatctgccg gtggatccgg      900
aacaacggca tggccccccat catcgacatc ttcatggcgg cgagctcgga cctggtggac      960
atccacgtcg ccgcgatgtt ccagtcgctc cacagcgacg gcgactacct cgcatccag       1020 gacaactcgc tgcacggcgc cgcggccacc gtggacgcgg cgacgccgga gaacatgcgg     1080
acgctcgtcg ggatcgggga gcggatgctg gcgcagcggg tgtccagggt caacgtggag     1140
acagggaggt acgaaccggt gcctggggaa ggaagcaacg ctgatgcgct cgctgggatc     1200
```

| | |
|---|---:|
| gcaaggcagc tctcggagga gaggaggaca aggctcgcgc gccgcacctc cgccatcgtc | 1260 |
| agctccggtg gtgcctctag acgtacgtgt gcctcaaagg tctccaatgt ctaa | 1314 |

<210> SEQ ID NO 38
<211> LENGTH: 1290
<212> TYPE: DNA
<213> ORGANISM: Panicum virgatum

<400> SEQUENCE: 38

| | |
|---|---:|
| atggcgagct actcgtcccg gcgtccatgc agcgtctgca gaacgaaggc gatggctggg | 60 |
| agcgtggtcg gcgagccggt ggtgccgggg cagagggtga cggtgttgac catcgacggc | 120 |
| ggcggcatcc gggggctcat ccccggcacc atcctcgcct tcctggaggc gaggctgcag | 180 |
| gagcaggacg ggccggaggc caggctggcg gactacttcg actgcatcgc cggcacgagc | 240 |
| accggcgggc tcatcaccctc catgatcacc acgcccggcg aggacaagcg gccgctcttc | 300 |
| gccgccaggg acatcaaccg cttctacttc gacaactgcc cgcgcatctt ccctcagagt | 360 |
| aggagcagcc tcgcggcggc gatgttggcg ctgaggaagc caaggtacag cggcaagtac | 420 |
| ctgcgcagca cgatccggag catgctcggc gagacgaggg tgtccgacac gctgaccaac | 480 |
| gtcgtcatcc ccaccttcga catcaagctg ctccagccca tcatcttctc cacctacgac | 540 |
| gccaggagca cgccgctgaa gaacgcgctg ctctccgacg tgtgcatcag cacgtccgcg | 600 |
| gcgccgacct acctcccggc gcactacttc aagacccaag acgcaggcgg caaggcccgc | 660 |
| gagtacaacc tcatcgacgg cggtgtcgcc gccaacaacc cgacgatggt cgcgatgacg | 720 |
| cagatcatca agaagatgct gggcaaggac aaggaggagc tgttcccggt gaggccagcg | 780 |
| gactgccgca agttcctggt gctgtcgatc gggacggggt cggcgtccga cgagggcctc | 840 |
| ttcacggcgc ggcagtgctc ccggtggggc gtcgtccgtt ggctccggaa caagggcatg | 900 |
| gcgcccatca tcgacatctt catggcggcc agctcggacc tcgtggacat ccacgccggc | 960 |
| gtgctgttcc agtcgctcca cagcgaccgc gactacctcc gcatccagga cagctcgctc | 1020 |
| cgcggcgccg cggcgaccgt ggacgccgcc acgccggaga acatgcgcac gctcgtgggg | 1080 |
| atcggggagc ggatgctggc gcagcgggtg tcgagggtga acgtggagac cgggaggaac | 1140 |
| gagccggtgc ccggggaagg gagcaacgcc gacgcgctcg ccgggctggc caggcagctc | 1200 |
| tccgaggaga ggcggacgcg gctcgcgcgc gcgccgccg ccggcgcagc cggcggctcc | 1260 |
| agatgctgct cccctgttaa attatactag | 1290 |

<210> SEQ ID NO 39
<211> LENGTH: 1287
<212> TYPE: DNA
<213> ORGANISM: Panicum virgatum

<400> SEQUENCE: 39

| | |
|---|---:|
| atggcgagct actcgtcccg gcgcccatgc agcgtctgca gaacgaaggc gatggccagg | 60 |
| agcgtggtcg gcgagccggt ggtgccgggg cagagggtga cggtgctgac catcgacggc | 120 |
| ggcggcatcc gggggctaat ccccggcacc atcctcgcct tcctggaggc caggctgcag | 180 |
| gagctggacg ggccggaggc caggctagcg gactacttcg actgcgtcgc cggcacgagc | 240 |
| accggcgggc tcatcaccctc gatgatcacc accccggcg aggacaagcg gccgctcttc | 300 |
| gctgccaggg acatcaaccg cttctacttt gacaactgcc cgcgcatctt ccctcagagt | 360 |
| aggagcagcc tcgcggcggc gatgtcgcg ctgaggaagc caaggtacag aggcaagtac | 420 |
| ctgcgcacca cgatccggag catgctcggg gagacgaggg tgtcggacac gctgaccaac | 480 |

```
gtcgtcatcc ccaccttcga catcaagctg ctccagccca tcatcttctc cacctacgac    540
gccaggagca cgccgctgaa gaacgcgctg ctctccgacg tgtgcatcag cacgtccgcc    600
gcgccgacct acctcccggc gcactacttc cagacccaag acaccggcgg caaggtccgc    660
gagtacaacc tcatcgacgg cggtgtcgcc gccaacaacc cgacgatggt cgcgatgacg    720
cagatcatca agaagatgct gggcaaggac agggaggagt tgttcccggt gaggccggcg    780
gactgccgca agttcctggt gctgtcgatc gggacggggt cggcgtccga cgagggcctc    840
ttcacggcac ggcagtgctc ccggtggggc gtcgtccggt ggctccgcaa caagggcatg    900
gcgcccatca tcgacatctt catggcggcc agcgccgacc tcgtggacat ccacgccgcc    960
gcgctgttcc agtcgctcca cagcgaccgc gactacctcc gcatccagga cagctcgctg   1020
cgcggcgccg cggcgaccgt ggacgccgcc acgccggaga acatgcgggc gctcgtgggg   1080
atcggggagc ggatgctggc gcagcgggtg tcgagggtca cgtggagac cgggaggaac   1140 gagccggtgc ccggggaagg gagcaacgcc gacgcgctcg ccgggctggc caggcagctc   1200
tccgaggaga ggcggacgcg gctcgcgcgc gcgccgccg ccggctgcgc cggcggctcc    1260
acatgctgct cccctgttaa aacatag                                       1287

<210> SEQ ID NO 40
<211> LENGTH: 1266
<212> TYPE: DNA
<213> ORGANISM: Setaria italica

<400> SEQUENCE: 40
atggcgagct actcgtcccg gcggccctgc aacgcatgca gaacgaaggc gatggccggg     60
agcgtggtcg gcgagccggt ggtgccgggg cagagggtga cggtgctgac catcgacggt    120
ggcggcatcc gggggctcat ccccggcacc atcctggcgt tcctggaggc caggctgcag    180
gagctggacg gccggaggc gaggctggcg gactacttcg actgcatcgc cggcacgagc    240
accggcgggc tcatcaccgc catgatcacc acgcccggcg aggacaagcg cccgctcttc    300
gccgccaggg acatcaaccg cttctacttc gacaactgcc cgcgcatctt ccctcaaagt    360
aggagcagtc ttgcggcggc gatgtcgcg ctgaggaagc caaggtacaa cggcaagtac    420
ctgcgcagca cgatcaggag catgctcggc gagacgaggg tgagcgacgc gctgaccaac    480
gtcgtcatcc ccaccttcga catcaagctg atccagccca tcatcttctc cacctacgac    540
gtcaagaaca tgccactgaa gaacgcgctg ctctccgacg tgtgcatcag cacgtccgcc    600
gcaccgacct acctcccggc gcactacttc cagatccaag acgccggcgg caagactcgc    660
gagtacaacc tcatcgacgg cggtgtcgcc gccaacaacc cgacgatggt cgcgatgacg    720
cagatcacca agatgatgct ggccaaggac aaggaggagc tgtacccggt gaagccggag    780
gactgccgca agttcctggt cctgtcgatc gggacggggt cgacgtccga cgagggcctc    840
ttcacggcgc ggcagtgctc ccggtggggc gtcgtccggt ggctccgcaa caacggcatg    900
gcgcccatca tcgacatctt catggcggcc agctcggacc tcgtcgacat ccacgccgcc    960
gtgctgttcc agtcgctcca cagcgacgga cactcgctcc gcggcgccgc cgcgaccgtc   1020
gacgccgcca cgcctgagaa catgcggacg ctcgtcggga tcggggagcg gatgctggcg   1080
cagcgggtgt cgagggtcaa cgtggagaca gggaggtacg agccggtgcc cggggaaggg   1140
agcaacgccg acgcgctcgt cgcgctcgcg aggcagctct ccgacgagag gagggcgcgg   1200
atcgcgcgcc gcgcagccgc cgcatgcgcc ggcggctcca gatgctgctc ccctgtcaaa   1260
acttag                                                              1266
```

<210> SEQ ID NO 41
<211> LENGTH: 1299
<212> TYPE: DNA
<213> ORGANISM: Oryza sativa

<400> SEQUENCE: 41

```
atggcggcga gctactcgtg ccggcggaca tgcgaggcgt gcagcacgag ggcgatggcc      60
gggtgcgtgg tgggcgagcc ggcgtcggcg ccggggcagc gggtgacgtt gctggcgatc     120
gacggcggcg gcatcagggg cctcatcccg ggcaccatcc tcgccttcct cgaggccagg     180
ctgcaggagc tggatggccc cgacgcgcgc ctcgccgatt acttcgactg catcgccggg     240
accagcaccg gcggcctcat caccgccatg ctcgccgcgc ccggcgacca cggccgcccg     300
ctcttcgccg ccagcgacat caaccgcttc tacctcgaca cggcccact catcttccca      360
caaaagaggt gcggcatggc ggcggccatg gcggcgctga cgaggccgag gtacaacggc     420
aagtacctgc aggggaagat caggaagatg ctgggcgaga cgagggtgcg cgacacgctg     480
acgaacgtcg tcatccccac gttcgacgtc aggctgctcc agccaaccat cttctccaca     540
tacgacgcga gagcatgcc gctcaagaac gcgctcctct ccgacatctg catcagcaca      600
tccgcggcgc cgacctacct ccccgcgcac tgcttccaga ccaccgacga cgccaccggc     660
aaggtccgcg agttcgacct catcgacggc ggcgtcgccg ccaacaaccc gacgatggtg     720
gccatgacgc agatcaccaa gaagataatg gtgaaggaca aggaggagct gtacccggta     780
aagccgtcgg actgcggtaa gttcctggtg ctgtccgtgg caccgggtc gacgtcggac      840
caggggatgt acacggcgag gcagtgctcg cggtgggggga tcgtccggtg gctgcgcaac     900
aaggggatgg cgcccatcat cgacatcttc atggcggcca gctccgacct cgtcgacatc     960
cacgccgccg tcatgttcca gtcgctgcac agcgacggcg actacctccg catccaggac    1020
aacacgctcc acggcgacgc cgccacggtg gacgccgcca caggacaa catgcgggcg      1080
ctcgtcggga tcggcgagcg gatgctggcg cagcgggtgt cgagggtcaa cgtcgagacc    1140
ggcaggtacg tcgaggtgcc cggcgccggc agcaacgccg acgcgctgag gggcttcgcc    1200
aggcagctct ccgaggagag gagggcgagg ctaggtcggc gaaacgcctg cggcggcggc    1260
ggcgaaggag agcccagcgg cgtggcgtgc aagcgttag                          1299
```

<210> SEQ ID NO 42
<211> LENGTH: 150
<212> TYPE: DNA
<213> ORGANISM: maize
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t

<400> SEQUENCE: 42

```
gcggacgctc gtcgggatcg gggagcggat gctggcacag ngggtgtcca gggtcaacgt      60
ggagacaggg aggtacgaac cggtgacngg ngaaggaagc aatgccgatg ccctcggtgg     120
gctcgctagg cagctctccg aggagaggag                                     150
```

```
<210> SEQ ID NO 43
<211> LENGTH: 23
<212> TYPE: DNA
<213> ORGANISM: Artificial Sequence
<220> FEATURE:
<223> OTHER INFORMATION: primer

<400> SEQUENCE: 43
gagggcatcg gcattgcttc ctt                                              23

<210> SEQ ID NO 44
<211> LENGTH: 21
<212> TYPE: DNA
<213> ORGANISM: Artificial Sequence
<220> FEATURE:
<223> OTHER INFORMATION: primer

<400> SEQUENCE: 44
gtcaacgtgg agacagggag c                                                21

<210> SEQ ID NO 45
<211> LENGTH: 21
<212> TYPE: DNA
<213> ORGANISM: Artificial Sequence
<220> FEATURE:
<223> OTHER INFORMATION: primer

<400> SEQUENCE: 45
gtcaacgtgg agacagggag g                                                21

<210> SEQ ID NO 46
<211> LENGTH: 53
<212> TYPE: DNA
<213> ORGANISM: Artificial Sequence
<220> FEATURE:
<223> OTHER INFORMATION: Primer

<400> SEQUENCE: 46
ggggacaact ttgtatagaa aagttgcttc aaaatggtta tgcgtaggtt gaa             53

<210> SEQ ID NO 47
<211> LENGTH: 45
<212> TYPE: DNA
<213> ORGANISM: Artificial Sequence
<220> FEATURE:
<223> OTHER INFORMATION: Primer

<400> SEQUENCE: 47
ggggactgct tttttgtaca aacttgctgc cgccttcgac aacac                      45

<210> SEQ ID NO 48
<211> LENGTH: 50
<212> TYPE: DNA
<213> ORGANISM: Artificial Sequence
<220> FEATURE:
<223> OTHER INFORMATION: Primer

<400> SEQUENCE: 48
ggggacaact ttgtatagaa aagttgcttt taggataagc cagagtttgt                 50

<210> SEQ ID NO 49
<211> LENGTH: 45
<212> TYPE: DNA
<213> ORGANISM: Artificial Sequence
<220> FEATURE:
<223> OTHER INFORMATION: Primer
```

<400> SEQUENCE: 49

```
ggggactgct tttttgtaca aacttgctgc cgccttcgac cgcac          45
```

<210> SEQ ID NO 50
<211> LENGTH: 2657
<212> TYPE: DNA
<213> ORGANISM: maize

<400> SEQUENCE: 50

```
tcaaaatggt tatgcgtagg ttgaagaaaa gttgggagtt tacaaaataa tacaatggga    60
tgcctgttct atcatctaac ttaagccatg tatcaaggtt gcaagttaca taaaatacgc   120
ttatattctg atggttggaa ccacacattc tacacgtttc ccaaaacaat gaaaaggta    180
gttgtcgaaa gatttaagca tctaaagtgt ccactctctc tgagagcatc aaaataaagt   240
agtacgtctt atgtttaaa ctatttattg aagtaccaaa ctatacggct actaaagatt   300
tatttagatg agtaaacgaa ataatttatg gtatataaat taagaagggg tgattagtca   360
tgaaaaataa aatgtcacaa ttaccagcag cacgtgattt tctaaataat ttaagcatgt   420
gcggtgctct tccagataaa acttagggga cgaccaccta gttcattgaa agaggggaat   480
aaaccaagct ccaactttca agcttgtcaa ggcttgtcat tattaattta aacaggacag   540
ccaattctca gacatgatgt tccaaactgc taatgaatat ataatgctca aaataaacaa   600
ctaggttctt aactgtcaat tacacccaca agatgcacat aattagaaaa ggtaaaagag   660
aaggcaaatg gaataccagg aattatatga ctactaaatc atttatttag ataagtagat   720
gaaataattt atggtacata atataagaac gggtgattag ttatgagaaa taaaaggtca   780
ccattaccag cagcatgtgt tgttctaaat aatttaagcc tgtgtggtat tctttgagat   840
aaaacatagg agacgaccac ctaattcatt ggaagagggg aacagacgaa gctccaacct   900
tcgagcttgt caaggcttgg cattattaat ttaaacagga cagacaatgc tcaatctgaa   960
ctgccattgt atctacaata ctcaaaataa acaactagat tctgaacaac cagattattt   1020
gtactcattc catgtctcat aaacaaggaa aaaataacaa ccagattatt tgtactcatt   1080
ccatgtctca taactttgg gcaccatcca tccaacacat ccaatctaaa cacaccaaac   1140
gatggggaat ggaaagagca gtattcgatt caacaatggc aaacaaatat cactgaatta   1200
gaccaagaat aaacctaatt agacaacgac ctcccaacca tcattcgtca ggctgtaaag   1260
aagataaagc tgccatgggg catggatcaa gcagaacacc agagatgaat ccaaacacac   1320
agaaaatcac gcgcgctgtc tacaatgaca acaagcccca catttcattg cagtacactg   1380
ggctacaaag gcacgtacaa caaagagcta gggaaacatt gcggagggca cgagagagca   1440
gctaacttga caatatagca gactgagctt gcactgttag caggcgagga agggaatcat   1500
ggggacggag aatggggtcc atgcccgcga aggagaaggc ggacgccgcc acggtggcac   1560
cggcgcacgc gcacacaggg aacccgcaca ggcagccatg gatgctgcct cgccattgcg   1620
ccggtcgtct ctgccacgct cctctctctc tcccgctgca tcgccgtgga tggggcaagc   1680
agagagcagg gactgcgacg atctgggcgg aggactcgcc ttggagagcg cggacgcaga   1740
cgggattcta gggagagagc gaagacgggg cgcgcgcggc gctcgcgcgg cgtggtggcg   1800
gcgagattag cggggtggg gggagggcgg agccgtggtg agggtgtgga cgccctcctt   1860
accctcttaa gtagtagtag agatataatc cgttccaaaa tatccatccg ttcaatttat   1920
atttcgtttg atctttttac cctaaatttg attgactcat cttattaaaa aagttcataa   1980
ctattattaa tctttattga gatatcattt agcatataat atactttaag tgtggttta    2040
```

```
gattttttt   aaaaaaaaaa  attcgcaaaa  attaaatgaa  acgacccaat  caaacttgaa    2100
aagtaaaact  aattataaat  ttgaacggaa  ggagtaagag  gatgtttgaa  tgtactagag    2160
ctaatagttg  gttgctttaa  aatttgctag  tagaattagc  tagctaataa  atatctagat    2220
aactattagc  taatttgcta  aaacagctaa  tagttgaact  attagctaga  ttgtttggat    2280
gtattcggct  aattttaatg  gctaactatt  agctatagta  caatattcaa  acacctccta    2340
attaaaatgg  acaaatatct  cttcttttgg  tcccttgcgt  tagattttc   atatctcctt    2400 atttagtata  aaagaatcat  caaaaagtgg  acaaccccta  gtggaacacc  attttagtag    2460
tggttgcatg  aaacctttcg  cgcaccagtt  tctatgtgtc  actctaaaaa  tgggacagca    2520
tgtacgtagt  gcctatatat  atacaagtca  tctatcgttg  cctcctcagt  tcatcactaa    2580
tcacacttat  tgtgccctcg  acgagtatct  atagctagct  cattaatcga  ttcggggtg    2640 tgttgtcgaa  ggcggca                                                      2657

<210> SEQ ID NO 51
<211> LENGTH: 2534
<212> TYPE: DNA
<213> ORGANISM: maize

<400> SEQUENCE: 51
tttaggataa  gccagagttt  gtgccggtta  ctcttgatgt  tcaacaacac  caagatggct      60
tggtggtaat  taagagcttg  gtgatctctc  agtggtgctc  gtgagagtcc  caactcattg     120
tgtaataaaa  gattataggt  gattcaccat  gccggagtgg  tgaataatca  acccgtagag     180
agcattgagt  ccttgaatgg  atcgatgggg  ggctacaccc  ttgtgtgggt  caagtcagag     240
ttttagcagt  tcttgcaccc  atgatctcat  cgtgaagcat  agataaattt  aaattctttt     300
gaattattta  tatatgacaa  cactattcgt  cgctctaggt  gactatcacc  taccctaaaa     360
tgacttaaca  aatcttttatt  aattgttaag  tcattcacat  ttttgttaat  ccactccaaa     420
gtcagggtgt  ttagtgtttt  tacatccatg  tctccttaga  ctcacggtgt  ctctcccaga     480
ttctctctca  ccctcacctc  tctctcacta  gccactaggg  aacgcaacac  ccatcgatgg     540
ctcttcgccc  catgaaacgt  tcacacaatc  gcaattgtcg  aggcatgcat  ggctgggaga     600
gcagacatgg  aggcatacgt  gctagggttg  cacatgggca  agagggtggg  tgtggctatt     660
cagatatgca  tggtgagcaa  gatgggtgag  gttgtgggca  tgatgagggg  ataaggaaga     720
ataagatctc  ttttgttagg  ctgtctccag  cagctatcgt  atcccattcc  ctatcgcatc     780
ccctatttta  aactttacta  tgcaaacaat  gtaatatata  gtgcagattc  cctattttac     840
acaatgtgtt  gtagacaacc  ttggagctct  tgcataaaag  ctctagtttt  ggctctagct     900
cctctgagaa  acaatcccc   accatgtttt  taggaagaat  ccctgaaggg  cacccattt     960 ggttggaaat  acatctcctc  ctacaggatt  atgtttgact  tttttttgca  atgtgggacc    1020
cacaggggag  aggaggacga  gaaggaaccg  gagagcctat  tttttgggct  cctggcttcg    1080
cttggtttct  aggggcggct  ccttcctatt  ttcacaaagg  agctagtaga  ggagcctccc    1140
atttcatgat  ttttttgaagg  atctatttaa  ggagccttga  aagagcccta  ccaaggtagg    1200
cctagaaata  ataaggagg   aaaaagagaa  ggtatcacaa  cttttgtcta  caacgtgaaa    1260
atgtttggct  aaatagataa  aacagtttga  attttatcga  ttcaattgtt  tattgagggc    1320
atgtttggga  gggctttagt  tctagcttct  ttcgcgaaaa  atccagagcc  ctacaaaatg    1380
acgtttggta  aaacgacttc  ttccgaaaaa  cacccaaaaa  cccaagatat  tttatactac    1440
gaaggaaagg  tcacacatcc  tagttagctt  cactggttct  agctccttcc  aattttgcaa    1500
```

```
aaaagtcaca aaggataagc catttttca aatgatttgt gaaatgccta cgctaaaaag    1560
tctacttttc caaaaaaact agagctagag ccgttttgg caagtcagaa ccctaccaaa    1620
tagtccctca gtttaagcaa agtgaggcta tactgaagct aaattatgcc aaattgggcc    1680
tacatctcca tattttcaac caaatgcttt agggtttctt gtaatcgaca tgatttgttt    1740
cttcataaat agtatatgga ccgctccaaa atactccatc cgtttcaatt tatattacgt    1800
ttgatctttt taccctaaat ttgatcgact cgtcttatta aaaagttca taactattaa    1860 taatctttac tgtgatatca tttagcatat aatatacttt aagtgtagct ttgattttt    1920 tttgcaaaaa ttaaatgaaa cgacccaatc aaacttgata aaaaagtaaa actaattata    1980
aatttggaca taaggagtag gagggtgttt gaatacacta gagttaatag ttagttgtct    2040
taaaatttgc tagtacaatt agctagctaa caaatattta ggtaactatt agctaatttg    2100
ctaaaaacag ctaatagttg aactattagt tgaactatta gctagactgt ttggatgtat    2160
tcaactaatt ttagcagcta actattagtt atagtataat attcaaacac ctcctaatta    2220
aaatggacaa atatctattc ccttggtccc ttgcgttaga tttccatat atcctcattt    2280 agtataaaaa gaatcatcaa aaagtggaca acccctagtg gaacaccatt ttagtagtgg    2340
ttgcatgaaa cctttcgcgc atcagttact atgtgtcact ctaaaaatgg ggcagcatgt    2400
acgcagtgcc tatatttata caaggcatct atcgttgcct cctcagttca tcactaatca    2460
cacttattgt gccctcgacg agtatctagc tagctcatta atcgatcaat cggggtgtgc    2520
ggtcgaaggc ggca                                                    2534

<210> SEQ ID NO 52
<211> LENGTH: 28
<212> TYPE: DNA
<213> ORGANISM: Artificial Sequence
<220> FEATURE:
<223> OTHER INFORMATION: Primer

<400> SEQUENCE: 52
caccatggcg agctactcgt cgcggcgt                                       28

<210> SEQ ID NO 53
<211> LENGTH: 25
<212> TYPE: DNA
<213> ORGANISM: Artificial Sequence
<220> FEATURE:
<223> OTHER INFORMATION: Primer

<400> SEQUENCE: 53
gatatcgtac gacgcacatc tagag                                          25

<210> SEQ ID NO 54
<211> LENGTH: 19
<212> TYPE: DNA
<213> ORGANISM: Artificial Sequence
<220> FEATURE:
<223> OTHER INFORMATION: Primer

<400> SEQUENCE: 54
gcgagcccac cgagggcat                                                 19
```

POLYNUCLEOTIDE RESPONSIBLE OF HAPLOID INDUCTION IN MAIZE PLANTS AND RELATED PROCESSES

The present invention concerns an isolated polynucleotide responsible of haploid induction in maize plants and related processes. Additionally, the invention relates to plants that have been genetically transformed with the polynucleotide of the invention. The invention also relates to a process for screening a mutant plant population for enhanced haploid induction. The invention further relates to molecular markers associated with haploid induction in maize plants and their use for allele identification during the production of inducer lines.

The establishment of homozygous lines is a fundamental practice in selection and breeding. One of the major constraints in the establishment of homozygous lines is the long time (usually 8-10 generations) needed for obtaining individuals with a high level of homozygosity.

Doubled haploids represent a major breeding tool (Geiger et al., Doubled haploids in hybrid maize breedings, Maydica, 54(4): 485-499, 2009 and Röber et al., In vivo haploid induction in maize—Performance of new inducers and significance of doubled haploid lines in hybrid breeding, Maydica, 50(3-4): 275-283, 2005). It allows the rapid production of an homozygous line in fewer generations than traditional methods, can be used to benefit of a maximum genetic variance in breeding programs and to accelerate the stacking of genes in a recurrent line.

"Gynogenesis" (development of the non-fertilized ovule into a haploid plant) combined with chromosome doubling is a key step for maize selection. This first step is conducted by crossing the plant with an inducer line. During the past years, works have been done to develop said inducer lines. The inducer line PK6 was developed by the INRA of Clermont-Ferrand (WO 2005/004586) and comes from the publicly available stock 6 (Coe 1959). Few other inducer lines are available but all come from the same origin stock 6 (Weber et al., Today's Use of Haploids in Corn Plant Breeding, Advances In Agronomy, 123: 123-144, 2014).

Improvement of the inducing ability has thus been achieved during the past years but the need to improve this ability still exists. In addition, the availability of molecular markers to follow the induction locus or loci is of interest.

A major QTL (quantitative trait locus) responsible of haploid inducing has been identified on chromosome 1 (bin 1.4) and some minor QTL on others chromosomes (Deimling et al., Methodology and genetics of in vivo haploid induction in maize, 38: 203-224, 1997 and Prigge et al., Doubled Haploids in Tropical Maize: I. Effects of Inducers and Source Germplasm on in vivo Haploid Induction Rates. Crop Science, 51(4): 1498-1506, 2012). Fine mapping of the QTL on chromosome 1 was started by Barret et al. (Barret et al., A major locus expressed in the male gametophyte with incomplete penetrance is responsible for in situ gynogenesis in maize, Theoretical And Applied Genetics, 117(4): 581-594, 2008) with the PK6 inducer line and the QTL ggi1 (gynogenesis inducer 1) was localized between the markers umc 1917 and bnlg 1811 (Barret et al., 2008, FIG. 2) in a 11.6 cM interval. The authors of this work concluded that a more precise cloning was not possible in their particular population because of the wild type standard deviation (percentage of haploid production obtained by crossing non inducer lines) and the heterofertilization (when egg and central cell are fertilized by independent pollen grains).

A more precise cloning of the chromosome 1 QTL of inducer line UH400 (Prigge et al., New insights into the genetics of in vivo induction of maternal haploids, the backbone of doubled haploid technology in maize, Genetics, 190(2): 781-793, 2011), qhir1, was then achieved by Dong et al. (Dong et al., Fine mapping of qhir1 influencing in vivo haploid induction in maize. Theoretical And Applied Genetics, 126(7): 1713-1720, 2013). This QTL is located between markers X291 and X263, with a distance between these markers of 243 Kb.

Another fine mapping of the region sed1 (segregation distortion 1) was achieved by Xu et al. (Xu et al., Gametophytic and zygotic selection leads to segregation distortion through in vivo induction of a maternal haploid in maize. Journal Of Experimental Botany, 64(4): 1083-1096, 2013), and narrowed the QTL to a 450 kb region, between markers X22 and X96.

However, these fine mapping approaches did not identify the gene or precise DNA region responsible for this major QTL on chromosome 1.

In addition, the identification of new informative molecular markers for the inducing capacity of maize lines is still needed to improve the breeding of new inducer lines. Phenotypic markers are currently used to distinguish haploid from diploids plants. They present some drawbacks such as their expression, which depends on their genetic background and which is not usable for all genetics. Moreover, current inducer lines are more appropriate to temperate germplasm and there is still a need to develop inducer lines adapted to other agronomical regions. Besides, multiplication of inducer lines is critical as, due to poor pollen efficiency of these lines, pollination by foreign material is frequent. As a consequence, seed lots for inducer lines or hybrids need to be regularly controlled for purity. As for both applications, breeding of new lines and seed multiplication of available inducer lines, controls need to be done by an induction step and the sowing of thousands of seeds, the use of informative molecular markers should drastically reduce the time and means needed. As a consequence, the currently used methods have the disadvantage of being long and expensive in equipment. The identification of new reliable markers for an easier, faster and cheaper method is needed.

The inventors of the present invention identified a gene unexpectedly homologous to the acyl transferase/acyl hydrolase/lysophospholipase family as being responsible for haploid induction in maize, as well as molecular markers thereof, opening the way to the understanding and improvement of the induction mechanism in maize.

Described herein are polynucleotides and related processes (methods) directed to haploid induction in maize plants. Said polynucleotides are novel polynucleotides that induce haploid maize plants. Specifically, described herein are polynucleotides having the nucleic acid sequence set forth in SEQ ID NO: 1 or SEQ ID NO: 3, and fragments thereof. SEQ ID NO: 1 corresponds to the gDNA sequence of the candidate gene responsible of haploid induction in maize plants that has been identified by the inventors and being homologous to the acyl transferase/acyl hydrolase/lysophospholipase family. The sequence identified by the inventors has been mutated by the insertion of the 4 bp CGAG in exon 4 of the gene in comparison with the wild type sequence of the gene which is found in maize. SEQ ID NO: 3 corresponds to the cDNA sequence of the candidate gene of SEQ ID No 1.

The present invention thus relates to an isolated polynucleotide responsible of haploid induction in plants comprising or consisting of:

(a) a nucleotide sequence which comprises or consists in SEQ ID No 1 or 3;

(b) a nucleotide sequence at least 80% identical to the nucleotide sequence of (a) and which is responsible of haploid induction in maize plants; or (c) a complementary sequence of the nucleotide sequence of (a) or (b), wherein the complementary sequence and the nucleotide sequence consist of the same number of nucleotides and are 100% complementary.

By "responsible of haploid induction in maize plants" is meant the in situ formation of haploid offspring at a significantly higher frequency than what is observed in natural populations of maize.

By "haploid" is meant a character related to cells or plants or parts of plants comprising such cells whose chromosomes contained in their nucleus are each in only one copy (n).

Such polynucleotides can easily be obtained by the man skilled in the art. The polynucleotides according to the invention can for example be obtained by cloning the candidate gene or cDNA using suitable primers. The polynucleotide can then be cloned into a vector, preferably into an expression vector.

"Isolated polynucleotide" refers herein to both RNA and DNA, including cDNA, genomic DNA, and synthetic DNA. Polynucleotides can have any three-dimensional structure. A polynucleotide can be double-stranded or single-stranded (i.e., a sense strand or an antisense strand). Non-limiting examples of polynucleotides include genes, gene fragments, exons, introns, messenger RNA (mRNA), transfer RNA (tRNA), ribosomal RNA, siRNA, micro-RNA, ribozymes, cDNA, recombinant polynucleotides, and branched polynucleotides. A polynucleotide may contain unconventional or modified nucleotides. Isolated polynucleotides according to the invention may be purified or recombinant.

The polynucleotides according to the invention may be of any length, e.g. at least, at most and/or about 20, 25, 30, 35, 50, 100, 250, 500 or 1000 nucleotides long.

"gDNA" or genomic deoxyribonucleic acid is chromosomal DNA, in contrast to extrachromosomal DNAs like plasmids, genomic DNA represent the polynucleotide as present in the cell comprising exons and intron sequences.

"cDNA" or complementary DNA is DNA synthesized from a messenger RNA (mRNA) template in a reaction catalyzed by the enzyme reverse transcriptase.

The term "isolated" in reference to a biological component (such as a nucleic acid, a vector or a protein) refers to a biological component that has been substantially separated or purified away from other biological components of the cell of the organism, or the organism itself, in which the component naturally occurs, such as other chromosomal and extra-chromosomal DNA and RNA, proteins, cells, and organelles. "Isolated nucleic acids" or "isolated vectors" include nucleic acid molecules purified by standard purification methods. These terms also encompass nucleic acids and vectors prepared by amplification and/or cloning, as well as chemically synthesized nucleic acids and vectors.

By "a nucleotide sequence at least 80% identical to the nucleotide sequence of (a)" is meant in particular, a nucleotide sequence 81, 82, 85, 90, 91, 92, 93, 94, 95, 96, 97, 98 or 99% identical to the nucleotide sequence of (a). For example, a nucleotide sequence 95% "identical" to a query sequence of the present invention, is intended to mean that the sequence of the polynucleotide is identical to the query sequence except that the sequence may include up to five nucleotide alterations per each 100 nucleotides of the query sequence. In other words, to obtain a polynucleotide having a sequence at least 95% identical to a query sequence, up to 5% (5 of 100) of the nucleotides of the sequence may be inserted, deleted, or substituted with another nucleotide. In other terms, the sequences should be compared on their entire length (i.e. by preparing a global alignment). For example, a first polynucleotide of 100 nt (nucleotides) that is comprised within a second polynucleotide of 200 nt is 50% identical to said second polynucleotide. The needle program, which uses the Needleman-Wunsch global alignment algorithm (Needleman and Wunsch, 1970, A general method applicable to the search for similarities in the amino acid sequence of two proteins, J. Mol. Biol. 48:443-453) to find the optimum alignment (including gaps) of two sequences when considering their entire length, may for example be used. Preferably, the percentage of identity in accordance with the invention is calculated using the needle program with a "Gap open" parameter equal to 10.0, a "Gap Extend" parameter equal to 0.5, and a Blosum 62 matrix. The needle program is for example available on the ebi-.ac.uk World Wide Web site.

In one embodiment, the nucleotide sequence at least 80% identical to the nucleotide sequence of (a) and which is responsible of haploid induction in maize plants may be a genomic sequence of maize origin comprising some allelic variations. Allelic variations may be nucleotide differences without consequence to the transcribed amino acid sequence or with consequences to the amino acid sequence but with a conservation of the protein function in maize haploid induction.

A "complementary sequence" as used herein refers to a sequence that specifically hybridizes in solution, e.g., according to Watson-Crick base pairing rules.

By "fragment" is meant a number of nucleotides sufficient to provide for a specific hybridization to the nucleic acid comprising or consisting of the complementary sequence of one of the SEQ ID Nos 1 and 3. In particular, the fragment of nucleic acid comprises at least 20 nucleotides, more particularly at least 150 nucleotides.

The present invention also relates to a vector comprising the recombinant DNA construct according to the invention.

The vector is preferably an isolated vector.

A "vector" may be such a construct that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant sequences under the transcriptional control of 5' and 3' regulatory sequences and a dominant selectable marker. 5' and 3' regulatory sequences comprise but are not limited to a promoter regulatory region (e.g., a regulatory region controlling inducible or constitutive, environmentally or developmentally-regulated, or cell- or tissue-specific expression), transcription initiation start site, ribosome binding site, RNA processing signal, transcription termination site, and polyadenylation signal.

By "plasmid", it is herein meant a double-stranded circular DNA. The plasmid may include a marker gene enabling to select the cells comprising said plasmid, an origin of replication to allow the cell to replicate the plasmid and/or a multiple cloning site allowing the insertion of a DNA fragment, in particular the polynucleotide according to the invention.

In particular, said plasmid is chosen from L1457, L1465, L1478, L1482, L1479, L1483, L1542, L1543, L1540, L1541.

In particular, the vectors according to the invention can be chosen from vectors pSB11 (Ishida et al., (1996).), pBIOS898 (Biogemma, for sense construct), pBIOS895 (Biogemma, for RNAi construct), pBb7m34GW, pBb7m42GW7 (Karimi et al., 2012), pDONR221 (Invitrogen).

The vector preferably comprises an expression cassette of the polynucleotide according to the invention, i.e. a nucleic acid corresponding to the polynucleotide according to the invention placed under the control of at least one expression signal allowing its expression.

The expression signal is particularly selected among a promoter, a terminator, an enhancer and their combinations.

Suitable promoters, terminators and enhancers are well-known by the skilled person.

In particular, the promoter may be a constitutive promoter selected in the group consisting of the rice actin promoter (Act1) and intron (McElroy et al., 1990, Plant Cell, 2:163-171), the ubiquitin promoter of maize (Christensen et al., 1996, Transgenic. Res., 5:213) or the CsVMV promoter (Verdaguer et al., 1998, Plant Mol Biol. 6:1129-39) and $FAD_2$ intron (patent application WO 2006/003186 from Biogemma). Other examples of constitutive promoters useful for expression include the 35S promoter, the 19S promoter (Kay et al., 1987, Science, 236:1299-1302), or the pCRV promoter (Depigny-This et al., 1992, Plant Molecular Biology, 20:467-479).

In a preferred embodiment, said construct is under the control of a constitutive promoter. In a most preferred embodiment, said construct is an RNAi construct, under the control of a constitutive promoter. Other suitable promoters could be used. It could be a tissue-specific promoter, for example a pollen-specific promoter, a promoter active in both anther and pollen, or an inducible promoter.

For example, the terminator may be selected in the group consisting of the Nos terminator corresponding to the region in the non coding 3' region of the nopaline synthase gene of the Ti-plasmid of *Agrobacterium tumefaciens* nopaline strain (Depicker et al. 1992) or the AtSac66 terminator. Others possible terminators are the polyA 35S terminator of the cauliflower mosaic virus (CaMV), described in the article of Franck et al., (1980) or the histone terminator (EP 0 633 317).

Any other element like introns, enhancers, transit peptides, etc . . . may be comprised in the expression cassette. Introns and enhancers may be used to improve the expression of the gene according to the present invention.

Among useful introns, the first intron of maize adh1S can be placed between the promoter and the coding sequence. This intron when included in a gene construct increased the expression of the desired protein in maize cells (Callis et al., 1987). One also can use the $1^{st}$ intron of the shrunken 1 gene of the maize (Maas et al., 1991), the $1^{st}$ intron of the catalase gene of the bean catalase (CAT-1) (Ohta et al., 1990), the $2^{nd}$ intron of the ST-LS1 gene of potato (Vancanneyt et al. 1990), the DSV intron of the yellow dwarf virus of tobacco (Morris et al., 1992), the actin-1 intron (act-1) of rice (McElroy et al., 1990) and intron 1 of triosephosphate isomerase (TPI) (Snowdon et al., 1996).

The expression cassettes may additionally contain 5' leader sequences. Such leader sequences can act to enhance translation. Such 5' leaders are known in the art and include, but are not limited to, picornavirus leaders, for example, the EMCV leader (Encephalomyocarditis 5' noncoding region) (Elroy-Stein, Fuerest, and Moss B., 1989); potyvirus leaders, for example, the TEV leader (Tobacco etch Virus) (Allison et al., 1986); the human immunoglobulin heavy-chain binding protein leader (BiP) (Macejack and Sarnow, 1991); the untranslated leader from the coat protein mRNA of alfalfa mosaic virus (AMV RNA 4) (Jobling and Gehrke, 1987); the tobacco mosaic virus leader (TMV) (Gallie et al., 1989); and the maize chlorotic mottle virus leader (MCMV) (Lommel et al., 1991). See also, Della-Cioppa et al. (1987). Other methods known to enhance translation can be utilized, for example introns, and the like.

In one embodiment of the invention, the vector is a pSB11 vector with a Basta resistance cassette comprising an Actin promoter and intron, a Bar gene and a Nos terminator, a GFP cassette comprising a CsVMV promoter and $FAD_2$ intron, a GFP gene and a Nos terminator and a nucleotide sequence which comprises or consists in SEQ ID No 1 or 3; a nucleotide sequence at least 80% identical to the nucleotide sequence of (a) and which is responsible of haploid induction in maize plants as herein defined; or a complementary sequence of the nucleotide sequence of (a) or (b), wherein the complementary sequence and the nucleotide sequence consist of the same number of nucleotides and are 100% complementary, in particular a nucleotide sequence which comprises or consists in SEQ ID No 1 or 3 as herein defined, more particularly under the control of the rice actin promoter and first intron and followed by the AtSac66 terminator.

Isolated polynucleotides of the invention can be incorporated into recombinant DNA constructs capable of introduction into and replication in a host cell.

The present invention thus relates to a recombinant DNA construct comprising the polynucleotide according to the invention operably linked to at least one regulatory sequence.

The terms "recombinant construct," "expression cassette," "expression construct," "chimeric construct," "construct," "recombinant DNA construct" and "recombinant DNA fragment" are used interchangeably herein and are nucleic acid fragments. A recombinant construct comprises an artificial combination of nucleic acid fragments, including, and not limited to, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such construct may be used by itself or may be used in conjunction with a vector as herein defined. If a vector is used then the choice of vector is dependent upon the method that will be used to transform host cells as is well known to those skilled in the art. For example, a plasmid vector, as described above, can be used. The skilled artisan is well aware of the genetic elements that must be present on the vector in order to successfully transform, select and propagate host cells comprising any of the isolated polynucleotide according to the invention.

The term "recombinant DNA construct" refers to a DNA construct assembled from nucleic acid fragments obtained from different sources. The types and origins of the nucleic acid fragments may be very diverse.

The expression cassette will include 5' and 3' regulatory sequences operably linked to a polynucleotide according to the invention. "Operably linked" is intended to mean a functional linkage between two or more elements. "Regulatory sequences" refer to nucleotides located upstream (5' non-coding sequences), within, or down-stream (3' non-coding sequences) of a coding sequence, and which may influence the transcription, RNA processing, stability, or translation of the associated coding sequence. Regulatory sequences may include, and are not limited to, promoters, translation leader sequences, introns, and polyadenylation recognition sequences.

In particular, said regulatory sequence (a promoter, for example) is responsible for an expression of the polynucleotide according to the invention.

The expression cassette may additionally contain selectable marker genes.

The expression cassette is further described as previously mentioned above.

The regulatory regions (i.e., promoters, transcriptional regulatory regions, and translational termination regions) and/or the polynucleotide according to the invention may be native/analogous to the host cell or to each other. Alternatively, the regulatory regions and/or the polynucleotide according to the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

A number of promoters can be used, as mentioned above. In particular, as previously mentioned, the promoter may be a constitutive promoter selected in the group consisting of the rice actin promoter (Act1) and intron, the maize ubiquitin promoter or the CsVMV promoter, the 35S promoter, the 19S promoter, the pCRV promoter and $FAD_2$ intron.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In particular, the DNA construct according to the invention comprises a polynucleotide which comprises or consists in a nucleotide sequence of SEQ ID No 1 or 3 operably linked to a promoter, in particular to the Actin promoter and intron.

As previously mentioned, the gene identified by the inventors as being responsible for haploid induction in maize is a mutant form of the wild type gene. The consequence of said mutation is a frame shift leading to 20 non conserved amino acids followed by a premature STOP codon downstream of the mutation. This would mean that the modification of function of the wild type gene of SEQ ID No 2 or 4 found in maize would induce haploid maize plants.

As a consequence, in the scope of the present invention, is also a recombinant DNA construct, comprising:

(a) a fragment of the polynucleotide according to the invention or of a polynucleotide comprising or consisting in the nucleotide sequence of SEQ ID No 2 or 4 or of a nucleotide sequence at least 80% identical to said nucleotide sequence of SEQ ID No 2 or 4; and (b) the complementary sequence thereof;

said fragment and complementary sequence thereof being transcribed in an hairpin RNA to induce RNA interference.

By "fragment" is meant a number of nucleotides sufficient to provide for a specific hybridization to the nucleic acid comprising or consisting of the complementary sequence of one of the SEQ ID Nos 1 to 4. In particular, the fragment of nucleic acid comprises at least 20 nucleotides, more particularly at least 150 nucleotides.

"Stringent conditions" can be easily defined by the man skilled in the art using common knowledge. If necessary, guidance for defining such conditions can be found in numerous textbooks, such as Molecular Cloning: A Laboratory Manual by Sambrook et al., 2000. In particular, stringent conditions according to the invention can be constituted using a hybridization reaction requiring an optimized combination of hybridization buffer and hybridization temperature, depending on the ingredients of the hybridization buffer. Such determination of hybridization conditions falls within the routine work of the person skilled in the art.

As mentioned above, SEQ ID No 2 represents the wild type gene sequence (gDNA sequence) found in maize corresponding to the mutated gene of SEQ ID No 1 identified by the inventors as being responsible for haploid induction in maize. SEQ ID No 4 corresponds to the cDNA sequence of said wild type gene.

By "hairpin RNA" is meant a sequence of RNA that makes a tight hairpin turn that can be used to silence target gene expression, in the context of the invention the wild type gene of SEQ ID No 2, via RNA interference (RNAi). Expression of hairpin RNA in cells is typically accomplished by delivery of plasmids or through viral or bacterial vectors as herein mentioned.

By "RNA interference" is meant the biological process in which RNA molecules inhibit gene expression, typically endogenous gene expression by causing the destruction of specific mRNA molecules.

The polynucleotide according to the invention can be expressed as a transgene in order to make haploid inducer maize plants by overexpression of the SEQ ID No 1 or 3 or by overexpression of sequence SEQ ID No 2 or 4 by a process known as co-suppression. The DNA construct able to induce RNA interference can also be expressed in order to inhibit the expression of the endogenous wild type gene and lead to haploid inducer maize plants.

The present invention thus also relates to a process for transforming a host cell, comprising transforming the host cell with the recombinant DNA construct as defined above.

It also relates to a haploid inducer maize plant or seed comprising the recombinant DNA construct as defined above.

As used herein, the term "plant" can be a whole plant, any part thereof, or a cell or tissue culture derived from a plant. Thus, the term "plant" can refer to any of: whole plants, plant components or organs (including but not limited to embryos, pollen, ovules, seeds, leaves, flowers, branches, fruit, kernels, ears, cobs, husks, stalks, roots, root tips, anthers, and the like), plant tissues, plant cells, plant protoplasts, plant cell tissue cultures from which maize plant can be regenerated, plant callus, plant clumps, and plant seeds. A plant cell is a cell of a plant, either taken directly from a seed or plant, or derived through culture from a cell taken from a plant.

Said process and said maize plant transformation involve, and are not limited to, introducing a DNA construct into a plant or host cell. "Introducing" is intended to mean presenting to the plant the DNA construct. Processes for introducing polynucleotides into plants are known in the art including, and not limited to, stable transformation methods and transient transformation methods.

"Transformation" refers to the transfer of a nucleic acid fragment into the genome of a host organism, resulting in genetically stable inheritance. Host organisms containing the transformed nucleic acid fragments are referred to as "transgenic" organisms.

"Host cell" refers the cell into which transformation of the DNA construct takes place and may include a yeast cell, a bacterial cell, and a plant cell. Examples of methods of plant transformation include *Agrobacterium*-mediated transformation (De Blaere et al., 1987, Meth. Enzymol. 143:277), particle-accelerated or "gene gun" transformation technology (Klein et al., 1987, Nature (London) 327:70-73; U.S. Pat. No. 4,945,050) and protoplast transformation by electroporation or the use of chemicals such as PEG, among others.

"Stable transformation" is intended to mean that the polynucleotide introduced into a plant integrates into the genome of the plant and is capable of being inherited by the progeny thereof. "Transient transformation" or "transient expression" is intended to mean that the polynucleotide is introduced into the plant and does not integrate into the genome of the plant.

Suitable methods of introducing polynucleotides into plant cells are known by the man skilled in the art and include *Agrobacterium*-mediated transformation (U.S. Pat. Nos. 5,563,055 and 5,981,840, and Ishida et al., (2007). *Agrobacterium*-mediated transformation of maize. Nat Protoc 2, 1614-1621), particle bombardment (Gordon-Kamm et al., 1990, Plant Cell 2:603-618) and electroporation of protoplasts (Rhodes et al., 1988, Science 240:204-207).

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853. Briefly, the polynucleotide according to the invention can be contained in a transfer cassette flanked by two non-identical recombination sites. An appropriate recombinase is needed for the integration of the transfer cassette fragment at the target site. Others methods without recombinase have also been described in WO 90/11354 but also in WO 96/14408. Said methods start from the observation that Double Strand Break (DSB) enhances the probability of homologous recombination at a given position. Said methods have been improved by the development of Meganucleases, Zn finger nuclease and others tools like TALENs and CRISPR/Cas9 system that have been developed to obtain targeted DSB.

These tools can be used for "gene editing". The terms "gene editing" cover targeted mutations, theses mutations can be random mutation or directed mutations, by targeted is intend that the localization of the mutation is chosen. In particular, by the previously described homologous recombination system, a nucleotide exchange can be done to induce targeted mutations. Others methods for "gene editing" include the use of a DSB and a repair template to induce a specific nucleotide exchange during DNA repair. The CRISPR/Cas9 system is one of the specific methods of "gene editing" whereas the Cas9 protein and an ARN are used for obtaining a targeted DSB. Alternatively a simple DSB (double strand break) without repair template can be done on a targeted sequence to induce random mutations at this site. These mutations should be short insertions or deletions based on NHEJ (near Homologous End Joining) or MMEJ (microhomology mediated end joining).

The cells that have been transformed may be grown into plants in accordance with conventional ways. See, for example, McCormick et al. (1986) Plant Cell Reports 5:81-84.

The present invention thus also relates to process for producing haploid inducer maize plant or enhancing haploid induction ability of a maize plant comprising:

(a) transforming a maize plant cell with the recombinant DNA construct as described herein;

(b) regenerating a maize plant from the transformed maize cell; and (c) growing the transformed maize plant under conditions that are suitable for expression of the recombinant DNA construct, wherein expression of the recombinant DNA construct results in haploid induction or enhancement of haploid induction by pollen of the transformed maize plant.

Methods that combine transformation and regeneration of stably transformed plants are well known. For example, to regenerate a maize plant, transformed cells are successively cultured on shooting and rooting media prior to transfer to soil (Ishida et al., 2007, *Agrobacterium*-mediated transformation of maize. Nat Protoc 2, 1614-1621).

In one embodiment, the present invention also relates to a process for inducing haploid maize plant lines comprising:

(a) growing transformed plants by the process for producing haploid inducer maize plant or enhancing haploid induction ability of a maize plant described above;

(b) using said plants as pollinators during the crossing with a female plant; and (c) screening the progeny of the cross for haploid plants.

By "pollinators" is meant the plant that is a source of pollen for the pollination process.

By "screening the progeny of the cross", it is meant determining the percentage of haploid and diploids plants in the progeny. Genetic markers can be used for phenotyping such as for example a dominant color marker expressed in the embryo and endosperm like R1-nj (navajo) and which should be homozygous in the inducing line. When this inducer line is used with r1/r1 female plants, haploid kernels will have purple endosperm crowns and colorless embryos, diploid kernels will have purple endosperm crowns and purple embryos (Weber 2014). The screening can also be done in particular by using the molecular markers according to the invention, which are described below. "Screening the progeny of the cross", in the context of the invention also means selecting by screening of the haploid seeds, these haploid seeds being possibly further grown to produce homozygous fertile lines after their chromosome set is doubled spontaneously or by using specific protocols.

The inventors of the present invention also show, the spatial expression pattern of the gene GRMZM2G471240 by fusion of the promoters of this gene from line PK6 (SEQ ID No 1) or line B73 (SEQ No 23) with a GUS reporter gene. Based on the blue staining indicative of Gus activity, the gene has a strict gametophytic expression in pollen and in pollen tube and is not expressed in the sporophytic tissues of the anther.

The invention also concerns a nucleotide sequence which comprises or consists in:

(a) SEQ ID No. 50 (2657 bp promoter region of GRMZM2G471240 from line B73, SEQ ID No 23) or SEQ ID No 51 (2534 bp promoter region of the GRMZM2G471240 from line PK6, SEQ ID No 1), (b) a nucleotide sequence at least 75% identical to the nucleotide sequence SEQ ID No. 50 or 51, or (c) a fragment of (a) or (b) which is able to induce the specific expression of associated sequence in the pollen and/or pollen tube. By associated sequence is intend, sequence operably linked in a recombinant construct wherein the above nucleotide sequence is used as a promoter regulatory sequence and associated sequence comprises but is not limited to, the coding sequence, sequence complementary to the coding sequence, construct for RNA interference.

Pollen specific expression of a cytotoxic enzyme like barnase for example can lead to male sterile plants and are of interest for hybrid seed production.

The present invention further relates to a process for screening a mutant plant population or mutant library, for identification of a mutant plant for enhanced haploid induction, mutant termed "haploid inducer plant". Said process comprises the use of a polynucleotide according to the invention or of a polynucleotide comprising or consisting in the nucleotide sequence of SEQ ID No 2 or 4 or of a nucleotide sequence at least 80% identical to said nucleotide sequence of SEQ ID No 2 or 4. In particular, these sequences should be used for identifying an orthologous sequence.

In one embodiment, the invention thus relates to a process for identification of a mutant haploid inducer plant, said process comprising the step of identifying an orthologous sequence of the sequence consisting in:

(a) a nucleotide sequence which comprises or consists in SEQ ID No 1 or 3 or a nucleotide sequence at least 80% identical thereof and which is responsible of haploid induction in maize plants; a polynucleotide comprising or consisting in the nucleotide sequence of SEQ ID No 2 or 4 or a nucleotide sequence at least 80% identical to said nucleotide sequence of SEQ ID No 2 or 4; and/or (b) a polypeptide encoded by a polynucleotide of (a).

In particular, said process further comprises the steps of:

(2a) Screening a mutant library to identify a mutant of the orthologous sequence identified previous step (1); or (2b) generating a mutant of the orthologous sequence identified in step (1) by using a gene editing methods.

More particularly, said step (2a) comprises the use of a sequence consisting in:

(i) the orthologous sequence identified in step (1); or
(ii) a fragment thereof.

Mutant of the orthologous sequence meant mutant of polynucleotidic sequence if orthologous sequence is a polynucleotidic sequence and polynucleotidic sequence coding for the polypeptidic sequence if the orthologous sequence is a polypeptidic sequence.

In another embodiment, the invention relates to a process for identification of a mutant haploid inducer plant, said process comprising:

(a) screening a mutant library to identify a mutant of the sequence consisting in:

(i) a polynucleotide comprising or consisting in the nucleotide sequence of SEQ ID No 2 or a nucleotide sequence at least 80% identical to said nucleotide sequence of SEQ ID No 2; and/or (b) generating a mutant of the sequence of step (i) by using a gene editing methods.

In particular, process the step of screening comprises the use of a sequence consisting in:

(i) a polynucleotide according to the invention (i.e. (a) a nucleotide sequence which comprises or consists in SEQ ID No 1 or 3; a nucleotide sequence at least 80% identical to this nucleotide sequence and which is responsible of haploid induction in maize plants; or a complementary sequence thereof, wherein the complementary sequence and the nucleotide sequence consist of the same number of nucleotides and are 100% complementary); or a polynucleotide comprising or consisting in the nucleotide sequence of SEQ ID No 2 or 4 or a nucleotide sequence at least 80% identical to said nucleotide sequence of SEQ ID No 2 or 4; or (ii) a fragment thereof.

In particular, this mutant plant population or mutant library is a mutant maize plant population, sorghum plant population, or plant mutant population from others species.

Still particularly, the isolated polynucleotide responsible of haploid induction in maize plants according to the invention and described herein is used to find orthologous sequences and these orthologous sequences are used for screening other plant mutant populations.

By "orthologous sequence" is intended a gene having the same or a similar function in the same or different species. In particular, in the case or different species is meant homologous sequences that are inferred to be descended from the same ancestral sequence separated by a speciation event: when a species diverges into two separate species, the copies of a single gene in the two resulting species are said to be orthologous. In that case, orthologous genes are genes in different species that originated by vertical descent from a single gene of the last common ancestor.

When the sequence is contemplated in the same species, an orthologous sequence also meant homologous sequences that are inferred to be descended from the same ancestral sequence.

Orthologous sequences may be found by bioinformatics methods known by the man skilled in the art and the starting from the DNA sequence of the isolated polynucleotide responsible of haploid induction in maize plants according to the invention or of a polynucleotide comprising or consisting in the nucleotide sequence of SEQ ID No 2 or 4 or of a nucleotide sequence at least 80% identical to said nucleotide sequence of SEQ ID No 2 or 4 or from a polypeptide encoded by the above polynucleotides sequences (e.g., SEQ ID No 24 to SEQ ID No 25) or finally by a polypeptide sequence at least 80% identical to said polypeptidic sequences (e.g., at least 80% identical to SEQ ID No 24 or SEQ ID No 25), use of a phylogenetic tree is one of these methods.

Examples of such orthologous sequences may be, but are not limited to, polypeptides sequences of *Hordeum vulgare* (SEQ ID No 28 or SEQ ID No 35), polypeptides sequences of *Brachypodium distachyon* (SEQ ID No 29 or SEQ ID No 36), polypeptides sequences of *Sorghum bicolor* (SEQ ID No 30 or SEQ ID No 37), polypeptides sequences of *Panicum virgatum* (SEQ ID No 31, SEQ ID No 32, SEQ ID No 38 or SEQ ID No 39), polypeptides sequences of *Setaria italica* (SEQ ID No 33 or SEQ ID No 40) or polypeptides sequences of *Oryza sativa* (SEQ ID No 34 or SEQ ID No 41).

In one embodiment, the invention thus relates to a process for screening a mutant plant population for enhanced haploid induction, said process comprising the use of a polypeptide comprising or consisting in the polypeptide sequence of SEQ ID No 28, SEQ ID No 35, SEQ ID No 29, SEQ ID No 36, SEQ ID No 30, SEQ ID No 37, SEQ ID No 31, SEQ ID No 32, SEQ ID No 38, SEQ ID No 39, SEQ ID No 33, SEQ ID No 40, SEQ ID No 34 or SEQ ID No 41 or polynucleotides coding for these sequences.

The invention is also about the use of recombinant DNA comprising the orthologous sequences described herein, for transforming a host cell and obtaining a transgenic plant. In a particular construction of the recombinant DNA may comprise (a) a fragment of the orthologous sequence described herein or a nucleotide sequence at least 80% identical thereof and (b) the complementary sequence thereof, said fragment and complementary sequence thereof being transcribed in an hairpin RNA to induce RNA interference. This recombinant DNA should be used for transforming a host cell and obtaining a transgenic plant. In this specific context, orthologous sequences can also be maize or sorghum sequences with homology to the sequence of the invention.

Screening of mutants within these sequences may allow to identify plants with a modified phenotype for haploid induction.

In particular, when said screening process is done on maize or sorghum, the polynucleotide according to the invention or the polynucleotide comprising or consisting in the nucleotide sequence of SEQ ID No 2 or 4 or of a nucleotide sequence at least 80% identical to said nucleotide sequence of SEQ ID No 2 or 4 is used to screen for a mutation within said sequence. Mutations can be carried out by EMS, TILLING or eco-Tilling populations but also by T-DNA or transposon techniques. Still particularly, mutations can be obtained by editing methods in particular obtained by the use of meganucleases, Zinc finger nucleases, TALEN or CRISP/Cas9 methods and lead to a new interesting inducer line.

"Mutant plant population" or "mutant library" have here the same meaning and relate, in the context of the invention, to maize plant populations and other species of plant populations such as wheat, sunflower, The screening of these libraries can be done by the use of a polynucleotide comprising or consisting in the nucleotide sequence of SEQ ID No 2 or 4 or a nucleotide sequence at least 80% identical to said nucleotide sequence of SEQ ID No 2, but also by the use of an orthologous sequence as described herein. The goal is, to found mutation(s) in SEQ ID No 2 or in a sequence having homology with SEQ ID No 2 in order to identify for mutants in maize population or mutation(s) in an orthologous sequence from others species such as wheat or sunflower.

By "homology" is meant the level of common nucleic acid or amino acid between two nucleic or amino acid sequence.

These screenings can be carried out by using full orthologous sequence has described herein, when the screening is based on sequencing methods, or with a fragment thereof, when the screening is based on PCR methods.

These methods are known by the man skill of the art.

"Fragment", in the context of screening methods, relates to a number of nucleotides sufficient to provide a specific hybridization on the complementary sequence and allowing amplification by PCR methods. Said fragment may be at least of 8, 10, or 20 nucleotides long and can include the complementary strand of the fragment.

Mutant plant can also be obtained by "gene editing methods", gene editing being proceeded on the SEQ ID No 2, or on nucleotide sequence at least 80% identical to said nucleotide sequence of SEQ ID No 2 or on orthologous sequence as previously obtained. If the "editing method" is based on CRISP/cas9 system, the short RNA molecule used should be homologous to the above targeted sequence.

As previously mentioned, the sequence identified by the inventors has been mutated by the insertion of the 4 bp CGAG in exon 4 of the gene in comparison with the wild type sequence of the gene which is found in maize and the consequence of said mutation is a frame shift leading to 20 non conserved amino acids followed by a premature STOP codon.

Also, in one embodiment of the above mentioned process for screening a mutant plant population for enhanced haploid induction, the polynucleotide according to the invention or the polynucleotide comprising or consisting in the nucleotide sequence of SEQ ID No 2 or 4 or of a nucleotide sequence at least 80% identical to said nucleotide sequence of SEQ ID No 2 or 4 is used to screen for mutation within said exon 4 of said polynucleotide according to the invention, of said nucleotide sequence of SEQ ID No 2 or 4 or said nucleotide sequence at least 80% identical thereof, and more particularly for frame shift mutation within said polynucleotide according to the invention, of said nucleotide sequence of SEQ ID No 2 or 4 or said nucleotide sequence at least 80% identical thereof.

In another embodiment of the above mentioned process for screening a mutant plant population or mutant library for enhanced haploid induction, the polynucleotide according to the invention or the polynucleotide comprising or consisting in the nucleotide sequence of SEQ ID No 2 or 4 or of a nucleotide sequence at least 80% identical to said nucleotide sequence of SEQ ID No 2 or 4 is used to screen for a mutation inducing modified expression of said polynucleotide according to the invention, of said polynucleotide comprising or consisting in the nucleotide sequence of SEQ ID No 2 or 4 or of said nucleotide sequence at least 80% identical thereof. Indeed, a mutation on the control of the expression, in particular a mutation inducing inhibition of the transcription of said above mentioned sequences can also lead to a new interesting inducer line. For example, this mutation could be in the promoter sequence associated with the SEQ ID No 2 or in the promoter sequence of the orthologous sequence thereof.

The GRMZM2G471240 gene is predicted to code for a phospholipase (PL) and is also named ZmPL. Analysis of the deduced amino acid sequences of the wildtype ZmPL$_{HD99}$ protein of SEQ ID No 25 revealed the presence of two S-palmitoylation sites at position 10 and position 423 as well as an S-farnesylation site at position 423. The second site (423) is missing in the truncated ZmPL$_{PK6}$ protein of SEQ ID No 24. Together with the fact that the truncated ZmPL$_{PK6}$ protein of SEQ ID No 24, is no longer localized in the cytoplasmic membrane, this suggests that the presence of a lipid anchor domain at the C-terminus of ZmPL$_{HD99}$ of SEQ ID No 25, may be essential for the correct subcellular localization of the protein.

A survey of the deduced amino acids from cereal orthologues showed that the proteins from Brachypodium dystachion (SEQ ID 29), Sorghum bicolor (SEQ ID 30), Panicum virgatum (SEQ ID 31 and SEQ ID 32), Setaria italica (SEQ ID 33) and Oryza sativa (SEQ ID 34) are all predicted to have lipid anchors at their N-terminus and C-terminus, whereas for Hordeum Vulgare (SEQ ID 28) only a N-terminal lipid anchor was predicted. The data suggest that the presence of an N-terminal and a C-terminal lipid anchor by S-palmitoylation, S-farnesylation and/or S-geranylgeranylation may be necessary for subcellular localization in the cytoplasmic membrane.

The presence of an N-terminal and C-terminal membrane anchor may be a useful additional criterion for the identification of functional orthologues in cereals and non-cereals, where phylogenetic analysis, even combined with the criterion of expression in the pollen, is often not sufficient.

Identification of an orthologous sequence as described herein may thus include a step of identification of a lipid anchor domain in C terminal and N terminal of the polypeptidic orthologue sequence as described herein and/or a step of identification of an ortholgoues sequence which is expressed in pollen and/or in the pollen tube of the plant.

In one embodiment, the orthologous sequence as described therein is thus a polypeptidic sequence which comprises a lipid anchor domain in its C-terminal and N-terminal polypeptidic sequence and/or is a sequence which is expresses in pollen and/or pollen tube of the plant.

In another embodiment, the mutant of the orthologous sequence as described therein does not comprise a lipid anchor domain in its C-terminal polypeptide sequence. For example, identification of a ZmPL functional orthologue from *Arabidopsis thaliana* by the use of a phylogenetic tree of all patatin-like phospholipases was constructed. Using preferential expression in pollen and the prediction of an N-terminal and a C-terminal lipid anchor as additional criteria, the gene At1g61850.1 was identified as the best candidate, and mutants N642695, N657713 and N596745 (obtained from NASC) are putative mutant haploid inducer plant identified by the method according to the invention.

Specific systems exist to create targeted mutations, for example the ZFN, meganuclease, TALEN or CAS9/CRISPR systems (Gaj et al., 2013). They can be used to alter in a site-specific fashion the polynucleotide according to the invention or the polynucleotide comprising or consisting in the nucleotide sequence of SEQ ID No 2 or 4 or of a nucleotide sequence at least 80% identical to said nucleotide sequence of SEQ ID No 2 or 4 or fragments thereof, and can be used to create new specific mutants for haploid induction ability. These systems can also be used to create targeted mutation in other species for example, wheat or sunflower by the use of these technologies on orthologous sequences.

In another embodiment, the present invention further relates to a process for determining the presence, the absence or the alteration of the polynucleotide according to the invention in a maize plant, comprising at least isolating nucleic acid molecules from said maize plant and amplifying sequences homologous to the polynucleotide according to the invention. Isolation step and amplification step can be carried out by methods well known by a man skilled in the art, such as for example those described in Dellaporta et al. 1985. Maize DNA miniprep, p. 36-37, in Molecular Biology of Plants, Malberg, J. Messing and I. Sussex, eds. Cold Spring Harbor Laboratory, Cold Spring Harbor, N.Y.; Dellaporta et al. 1983. A plant DNA minipreparation: Version II, Plant Molecular Biology Reporter Volume 1, Issue 4, pp 19-21; John G. K. Williams et al., 1990. DNA polymorphisms amplified by arbitrary primers are useful as genetic markers, Nucleic Acids Research, Vol. 18, No. 22 6531.

As previously mentioned, the inventors have also identified new molecular markers. Said molecular markers allow to identify haploid inducer maize plants. This marker being specific of the allele responsible of haploid induction in maize, it opens the way for an easiest, fastest and cheapest method of control of such character.

The present invention thus also relates to a genetic marker of haploid induction in maize plants, wherein said genetic marker able to identify the polymorphism between the nucleotide sequences SEQ ID No 5 and SEQ ID No 42. In particular, said genetic marker is the genetic marker GRMZM2G471240_14. The genetic marker GRMZM2G471240_14 allows identification of the polymorphism as described in the tables 5a and 6 and is described in example 5. By "genetic marker" is meant a specific DNA sequence that can be identified within the genome of an individual and can be used to locate a particular locus of interest and/or determine the allelic origin of the plant at the locus. In the context of the invention, "genetic marker" can identify the locus responsible of haploid induction in maize, and determine the allelic variant at this loci. This DNA sequence can be a coding sequence. The marker can be read as dominant or co-dominant.

In the framework of the present invention, the genetic marker can detect plants carrying one or two alleles of the isolated polynucleotide responsible of haploid induction in maize plants according to the invention. The SEQ ID No 5 corresponds to the allelic sequence of the genetic marker carrying the 4 pb nucleotide insertion and responsible of haploid induction whereas the SEQ ID No 42 corresponds to the allelic sequence of the genetic marker without the insertion (wild type sequence). For proper inducer property the inducer line needs to be homozygous for this allele. The described genetic marker enables quick testing of seeds before sowing, seedlings or plants in development and retaining those with the desired characteristics, i.e. those which are haploid inducers.

This method could be used for example to follow the allele of the isolated polynucleotide responsible of haploid induction in maize plants according to the invention during the back cross of this allele in maize material for example exotic lines.

As a consequence, the present invention also relates to a process of identification of a haploid inducer maize plant comprising detecting in a maize plant or seed the genetic marker according to the invention.

The term "allele" refers to one of two or more different nucleotide sequences that occur at a specific locus. A first allele is found on one chromosome, while a second allele occurs at the same position on the homologue of that chromosome, e.g., as occurs for different chromosomes of a heterozygous individual, or between different homozygous or heterozygous individuals in a population. A "favorable allele" is the allele at a particular locus that confers, or contributes to, a desirable property, e.g., induction of haploid plant in maize.

As previously mentioned, the multiplication of the inducer line is critical since pollination by foreign material is frequent due to poor pollen efficiency of these lines. As a consequence, these lines need to be regularly controlled for purity. The use of the genetic marker according to the invention should drastically reduce the time and means needed to achieve it.

The present invention thus further relates to the use of the genetic marker according to the invention for quality control of seed lots in maize haploid inducer lines, comprising the steps of:
(a) taking a sample of seeds from a seed lot in a maize haploid inducer line;
(b) conducting molecular analyses to identify and quantify the presence of haploid inducer or non-inducer alleles;
(c) deducing from step b) the genetic purity value of the lot for the haploid inducer character.

The molecular analyses are well within the knowledge of the man skilled in the art. For example, the KASP method from KBioscience (LGC Group, Teddington, Middlesex, UK) can be used. The KASP™ genotyping system uses three target specific primers: two primers, each of them being specific of each allelic form and one extra primer on the reverse strand of DNA to achieve amplification, which is shared by both allelic forms. Each target specific primer also presents a tail sequence that corresponds to one of two FRET probes: one labelled with FAM® dye and the other with HEX® dye. After PCR reaction, the nature of the emitted fluorescence is used to identify the allelic form present in the mix of the studied DNA (He et al 2014).

The "genetic purity value" refers to the degree of contamination of a seed lot, in the context of the present invention, by non-inducers of haploid.

The invention will be further illustrated by the following figures and examples

FIGURES

FIG. 1: Observed segregation bias against PK6 allele in the subset of 531 recombinants using 16 SNP markers evenly distributed in the region.

FIG. 2: Alignment of GRMZM2G471240 cDNA sequences obtained by canonical splicing from reference sequence B73 (SEQ ID No 23), and from genotypes HD99 (SEQ ID No 4) and PK6 (SEQ ID No 3). Among them was a 4 bp insertion in exon 4 of the GRMZM2G471240 candidate gene for PK 6.

FIG. 3: Alignment of deduced amino acid sequences for gene GRMZM2G471240 from B73 (SEQ ID No 26 and SEQ ID No 27), HD99 (SEQ ID No 25) and PK6 (SEQ ID No 24). The consequence of the 4 bp insertion in exon 4 of the GRMZM2G471240 nucleic acid sequence of PK6 is a frame shift leading to 20 non conserved amino acids followed by a premature STOP codon. T01 and T02 (SEQ ID No 26 and SEQ ID No 27) correspond to alternative gene models proposed by the annotation of the B73 reference sequence, which differ in the length of exon 2 (see FIG. 1). All cDNA products cloned from pollen of genotypes PK6 and HD99 correspond to gene model T01.

Figure 4:
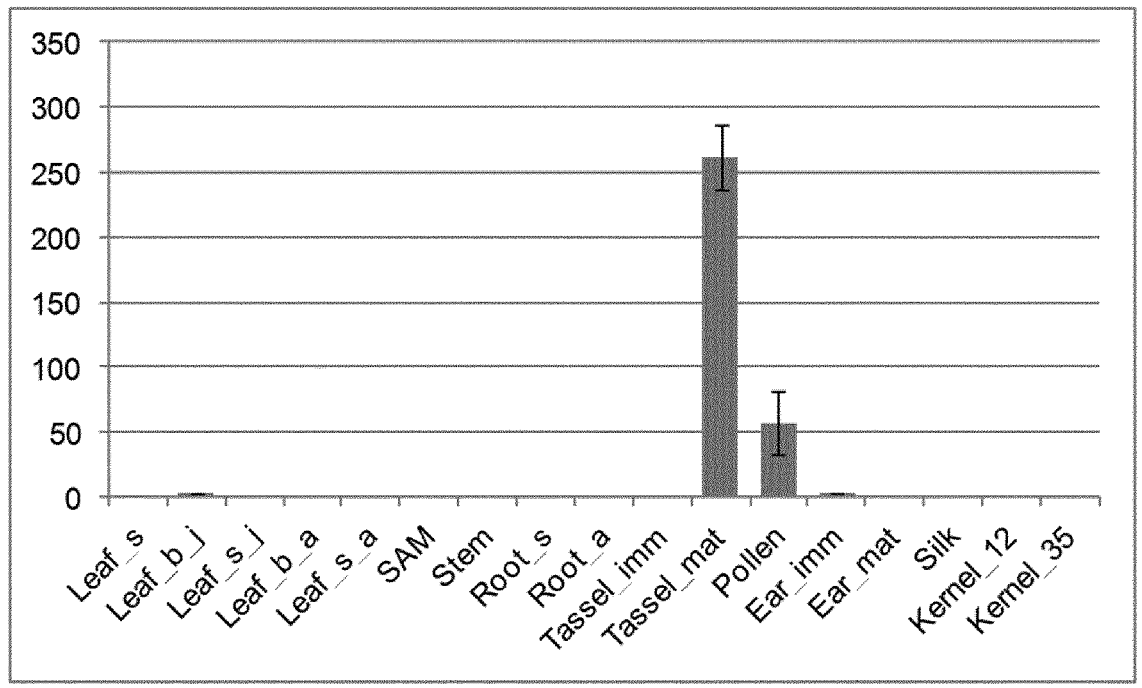

FIG. 4: Relative expression level by qRT-PCR with primers Pat_qRT_F1 and Pat_qRT_R1 (sequence SEQ ID No 6 and SEQ ID No 7) specific for amplification of gene GRMZM2G471240, arbitrary units. (Leaf_s: aerial parts of 5 DAS seedlings; Leaf_b_j: leaf blade of juvenile leaf 3; Leaf_s_j: leaf sheath of juvenile leaf 3; Leaf_b_a: leaf blade of adult leaf 11; Leaf_s_a: leaf sheath of adult leaf 11; SAM: shoot apical meristem roughly dissected at 21 DAS; Stem: stem section between leaf 9 and leaf 10; Root_s: roots of 5 DAS seedlings; Root_a: roots adult at 38 DAS; Tassel_imm: tassel immature at 45 DAS; Tassel_mat: tassel mature with anthers and pollen; Pollen: pollen; Ear_imm: immature ear (2 cm); Ear_mat: mature ear; Silk: silks emerged from husk leaves; Kernel_12: kernel 12 DAP; Kernel_35: kernel 35 DAP).

Figure 5:
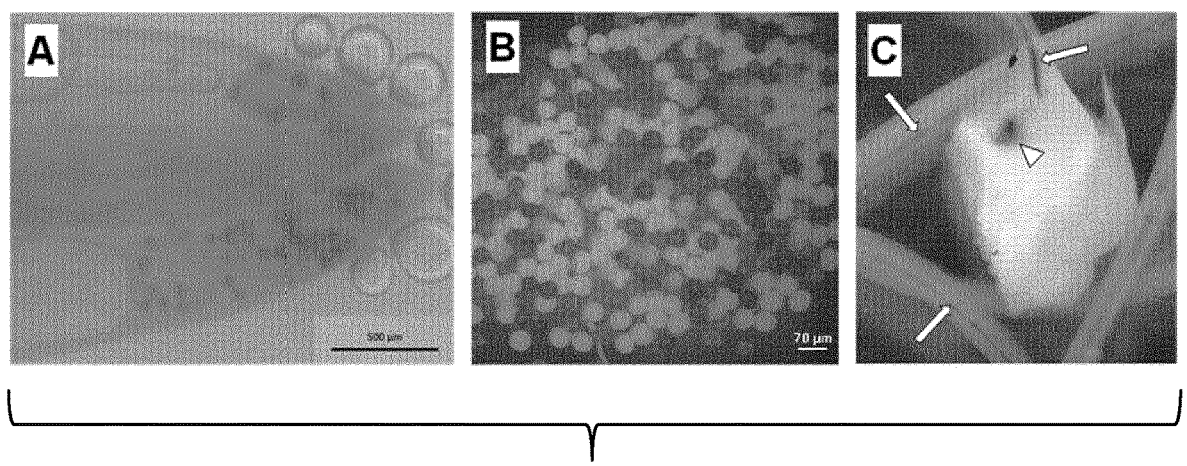

FIG. 5: Pollen-specific expression of gene GRMZM2G471240
Promoter activity of gene GRMZM2G471240 was visualized in transgenic maize plants by histochemical detection of the GUS reporter. In mature anthers of hemizygous plants (A) blue GUS staining was found in about 50% of the pollen grains, whereas no GUS staining was observed in the anther. Observations of isolated pollen (B) and of wild type silk and ovule (C) after pollination with transgenic pollen revealed GUS activity in the pollen tube (arrow) and the fertilized embryo sac (arrow head).

Figure 6:
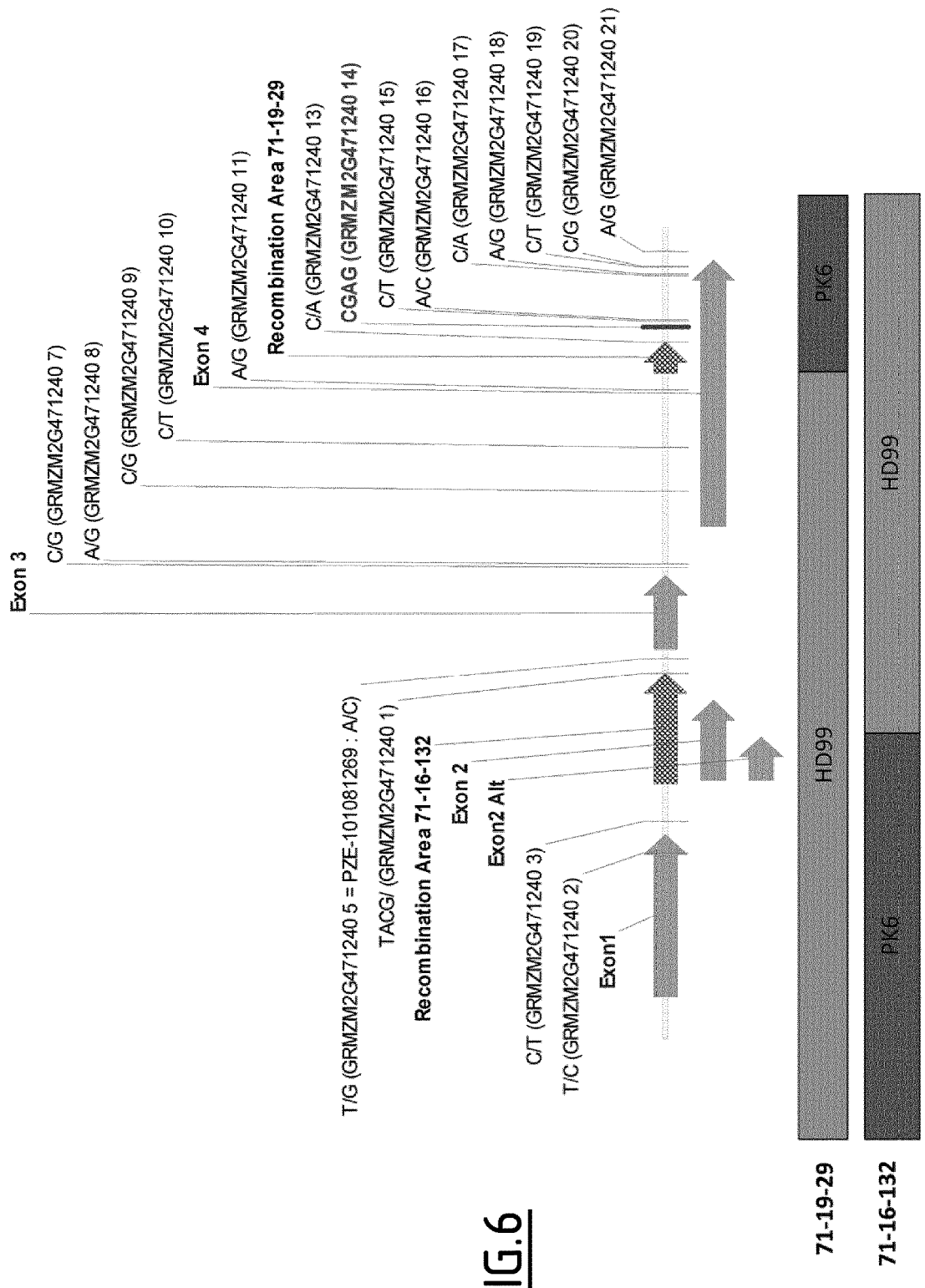

FIG. 6: Graphical representation of marker coverage and recombination breakpoints (determined by allelic sequencing) on the candidate gene GRMZM2G471240, for the two recombinant lines 71-19-29 and 71-16-132.

Figure 7:
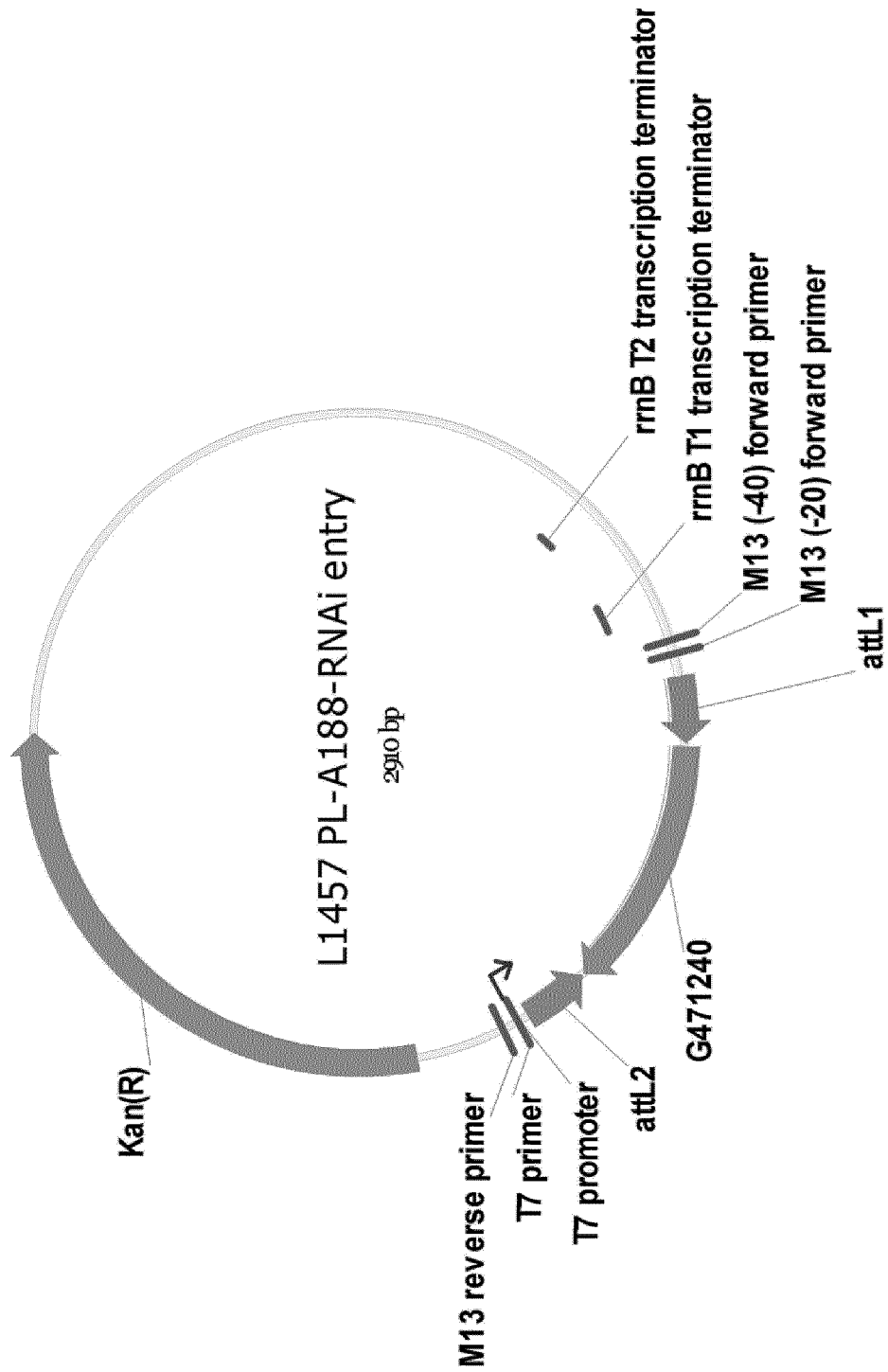
Figure 8:
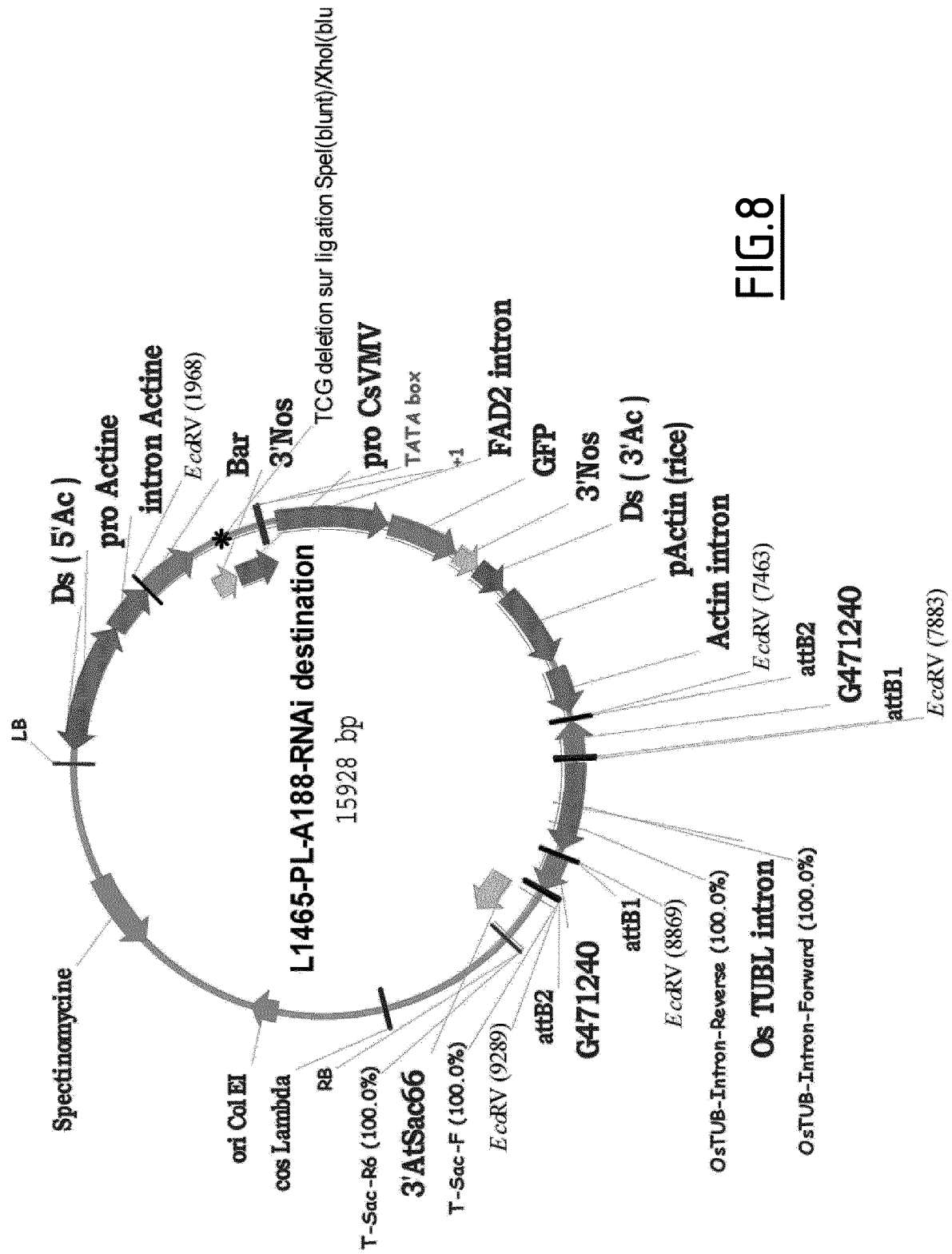
Figure 9:
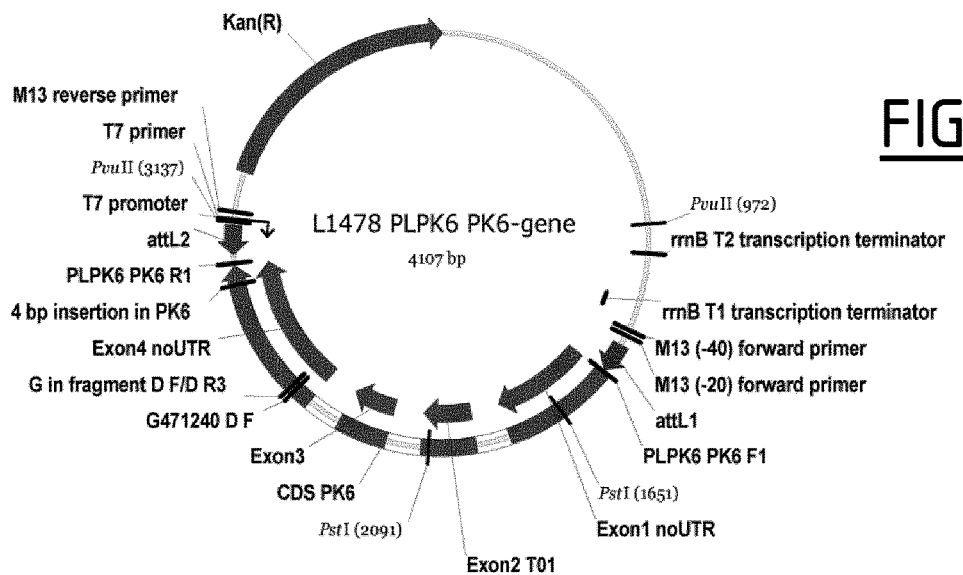
Figure 10:
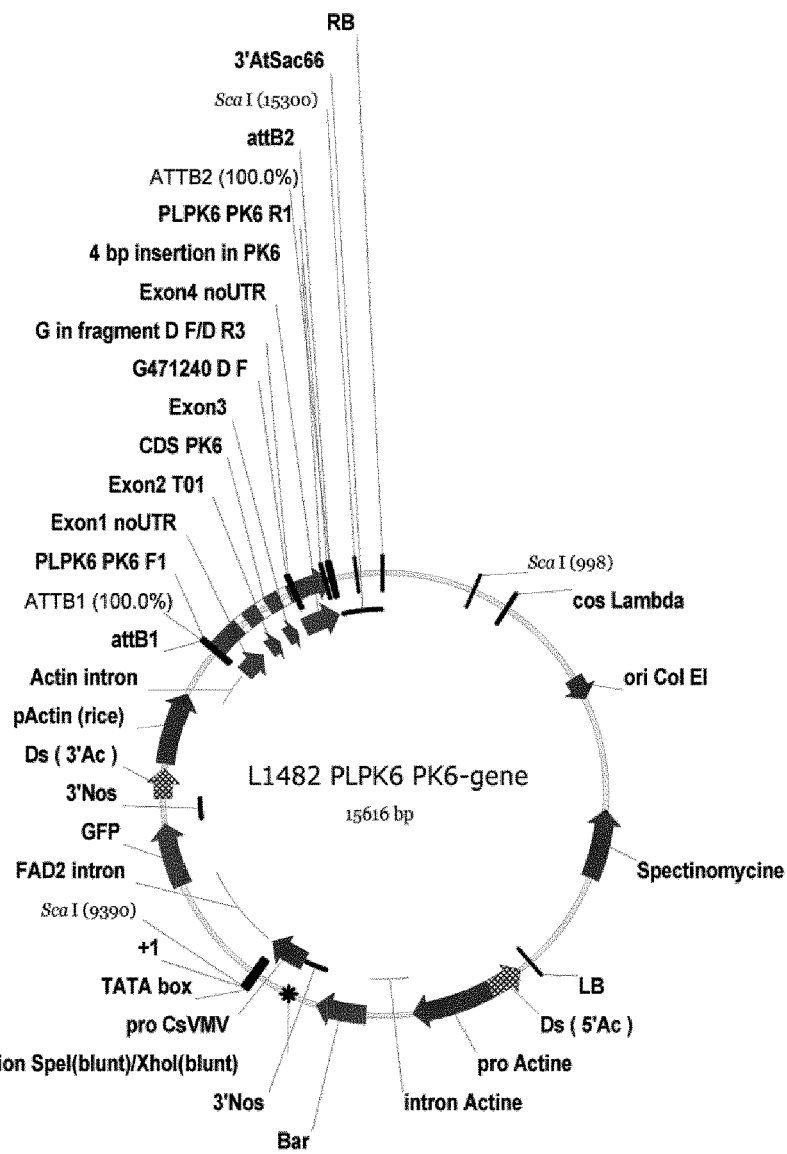
Figure 11:
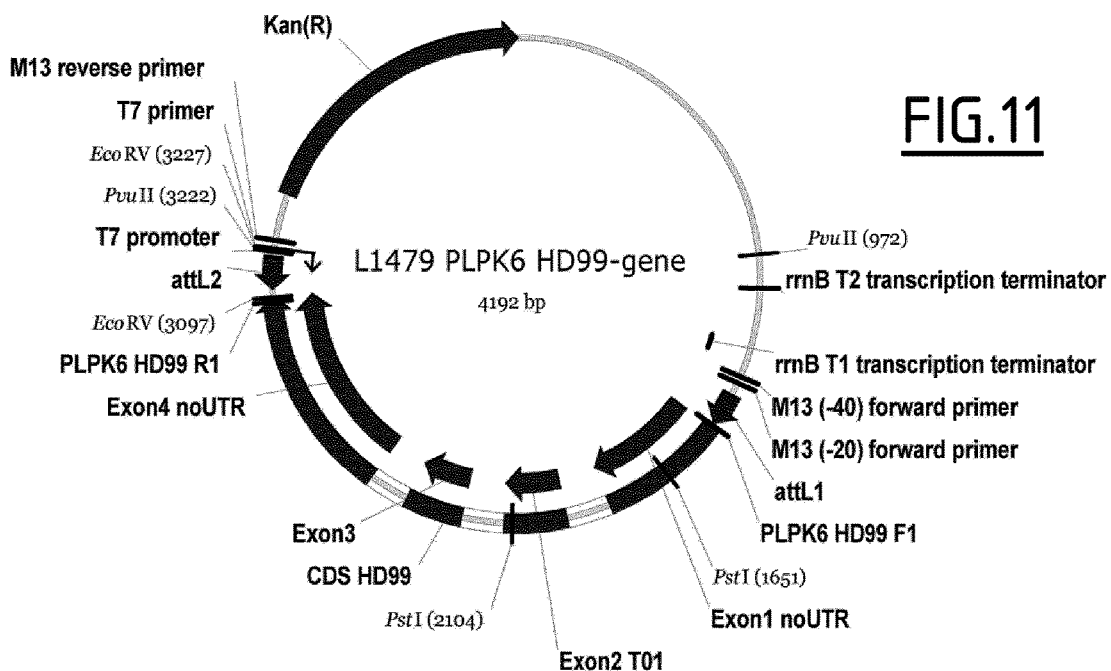
Figure 12:
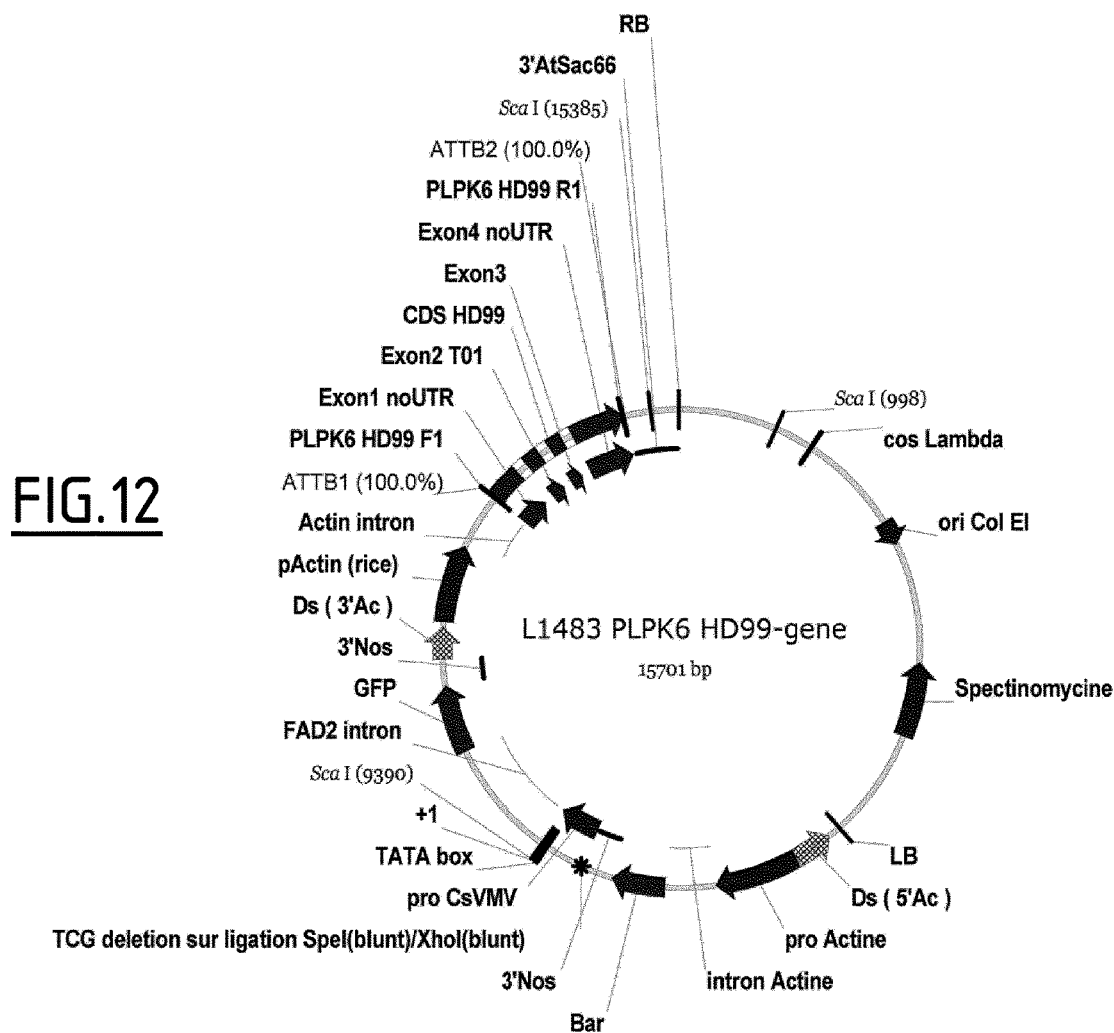
Figure 13:
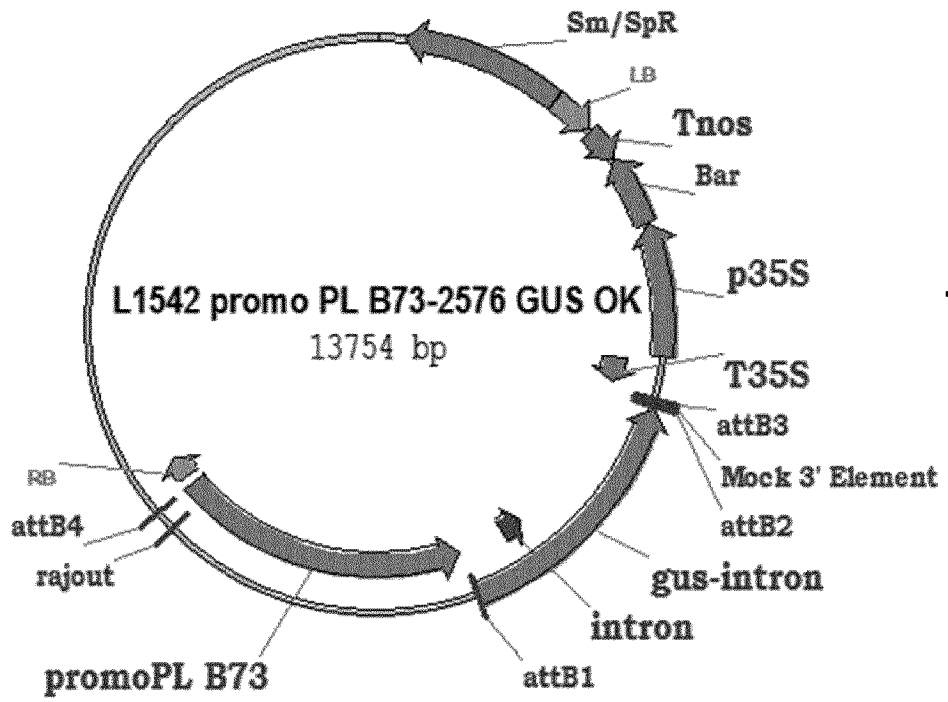

FIG. 7: plasmid map for L1457
FIG. 8: plasmid map for L1465
FIG. 9: plasmid map for L1478
FIG. 10: plasmid map for L1482
FIG. 11: plasmid map for L1479
FIG. 12: plasmid map for L1483
FIG. 13: plasmid map for L1542 (pZmPL$_{B73}$full::GUS::pmock3')

Figure 14:
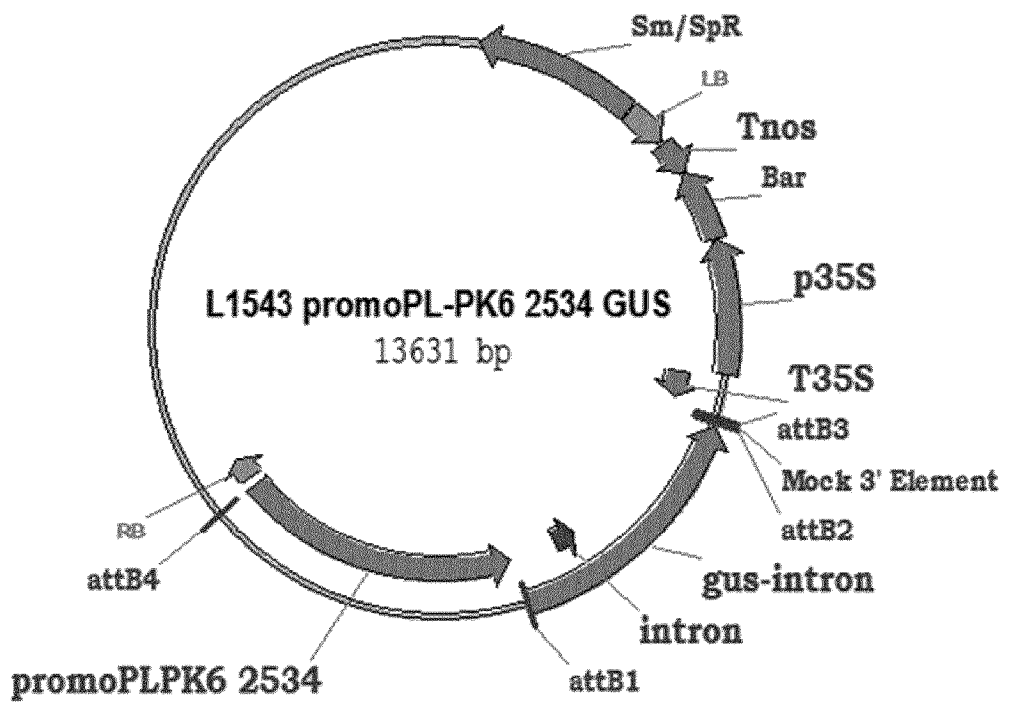

FIG. 14: plasmid map for L1543 (pZmPL$_{PK6}$full::GUS::pmock3')

Figure 15:
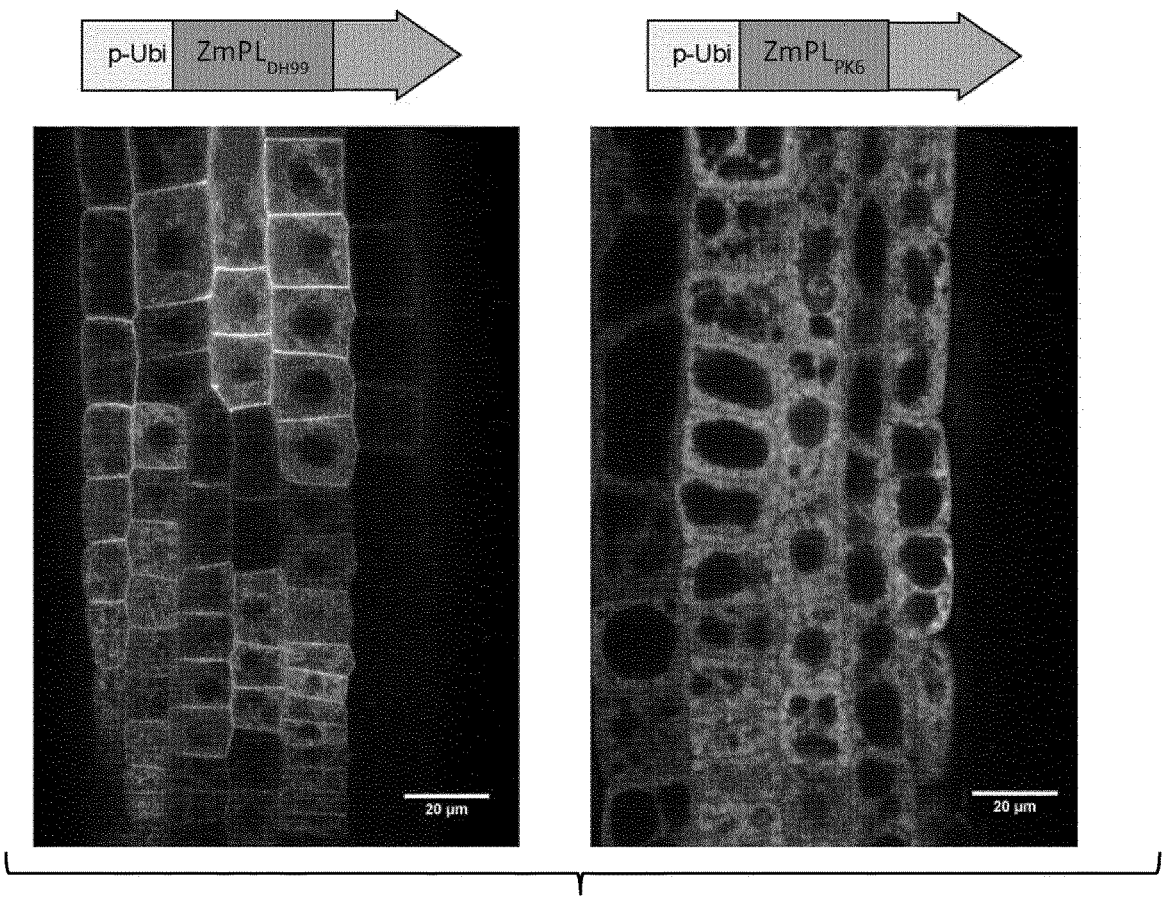

FIG. 15: Subcellular localization of ZmPL: Confocal imaging of Arabidopsis root tips expressing either truncated ZmPL$_{PK6}$ or wild-type ZmPL$_{HD99}$ fused to citrine fluorescent protein. Signal of both protein fusions can be seen in the cytosol whereas only wild-type ZmPL$_{HD99}$::citrine accumulated in the plasma membrane.

Figure 16:
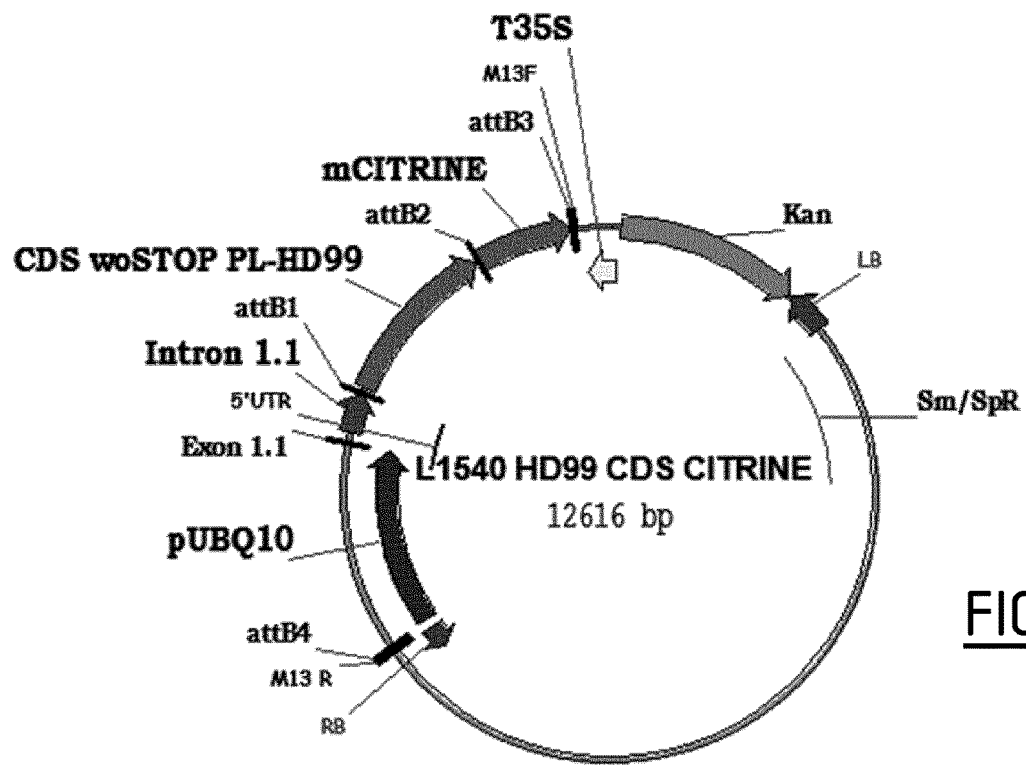

FIG. 16: plasmid map for L1540 (pUBQ10::CDS-ZmPL$_{HD99}$::Citrine)

Figure 17:
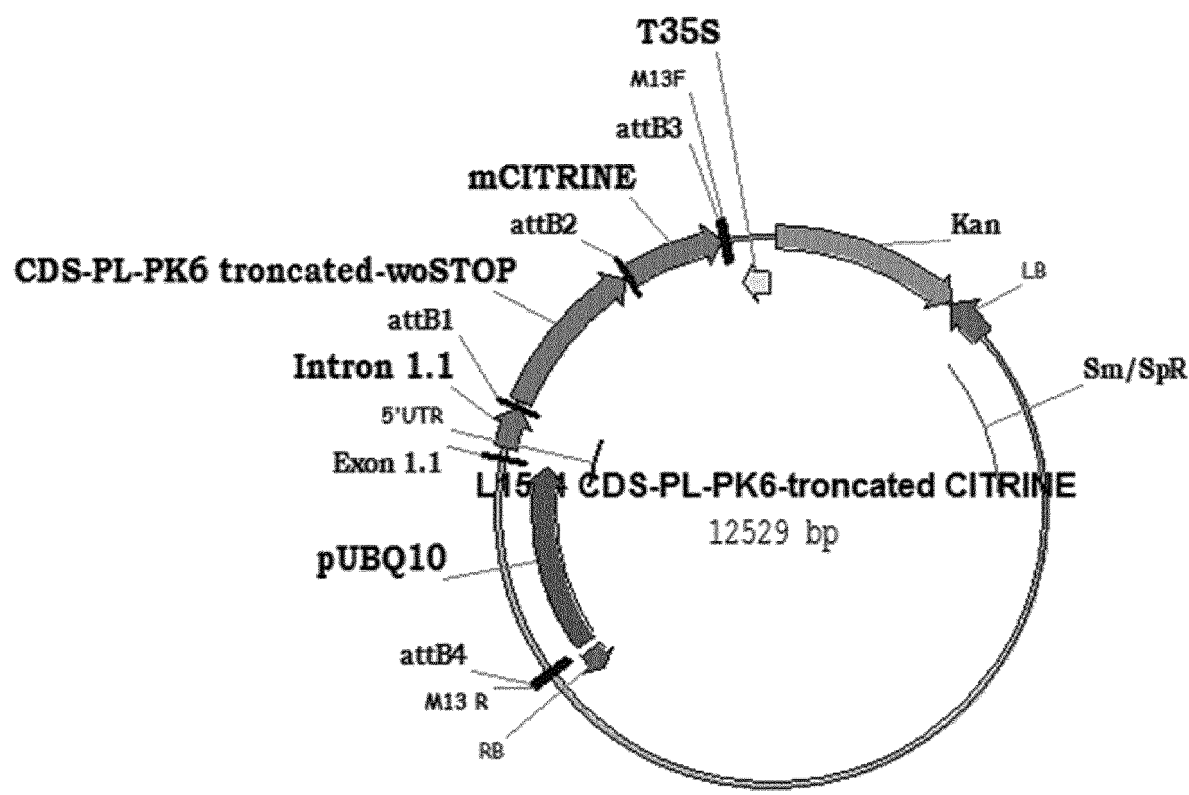

FIG. 17: plasmid map for L1541 (pUBQ10::CDS-ZmPL$_{PK6}$::Citrine)

EXAMPLES

Example 1

Map Based Cloning of the Gene Involved in Haploid Induction
Fine Mapping
For fine mapping of the ggi1 locus, a previously identified QTL for haploid induction (Barret et al., 2008), 96 highly-recombinant F2i3S2 plants (F2 intermated for 3 generations followed by 2 selfs) and 18 single seed descendants (selected for induction over 7 generations) of the HD99×PK6 cross were genotyped with 10 markers in the umc1144/bnlg1811 interval and tested for haploid induction. Phenotyping was carried out by pollinating the hybrid F564×HD7 homozygous for the recessive glossy1 mutation with pollen of the plants of interest (all wildtype for the GLOSSY1 locus) and counting the percentage of seedlings with a mutant glossy1 phenotype (percentage of glossy) by visual inspection, assuming that the percentage of glossy reflected the percentage of haploid plants. The left border of the QTL interval was determined between markers umc1144 (pos 64.2 Mb) and AY110477 (pos 66.9) and the right border between markers GRMZM2G120587 (pos 68.1 Mb) and CL424968 (pos 70.6 Mb). N1078 (SSD) and SMH37 (F2i3S2), the two inducing lines with the smallest PK6 region at the locus were backcrossed to HD99. After a selfing step a total of 10275 F2 have been generated and screened for recombination within the QTL interval.
First, 130 SNP markers located on chromosome 1 between pos. 65 and 70 Mbp (comprising 34 SNPs discovered by candidate gene re-sequencing) were evaluated for polymorphism between the parents using a KASP genotyping platform (http://www.lgcgenomics.com). From those, 26 polymorphic markers (Table 1) evenly distributed in the region were validated in a subset of 192 F2 plants comprising 96 derived from N1078 and 96 derived from SMH37.
QTL analysis has been reprocessed with these extra marker data on the 114 initial plants and results suggested a putative interval for the underlying determinant of the QTL between SYN24144 (67.72 Mb) and PZE-101081844 (69.28 Mb). Based on this information, three markers flanking the ggi1 interval (GRMZM2G100497_10, GRMZM2G152877_6 and SYN35770) located on chromosome 1 at positions 65734188, 66958748 and 69889217 bp on the B73 reference map v2, respectively, were chosen to screen the 10275 F2 plants for recombination in the interval.

TABLE 1

SNP markers used in the genotyping of 114 initial recombinants (96 F2i3S2 + 18 SSD). The two SNP markers in italics mark the limit of the putative interval for the underlying determinant of the ggi1 QTL.

| KASP Markers id | Chr1_bp (B73 RefMap V2) | Polymorphism |
|---|---|---|
| GRMZM2G100497_10 * | 65734188 | A/G |
| GRMZM2G100497_9 | 65734040 | T/C |
| GRMZM2G152877_16 | 66958261 | G/T |
| GRMZM2G152877_6 * | 66958748 | G/T |
| SYN17701 | 67056433 | A/C |
| PZE-101080848 | 67646656 | A/C |
| GRMZM2G051879_48 | 67646723 | /TTTGTTTTGCA |
| SYN24145 | 67727585 | T/C |
| *SYN24144* | *67727790* | *T/C* |
| SYN24142 | 67727977 | A/C |
| SYN25767 | 67850058 | T/C |
| PZE-101081233 | 68179267 | A/G |
| PZE-101081269 | 68241700 | T/G |
| SYN6864 | 68437034 | A/G |
| SYN6867 | 68437046 | T/C |
| SYN20148 | 68555034 | T/C |
| SYN20145 | 68557798 | A/G |
| PZE-101081484 | 68558721 | A/G |
| SYN25793 | 68670617 | T/C |
| *PZE-101081844* | *69289243* | *T/G* |
| SYN2042 | 69587711 | T/C |
| GRMZM2G117513_1 | 69888509 | A/G |
| ASSAY954_00198 | 69887082 | A/G |
| ASSAY954_00197 | 69887083 | T/G |
| PUT-163a-74233607-3597 | 69887397 | A/C |
| SYN35770 * | 69889217 | A/G |

"*" identifies markers used to screen the entire F2 population for recombinants.

The screening of the 10275 F2 plants with SNP markers GRMZM2G100497_10, GRMZM2G152877_6 and SYN35770 identified 531 recombinant plants on the ggi1 interval.

Fine Mapping of the Distortion Bias Trait

The PK6 allele is counter selected compared to a normal allele with a Mendelian segregation. Thus, progeny derived from a plant heterozygous at this locus is distorted and has less than the theoretical rate of 50% of PK6 type alleles. Assuming that the same PK6 locus was responsible for haploid induction and distortion bias, the gene of haploid induction can be fine mapped based on the distortion score of genetic markers at this locus.

A subset of 48 recombinants plants, having a crossing over between GRMZM2G305400b_2 and SYN20148 (Table 2), have been selected and selfed. For each family a set of 48 derived seeds, or less if the selfing was not successful, have been sown and plantlets have been genotyped for the 16 SNP listed in Table 2. Analyses have been done by comparing for each marker the total number of homozygotes plants for Pk6 and HD99 alleles, respectively. The strongest bias was observed for the marker GRMZM2G471240_1 (Table 2 and FIG. 1).

TABLE 2

Observed segregation bias against PK6 allele for 48 recombinants in the subset of 531 recombinants using 16 SNP markers evenly distributed in the region. Column Chr1_bp (V2) represents the physical position on the B73 reference genome v2. The segregation bias is the number of PK6 alleles divided by the number of HD99 alleles.

| KASP Markers id | Polymorphism | Chr1_bp (V2) | Segregation Bias (nb allele PK6/nb allele HD99) |
|---|---|---|---|
| GRMZM2G100497_10 | A/G | 65734188 | 0.31 |
| GRMZM2G152877_6 | G/T | 66958748 | 0.33 |
| GRMZM2G051879_48 | /TTTGTTTTGCA | 67646723 | 0.33 |
| SYN24142 | A/C | 67727977 | 0.33 |
| SYN25767 | T/C | 67850058 | 0.33 |
| GRMZM2G305400b_2 | T/G | 67993670 | 0.33 |
| GRMZM2G120587_2 | /GCA | 68134724 | 0.25 |
| PZE-101081233 | A/G | 68179267 | 0.18 |
| GRMZM2G471240_1 | TACG/ | 68241668 | 0.167 |
| GRMZM2G003530_2 | T/C | 68437955 | 0.41 |
| SYN20148 | T/C | 68555034 | 0.42 |
| PZE-101081484 | A/G | 68558721 | 0.42 |
| SYN25793 | T/C | 68670617 | 0.42 |
| PZE-101081844 | T/G | 69289243 | 0.42 |
| SYN2042 | T/C | 69587711 | 0.44 |
| SYN35770 | A/G | 69889217 | 0.42 |

A set of 48 recombinants comprising 20 recombinants located within the interval with strong segregation bias against PK6 (within 68134724 and 68437955 on the B73 reference genome v2) and 28 extra recombinants in the flanking regions (within 67993670 and 68555034 on the B73 reference genome v2) were considered for further studies.

Analysis of the 48 Recombinants at the Locus

Amongst the 48 families selected to take forward, only 31 produced F2 seeds. For each one of those 31 recombinants producing seeds, 48 seeds (less in a few cases, if not available) were germinated and genotyped in order to select homozygous recombinant plants (HomoRec). Between 3 and 5 plants (preferentially homozygous recombinant plants) per recombinant family were further grown and self-pollinated.

For the initial screening of 31 families (up to 48 plants per family) only 4 markers were used: SYN25767, GRMZM2G305400b_2, SYN20148 and SYN25793 (see Table 2). The detected homozygous recombinants plants were further genotyped with a set of 78 markers.

Gene Content of the ggi1 Region

Preliminary analysis of the gene content in the maize B73 reference genome v2 highlighted 13 gene models (Table 3). Two of the putative gene models (GRMZM2G471240 and GRMZM2G062313) were expressed in anthers. Expression data have been obtained by interrogation of an eFP browser, Winter et al., 2007, Li et al., 2010 and Sekhon et al., 2011. Sequence analysis of the two gene models revealed the two corresponding genes are homologues from the Acyl transferase/acyl hydrolase/lysophospholipase family. The second one appeared to be a pseudogene and is then likely not expressed and the result obtained from the eFP browser should be an artefact due to the homology with the GRMZM2G471240 gene. This pseudogene may have arisen by duplication of the first one. The expression of GRMZM2G471240 in anthers (Table 3) made of it the best candidate gene which may be responsible for the ggi1 phenotype. Moreover, the marker GRMZM2G471240_1 developed on the gene GRMZM2G471240 exhibits the strongest PK6 allele segregation bias among the tested markers (FIG. 1 and Table 2).

TABLE 3

Genome position and expression data available for the 13 gene models identified within the ggi1 interval. The filtered gene set (FGS, solid evidence for gene) contains the 32540 genes of the maize genome published by Schnable et al., 2009. The working gene set (WGS) contains more than 30000 additional gene models, many of which are mere informatic predictions without further evidence. Expression data comes from interrogation of an eFP browser, Winter et al., 2007, Li et al., 2010 and Sekhon et al., 2011.

| Id | Chr1_Pos(bp-V2) | Set | Expression data |
|---|---|---|---|
| GRMZM2G544129 | 68212317 | WGS | not in eFP browser database |
| GRMZM2G544135 | 68215141 | WGS | not in eFP browser database |
| GRMZM2G703616 | 68236616 | WGS | Constitutive |
| GRMZM2G471240 | 68240862 | FGS | Anthers |
| GRMZM2G062320 | 68318898 | FGS | constitutive |
| GRMZM2G062313 | 68323867 | WGS | Anthers |
| GRMZM2G062304 | 68365105 | WGS | not in eFP browser database |
| AC213048.3_FG003 | 68398780 | WGS | germinating seed |
| GRMZM2G520395 | 68404999 | WGS | not in eFP browser database |
| AC213048.3_FG002 | 68409826 | FGS | not in eFP browser database |
| GRMZM2G047877 | 68415868 | WGS | not in eFP browser database |
| GRMZM2G047843 | 68419166 | WGS | Constitutive |
| GRMZM2G510681 | 68428105 | WGS | not in eFP browser database |

GRMZM2G471240 Specific Expression is Confirmed by qRT-PCR Experiments in Maize Tissues Since cross-hybridisation between closely related genes cannot be excluded in the micro-array data used to generate the eFP browser (Sekhon et al., 2011), gene specific primers Pat_qRT_F1 and Pat_qRT_R1 (see Table 9 for SEQ ID No 6 and SEQ ID No 7), were used to do qRT-PCR on different maize tissues of genotype A188 (FIG. 4).

Approximately 100 mg of fresh tissue was quick frozen in liquid nitrogen and ground to powder with mortar and pestle. Total RNA was extracted with 1 mL of Tri-reagent according to the instructions of the supplier (Invitrogen). After ethanol precipitation, the RNA was resuspended in 30 µL of RNase-free water and treated with RNase-free DNase. The DNase was inactivated according to the instructions of the supplier (Ambion). Approximately 5 µg of total RNA were reverse transcribed using random hexamers (Amersham Biosciences) and reverse transcriptase without RNaseH activity (Fermentas) in a final volume of 20 µL. A total of $2.5 \times 10^5$ copies of GeneAmplimer pAW109 RNA (Applied Biosystems) were added to the RT reaction. The cDNA was diluted 50 times, and 2 µL was used in a volume of 20 µL containing 10 µL of the FastStart SYBR Green Master mix (Roche) on a StepOne Real-Time PCR System (Applied Biosystems). According to the manufacturer's protocol, the following program was used: 10 min at 95° C., followed by 40 cycles of 95° C. for 10 sec and 60° C. for 30 sec. Data were analysed using the StepOne Software v2.3 (Applied Biosystems). Expression levels were calculated using Actin as reference gene. The primers used are actin-q-F and actin-q-R respectively of SEQ ID No 8 and SEQ ID No 9 listed in Table 9.

The data confirmed the anther-specific expression suggested by the eFP browser and demonstrated in addition that the GRMZM2G471240 gene was (i) only expressed in mature tassels and not in immature tassels and (ii) expressed in pollen. The data did not allow to determine whether the GRMZM2G471240 gene was expressed only in pollen or also in other parts of mature tassels, for example the tapetum.

GRMZM2G471240 Specific Expression is Confirmed by Promoter Fusion in Transgenic Maize Plants.

The use of transgenic maize plants harboring fusions of the promoter of gene GRMZM2G471240 from genotype PK6 or B73 with the GUS reporter gene allowed to determine the spatial expression pattern of the gene during male reproduction. Based on the blue staining indicative of GUS activity, the gene has a strict gametophytic expression in pollen and pollen tube. It is not expressed in the sporophytic tissues of the anther (FIG. 5).

Materials and Methods

Promoter regions of 2657 bp ($ZmPL_{B73}$) corresponding to SEQ ID No 50 and of 2534 bp ($ZmPL_{PK6}$) corresponding to SEQ ID No 51 were amplified with primer pairs attB4_prom_PL_2576_B73 corresponding to SEQ ID No 46/attB1r_prom_PL_2576_B73 corresponding to SEQ ID No 47 and attB4_promoPL_2534_PK6 corresponding to SEQ ID No 48/attB1r_promoPL_2534_PK6 corresponding to SEQ ID No 49, respectively, and introduced into pENTR P4-P1R (Invitrogen) by BP reaction. The prom ZmPL::GUS cassette in plasmids L1542 (pZmPL$_{B73}$full::GUS::pmock3'), FIGS. 13 and L1543 (pZmPL$_{PK6}$full::GUS::pmock3') FIG. 14, used for maize transformation was obtained by triple LR reaction between these promoter fragments, the GUS gene of pEN-L1-SI-L2 (Karimi et al., 2007), pmock3' and the destination vector pB7m34GW (Karimi et al., 2005). GUS (beta-glucuronidase) histochemical staining of dissected organs of transgenic maize plants was performed by dipping tissues into the following solution: 1 mM X-Gluc (5-bromo-4-chloro-3-indolyl-beta-D-glucuronic acid), 0.05% TritonX100, 100 mM sodium phosphate (pH7), and 0.5 mM potassium ferrocyanure and 0.5 mM potassium ferricyanure. The enzymatic reaction was performed overnight at 37° C. after vacuum infiltration.

SNP Densification of the QTL

In order to densify the region, online available resources related to the HAPMAP2 project (Chia et al., 2012) were used to develop 60 new SNP markers between 68180000 pb and 68420000 pb on the physical B73 reference genome v2. Among the 60 newly developed markers (Table 4), only 3 were polymorphic between HD99 and PK6, 18 markers were monomorphic and 39 revealed a presence/absence polymorphism (Presence/Absence Variant or PAV) without amplification in PK6. Even if the use of endpoint PCR protocol to detect absence of the locus is less accurate than use of quantitative PCR, thanks to the high density of markers and the high frequency of absence of amplification at this locus for the PK6 allele, it can be assumed that there is a deletion of at least 100 kb downstream of the GRMZM2G471240 candidate gene in PK6 compared to the reference sequences of genotype B73 and the parental line HD99. This data suggests that the pseudogene GRMZM2G062313 would be absent in PK6.

TABLE 4

HAPMAP2 extra markers within the ggi1 interval and marker allele for HD99 and PK6. NA is for absence of the allele, marker type is defined between the lines HD99 and PK6.

| KASP Markers id | Chr1_bp (V2) | Marker type | HD99 | PK6 |
|---|---|---|---|---|
| PZE0166358891 | 68180209 | Monomorphic | G:G | G:G |
| PZE0166359231 | 68180549 | Polymorphic | T:T | C:C |
| PZE0166359596 | 68180914 | PAV | C:C | NA |
| PZE0166380893 | 68202211 | PAV | G:G | NA |
| PZE0166393715 | 68215033 | Monomorphic | A:A | A:A |

TABLE 4-continued

HAPMAP2 extra markers within the ggi1 interval and marker allele for HD99 and PK6. NA is for absence of the allele, marker type is defined between the lines HD99 and PK6.

| KASP Markers id | Chr1_bp (V2) | Marker type | HD99 | PK6 |
|---|---|---|---|---|
| PZE0166394286 | 68215604 | Polymorphic | G:G | A:A |
| PZE0166394451 | 68215769 | Monomorphic | T:T | T:T |
| PZE0166394686 | 68216004 | PAV | C:C | NA |
| PZE0166394709 | 68216027 | Monomorphic | A:A | A:A |
| PZE0166394976 | 68216294 | PAV | G:G | NA |
| PZE0166407328 | 68228646 | Polymorphic | T:T | G:G |
| PZE0166408365 | 68229683 | PAV | A:A | A:A |
| PZE0166422350 | 68243668 | PAV | C:C | NA |
| PZE0166435898 | 68257216 | Monomorphic | G:G | G:G |
| PZE0166437099 | 68258417 | PAV | A:A | NA |
| PZE0166480583 | 68301901 | PAV | T:T | NA |
| PZE0166480678 | 68301996 | PAV | C:C | NA |
| PZE0166480837 | 68302155 | PAV | C:C | NA |
| PZE0166481099 | 68302417 | PAV | G:G | NA |
| PZE0166481496 | 68302814 | PAV | A:A | NA |
| PZE0166487364 | 68308682 | PAV | G:G | NA |
| PZE0166488186 | 68309504 | PAV | G:G | NA |
| PZE0166488255 | 68309573 | PAV | G:G | NA |
| PZE0166497519 | 68318837 | PAV | A:A | NA |
| PZE0166500667 | 68321985 | Monomorphic | C:C | C:C |
| PZE0166502346 | 68323664 | PAV | C:C | NA |
| PZE0166502392 | 68323710 | PAV | C:C | NA |
| PZE0166502746 | 68324064 | PAV | A:A | NA |
| PZE0166503514 | 68324832 | PAV | C:C | NA |
| PZE0166504940 | 68326258 | PAV | G:G | NA |
| PZE0166505171 | 68326489 | PAV | C:C | NA |
| PZE0166505239 | 68326557 | PAV | C:C | NA |
| PZE0166505408 | 68326726 | PAV | C:C | NA |
| PZE0166505464 | 68326782 | PAV | A:A | NA |
| PZE0166507774 | 68329092 | PAV | A:A | NA |
| PZE0166507883 | 68329201 | PAV | A:A | NA |
| PZE0166508182 | 68329500 | PAV | A:A | NA |
| PZE0166508227 | 68329545 | PAV | C:C | NA |
| PZE0166508604 | 68329922 | PAV | G:G | NA |
| PZE0166508796 | 68330114 | PAV | C:C | NA |
| PZE0166509054 | 68330372 | PAV | T:T | NA |
| PZE0166540610 | 68361928 | PAV | T:T | NA |
| PZE0166540778 | 68362096 | PAV | C:C | NA |
| PZE0166540846 | 68362164 | PAV | T:T | NA |
| PZE0166542974 | 68364292 | PAV | G:G | NA |
| PZE0166544802 | 68366120 | PAV | C:C | NA |
| PZE0166544973 | 68366291 | Monomorphic | A:A | A:A |
| PZE0166546986 | 68368304 | PAV | A:A | NA |
| PZE0166576167 | 68397485 | PAV | T:T | NA |
| PZE0166578457 | 68399775 | Monomorphic | G:G | G:G |
| PZE0166578493 | 68399811 | Monomorphic | A:A | A:A |
| PZE0166586633 | 68407951 | Monomorphic | G:G | G:G |
| PZE0166587074 | 68408392 | Monomorphic | G:G | G:G |
| PZE0166588267 | 68409585 | Monomorphic | C:C | C:C |
| PZE0166588497 | 68409815 | Monomorphic | C:C | C:C |
| PZE0166588562 | 68409880 | Monomorphic | G:G | G:G |
| PZE0166594311 | 68415629 | Monomorphic | C:C | C:C |
| PZE0166594370 | 68415688 | Monomorphic | G:G | G:G |
| PZE0166597249 | 68418567 | Monomorphic | G:G | G:G |
| PZE0166598227 | 68419545 | Monomorphic | G:G | G:G |

Re-sequencing data of the candidate gene GRMZM2G471240 in the PK6 and HD99 parental lines allowed to develop 17 markers on the gene in addition to the previously developed marker GRMZM2G471240_1 (Table 5a). Moreover, a quantitative real time PCR marker named qPCR2313 was developed to follow the presence/absence of the pseudogene GRMZM2G062313 (not present in PK6).

TABLE 5a

Molecular markers developed on GRMZM2G471240 by re-sequencing.

| KASP Markers id | Chr1_bp (V2) | HD99 | PK6 |
|---|---|---|---|
| GRMZM2G471240_2 | 68241270 | C:C | T:T |
| GRMZM2G471240_3 | 68241339 | T:T | C:C |
| GRMZM2G471240_1 | 68241668 | TACG:TACG | — |
| GRMZM2G471240_5 | 68241700 | A:A | C:C |
| GRMZM2G471240_7 | 68241902 | G:G | C:C |
| GRMZM2G471240_8 | 68241910 | G:G | A:A |
| GRMZM2G471240_9 | 68242070 | G:G | C:C |
| GRMZM2G471240_10 | 68242166 | T:T | C:C |
| GRMZM2G471240_11 | 68242296 | G:G | A:A |
| GRMZM2G471240_13 | 68242401 | A:A | C:C |
| GRMZM2G471240_14 | 68242433-68242434 | — | CGAG:CGAG |
| GRMZM2G471240_15 | 68242448 | T:T | C:C |
| GRMZM2G471240_16 | 68242452 | C:C | A:A |
| GRMZM2G471240_17 | 68242547 | A:A | C:C |
| GRMZM2G471240_18 | 68242553 | G:G | A:A |
| GRMZM2G471240_19 | 68242566 | T:T | C:C |
| GRMZM2G471240_20 | 68242569 | G:G | C:C |
| GRMZM2G471240_21 | 68242602 | G:G | A:A |

TABLE 5b

Molecular markers developed on GRMZM2G382717 and GRMZM5G866758 by re-sequencing.

| KASP Markers id | Chr1_bp (V2) | Polymorphism |
|---|---|---|
| GRMZM2G382717_1 | 68113455 | G/T |
| GRMZM5G866758_1 | 68430654 | C/A |

Marker Analysis on a Diversity Panel

A diversity panel was assembled, consisting of 127 lines containing 116 lines from diverse origins representative of the diversity in the maize lines gene-pool, and 11 inducer lines of various origin including PK6 and stock6. The panel was genotyped with a subset of 59 markers (Table 6) previously described (from HAPMAP2 project data and genes re-sequencing data, Table 5a and 5b) between positions 67850001 and 68430000.

TABLE 6

SNP Marker set used on the diversity panel. Marker type refers to the polymorphism between line PK6 and HD99.

| Marker id (KASP and real time PCR) | Chr1_bp (V2) | Marker type |
|---|---|---|
| SYN25767 | 67850058 | SNP |
| GRMZM2G382717_1 | 68113455 | SNP |
| PZE0166359596 | 68180914 | PAV |
| PZE0166380893 | 68202211 | PAV |
| PZE0166394686 | 68216004 | PAV |
| PZE0166394976 | 68216294 | PAV |
| PZE0166408365 | 68229683 | PAV |
| GRMZM2G471240_2 | 68241270 | SNP |
| GRMZM2G471240_3 | 68241339 | SNP |
| GRMZM2G471240_7 | 68241902 | SNP |
| GRMZM2G471240_8 | 68241910 | SNP |
| GRMZM2G471240_9 | 68242070 | SNP |
| GRMZM2G471240_10 | 68242166 | SNP |
| GRMZM2G471240_11 | 68242296 | SNP |
| GRMZM2G471240_13 | 68242401 | SNP |
| GRMZM2G471240_14 | 68242433 | INDEL |
| GRMZM2G471240_15 | 68242448 | SNP |
| GRMZM2G471240_16 | 68242452 | SNP |
| GRMZM2G471240_17 | 68242547 | SNP |
| GRMZM2G471240_18 | 68242553 | SNP |

TABLE 6-continued

SNP Marker set used on the diversity panel. Marker type refers to the polymorphism between line PK6 and HD99.

| Marker id (KASP and real time PCR) | Chr1_bp (V2) | Marker type |
|---|---|---|
| GRMZM2G471240_19 | 68242566 | SNP |
| GRMZM2G471240_20 | 68242568 | SNP |
| GRMZM2G471240_21 | 68242602 | SNP |
| PZE0166422350 | 68243668 | PAV |
| PZE0166437099 | 68258417 | PAV |
| PZE0166480583 | 68301901 | PAV |
| PZE0166480678 | 68301996 | PAV |
| PZE0166480837 | 68302155 | PAV |
| PZE0166481099 | 68302417 | PAV |
| PZE0166481496 | 68302814 | PAV |
| PZE0166487364 | 68308682 | PAV |
| PZE0166488186 | 68309504 | PAV |
| PZE0166488255 | 68309573 | PAV |
| PZE0166497519 | 68318837 | PAV |
| PZE0166502346 | 68323664 | PAV |
| PZE0166502392 | 68323710 | PAV |
| PZE0166502746 | 68324064 | PAV |
| qPCR2313 | 68324620 | PAV |
| PZE0166503514 | 68324832 | PAV |
| PZE0166504940 | 68326258 | PAV |
| PZE0166505171 | 68326489 | PAV |
| PZE0166505239 | 68326557 | PAV |
| PZE0166505408 | 68326726 | PAV |
| PZE0166505464 | 68326782 | PAV |
| PZE0166507774 | 68329092 | PAV |
| PZE0166507883 | 68329201 | PAV |
| PZE0166508182 | 68329500 | PAV |
| PZE0166508227 | 68329545 | PAV |
| PZE0166508604 | 68329922 | PAV |
| PZE0166508796 | 68330114 | PAV |
| PZE0166509054 | 68330372 | PAV |
| PZE0166540610 | 68361928 | PAV |
| PZE0166540778 | 68362096 | PAV |
| PZE0166540846 | 68362164 | PAV |
| PZE0166542974 | 68364292 | PAV |
| PZE0166544802 | 68366120 | PAV |
| PZE0166546986 | 68368304 | PAV |
| PZE0166576167 | 68397485 | PAV |
| GRMZM5G866758_1 | 68430654 | SNP |

Genotyping data obtained on the panel indicated that the large deletion downstream the GRMZM2G471240 candidate gene is present on 11.5% of the 116 maize lines, which are not haploid inducers, suggesting that this large deletion and the presence/absence of the pseudogene GRMZM2G062313 contained in it is not the causal factor of haploid induction.

Among the markers developed on the candidate gene GRMZM2G471240 and tested on the diversity panel, the marker GRMZM2G471240_14 (INS/DEL of 4 bp CGAG/) is the only one having an allele exclusively present on the PK6 genotype and the 10 other inducing lines, which could mean that this is the causal polymorphism of the ggi1 QTL. The insertion of 4 bp targeted by the marker GRMZM2G471240_14 is specific to the original inducing line stock6 and all its tested derivatives including PK6 and is absent in all the non-inducer lines tested. This insertion of 4 bp in the 4$^{th}$ intron of the GRMZM2G471240 gene PK6 causes a translation frameshift resulting in a shorter protein with the last 20 amino acids differing completely from the original protein sequence. None of the other polymorphisms tested were exclusive to PK6 or absent from all non-inducer lines.

Description of Recombinants for the Candidate Gene GRMZM2G471240

Homozygous recombinant plants were obtained and genotyped for 28 of the 31 recombinant families. Two recombinants families appeared to have recombination breakpoints inside the candidate gene GRMZM2G471240 (see FIGS. 2 and 3). The recombinant family 71-19-29 has a recombination breakpoint in exon 4 upstream of the GRMZM2G471240_14 marker (insertion of four bp specific to inductors of haploids, see FIG. 6). The recombinant family 71-16-132 has a recombination breakpoint in a region which encompasses exon 2 (see FIG. 6). Other families exhibit recombination breakpoints on the right and on the left of the candidate gene GRMZM2G471240. These two new recombinants are new alleles at the ggi1 locus and have been evaluated for their inducing ability.

Phenotyping for Haploid Induction Capacity of Recombinants Families

All the 28 homozygous recombinant families from the previous step have been evaluated for inducing ability together with two positive controls (PK6 and RWS), and five negative controls (HD99, F2, WPP112, Nys302 and EM1201).

Each line has been crossed with a tester (female line), and the resulting ear obtained from each cross has been evaluated for their rate of haploid and diploid kernels by counting the percentage of ligule-less or glossy seedlings amongst the progeny (Lashermes and beckert 1988, Neuffer, 1997; Prigge, 2011). The glossy test has been described within example 1. The ligule-less test involves a recessive trait that can be used as alternative to the glossy test as a visual marker for the identification of haploid plants. The induction tests were duplicated and carried out in Limagrain and INRA using the ligule-less and glossy systems respectively. Both duplicates provided the same results. The phenotypic results of both tests show that all the plants that are PK6 at the marker GRMZM2G471240_14 (INS:INS) are clear haploid inducers and that the plants that are HD99 at the marker GRMZM2G471240_14 (DEL:DEL) are not haploid inducers.

Example 2

Comparison of the GRMZM2G471240 Alleles

Sequencing of GRMZM2G471240 Alleles

The genomic sequence of the GRMZM2G471240 candidate gene in genotype PK6 was determined by PCR amplification of overlapping fragments from reference sequence B73, which were arbitrarily named A, C and D, with primers G471240_A_F and G471240_A_R (sequences SEQ ID No 10 and SEQ ID No 11), G471240_C_F and G471240_C_R (sequences SEQ ID No 12 and SEQ ID No 13), and G471240_D_F and G471240_D_R3 (or G471240_B_R), respectively of sequences SEQ ID No 14, SEQ ID No 15 and SEQ ID No 16 (see Table 9 for primer sequences). PCR fragments obtained with a proof reading enzyme were either sequenced directly or after prior subcloning (SEQ ID No 1). The genomic sequence of the GRMZM2G471240 candidate gene in genotype HD99 was determined by PCR amplification of overlapping fragments, which were arbitrarily named A, C and B with primers G471240_A_F and G471240_A_R, G471240_C_F and G471240_C_R and G471240_B_F and G471240_B_R, respectively sequences SEQ ID No 10, SEQ ID No 11, SEQ ID No 12, SEQ ID No 13, SEQ ID No 17 and SEQ ID No 16 (see Table 9 for primer sequences). PCR fragments obtained with a proof reading enzyme were either sequenced directly or after prior subcloning (SEQ ID No 2). An extraction of the corresponding region from the reference genome of genotype B73 (Schnable et al., 2009) is also presented in the sequence listing (SEQ ID No 23).

Sequence Alignment of Alleles at the GRMZM2G471240 Locus

Alignment with the reference sequence of genotype B73 (SEQ ID No 23) revealed numerous polymorphisms between PK6, HD99 and B73. Among them was a 4 bp insertion in exon 4 of the GRMZM2G471240 candidate gene in genotype PK 6 (FIG. 2). The consequence of the 4 bp insertion in exon 4 is a frame shift leading to 20 non conserved amino acids followed by a premature STOP codon (SEQ ID No 24). This may be the causal mutation explaining the PK6 phenotype (FIG. 3). GRMZM2G471240 is predicted to code for a phospholipase (PL) and will be named ZmPL for the further experimental genetic constructs. T01 and T02 correspond to alternative gene models proposed by the annotation of the B73 reference sequence, which differ in the length of exon 2 (SEQ ID No 26, SEQ ID No 27; see FIG. 1). All cDNA products cloned from pollen of genotypes PK6 and HD99 correspond to gene model T01.

Subcellular Localization of the ZmPL Protein

The subcellular localization of the ZmPL protein from genotypes PK6 and HD99 was determined in a heterologous system by in frame fusions to citrine fluorescent protein, stable transformation of *Arabidopsis thaliana* and observation of transgenic root tips by confocal microscopy. Based on the fluorescence of the chimeric proteins the wildtype $ZmPL_{HD99}$ protein was mainly located in the cytoplasmic membrane but also present in the cytoplasm, whereas the truncated $ZmPL_{PK6}$ protein was absent from the cytoplasmic membrane and almost entirely located in the cytoplasm (FIG. 15). This difference may be caused either by the loss of the 49 C-terminal amino acid residues in the $ZmPL_{PK6}$ protein or the presence of the 20 unrelated amino acid residues These results suggest that (i) the 3' end of the protein is important for its localization in the cytoplasmic membrane and (ii) that the mis-localization of the $ZmPL_{PK6}$ protein is the cause for the haploid inducing capacity of genotype PK6.

Materials and Methods: *Arabidopsis* ecotype Col-0 was transformed with the floral-dip method (Clough and Bent, 1998) and a modified procedure for *Agrobacterium* preparation (Logemann et al., 2006); ZmPL CDS (without STOP codon) from HD99 and PK6 were PCR amplified from cDNA made from mature anther tissues using respectively primers pair PL-CDS-F_Dtopo corresponding to SEQ ID No 52/PL-CDS-HD99-R2 corresponding to SEQ ID No 53 and PL-CDS-F_Dtopo/PL-CDS-PK6-R2 corresponding to SEQ ID No 54, and cloned into pENTR/D-topo (Invitrogen). The cassettes pUBQ10::ZmPL-CDS::CITRINE were obtained by LR reaction between the fragments pUBQ10, ZmPL CDS, mCITRINE and the destination vector pK7m34GW (Karimi et al., 2005). The fragments for pUBQ10 and mCITRINE were gifts of Yvon Jallais (Jaillais et al., 2011) plasmid L1540 (pUBQ10::CDS-$ZmPL_{HD99}$::Citrine) is described in FIG. 16 and plasmid L1541 (pUBQ10::CDS-$ZmPL_{PK6}$::Citrine) in FIG. 17.

Fluorescence was detected with a Zeiss LSM 710 Laser Scanning Microscope: mCITRINE was excited with a 510-nm laser signal and fluorescence was detected using 520-580 nm bandpass filters. Image data were analyzed by using Image J software.

Example 3

Creation of New Inducer Alleles by Transgenesis

Transformation Protocol

The plasmids used for the production of $ZmPL_{PK6}$-OE, $ZmPL_{HD99}$-OE and $ZmPL_{A188}$-RNAi plants contained the backbone of vector pSB11 (Ishida et al., 1996), a Basta resistance cassette (*Oryza sativa* (rice) Actin promoter and intron, Bar gene and Nos terminator) next to the right border, a GFP cassette (CsVMV promoter and FAD2 intron, GFP gene and Nos terminator) and either the ZmPL coding sequence (primers see Table 9) under the control of the constitutive rice Actin promoter and intron, or a unique gene fragment (primers see Table 9) separated by the rice Tubulin intron in hairpin configuration and followed by the AtSac66 terminator. *Agrobacterium*-mediated transformation of maize inbred line A188 was executed according to a published protocol (Ishida et al., 2007). For each transformation event the number of T-DNA insertions was evaluated by qPCR, and the integrity of the transgene was verified by PCR with primers situated in the AtSac66 terminator near the end of the construct of interest next to the left border.

Inhibition of the PL Gene by RNAi (L1465) $ZmPL_{A188}$-RNAi

The gene encoded by gene model GRMZM2G471240 was named PL (phospholipase) and the respective genotype indicated by an extension in subscript.

The $PL_{A188}$-RNAi construct tests whether (i) the inducing capacity of genotype PK6 was linked to a loss-of-function of the PL gene and whether a (ii) a knockdown of the PL gene could yield a stronger phenotype or other phenotypes than the 4 bp insertion in the PK6 allele.

For the RNAi construct primers G471240-attB1 and G471240-attB2 of SEQ ID No 18 and SEQ ID No 19 (see Table 9) were used to amplify an intronless fragment of 363 bp in exon 4 on genomic DNA of genotype A188, the genotype used for maize transformation. Contrary to the beginning of the PL gene, the chosen fragment shared no sequence homology with the related pseudogene GRMZM2G062313. The fragment was recombined (BP Gateway reaction) into the vector pDONR221 (Invitrogen) to yield the entry clone L1457 (FIG. 7).

Subsequently the fragment was recombined (LR Gateway reaction) into the vector pBIOS 898 (gift of W. Paul, Biogemma). The resulting plasmid L1465 was used for maize transformation (FIG. 8). Transgenic plants have been tested for their capacity to induce gynogenesis and (ii) examined for other phenotypes linked to pollen maturation and fertilisation.

The lines to be tested for haploid induction were crossed as male parent with hybrid F564×DH7 homozygous for the glossy1 mutation. A minimum of 100 kernels was germinated and scored for the glossy (bright leaf surface, adhering water droplets) phenotype indicative of haploid plantlets. Haploid induction rate was determined as the percentage of glossy plantlets among germinated plantlets.

Hemizygous transgenic lines were either selfed or crossed with the glossy tester. At least 50 kernels were sown and sprayed with Basta herbicide (glufosinate-ammonium solution at 1.5 g/L) 10 days after germination. Segregation distortion was determined as the number of Basta resistant transgenic plantlets divided by the number of wild-type plantlets.

For five independent transformation events (U261 to U265) fertile plants with offspring were obtained. Event U265 provoked some haploid induction both using a heterozygous T1 plant (1 haploid plantlet among 197 T2 seedlings) and a homozygous T2 plant (1 haploid plantlet among 1000 T3 seedlings). It needs to be recalled that other loci than ggi1 influence haploid induction rate and that the genotype A188 used for maize transformation has an extremely low haploid induction rate (0 haploid plantlets among over 3000 seedlings tested) compared to other genotypes. Finally, event U264 showed a strong segregation bias (8.3% and 3.6% instead of the 50% transgenics expected) both in T1 and T2 seedlings and some haploid induction (1 haploid plantlet among 1177 T2 seedlings). All results for event U264 are based on heterozygous plants, since so far no confirmed homozygous plants have been obtained for this event.

Ectopic Over Expression (OE) of the $PL_{PK6}$ Allele (L1482)

For the $PL_{PK6}$-OE construct genomic DNA containing the entire coding sequence of genotype PK6 was amplified with primers PLPK6_HDPK_F1 and PLPK6_PK6_R1, of sequences SEQ ID No 20 and SEQ ID No 21 (see Table 9). The PCR product was recombined (BP Gateway reaction) into the vector pDONR221 (Invitrogen) to yield the entry clone L1478 (FIG. 9). In this intermediary vector the coding sequence (CDS) of $PL_{PK6}$ is flanked by attL sites (CDS is the genomic sequence from Start to Stop codon). Subsequently the CDS of $PL_{PK6}$ was recombined (LR Gateway reaction) into the vector pBIOS 895 (gift of W. Paul, Biogemma). The resulting plasmid L1482, in which the $PL_{PK6}$ CDS is placed under the control of a rice Actin promoter and followed by a AtSac66 terminator, was used for maize transformation (FIG. 10). Transgenic plants have been tested for their capacity to induce gynogenesis and (ii) examined for other phenotypes linked to pollen maturation and fertilisation.

The lines to be tested for haploid induction were crossed as male parent with hybrid F564×DH7 homozygous for the glossy1 mutation. A minimum of 100 kernels was germinated and scored for the glossy (bright leaf surface, adhering water droplets) phenotype indicative of haploid plantlets. Haploid induction rate was determined as the percentage of glossy plantlets among germinated plantlets.

Hemizygous transgenic lines were either selfed or crossed with the glossy tester. At least 50 kernels were sown and sprayed with Basta herbicide (glufosinate-ammonium solution at 1.5 g/L) 10 days after germination. Segregation distortion was determined as the number of Basta resistant transgenic plantlets divided by the number of wild-type plantlets.

Ectopic Over Expression of the $PL_{HD99}$ Allele (L1483), Complementation of PK6 Allele In genotype PK6 a 4 bp insertion in the PL gene causes a truncation of the predicted protein. If this truncated protein was not functional at all, then the introduction of the non-inducing wild type allele $PL_{HD99}$ should complement the mutation and block the induction of gynogenesis.

For the $PL_{HD99}$-OE construct genomic DNA containing the entire coding sequence of genotype HD99 was amplified with primers PLPK6_HDPK_F1 and PLPK6_HD99_R1 of sequences SEQ ID No 20 and SEQ ID No 22 (Table 9). The PCR product was recombined (BP Gateway reaction) into the vector pDONR221 (Invitrogen) to yield the entry clone L1479 (FIG. 11). In this intermediary vector the CDS (genomic sequence from Start to Stop codon) of $PL_{HD99}$ is flanked by attL sites.

Subsequently the CDS of $PL_{HD99}$ was recombined (LR Gateway reaction) into the vector pBIOS 895 (gift of W. Paul, Biogemma). The resulting plasmid L1483, in which the $PL_{HD99}$ CDS is placed under the control of a rice Actin promoter and followed by a AtSac66 terminator, was used for maize transformation (FIG. 12). Transgenic plants have been crossed with genotype PK6 and offspring have been tested for their capacity to induce gynogenesis.

The lines to be tested for haploid induction were crossed as male parent with hybrid F564×DH7 homozygous for the glossy1 mutation. A minimum of 100 kernels was germinated and scored for the glossy (bright leaf surface, adhering water droplets) phenotype indicative of haploid plantlets. Haploid induction rate was determined as the percentage of glossy plantlets among germinated plantlets.

Hemizygous transgenic lines were either selfed or crossed with the glossy tester. At least 50 kernels were sown and sprayed with Basta herbicide (glufosinate-ammonium solution at 1.5 g/L) 10 days after germination. Segregation distortion was determined as the number of Basta resistant transgenic plantlets divided by the number of wild-type plantlets.

Example 4

Creation of Mew Inducer Alleles by Targeted Transgenesis Mutation of the $PL_{A188}$ Allele The CAS9/CRISPR system allows to create small deletions at nearly any site in the genome. The system have been used to create two distinct deletions: one at the beginning of the gene to obtain a true knockout (as compared to the knockdown by RNAi) and a second one to obtain an independent frameshift towards the end of the gene copying the 4 bp insertion in the $PL_{PK6}$ allele. TALEN system has also been used to create new mutants (Gaj et al., 2013).

Example 5

Use of GRMZM2G471240_14 Marker for Control Quality of Seed Lots.

Four seed stocks for inducer hybrids (RWS×RWK76) and five for inducer lines (RWS or RWK76) from different years and seasons of production have been tested for seed purity at the locus of PL gene, about 350 kernel by lot have been randomly selected from each lot, and tested with the GRMZM2G471240_14 marker by the KASP method (with the three primers of the following sequences: SEQ ID No 43: GAGGGCATCGGCATTGCTTCCTT (Common); SEQ ID No 44: GTCAACGTGGAGACAGGGAGC and SEQ ID No 45: GTCAACGTGGAGACAGGGAGG). The results are shown in Table 7 below.

TABLE 7

| | wt means wild type and NA reflects missing data | | | | | | | | |
|---|---|---|---|---|---|---|---|---|---|
| | RWS × RWK76 | RWS × RWK76 | RWS × RWK76 | RWS × RWK76 | RWS | RWS | RWK76 | RWK76 | RWK76 |
| Lot reference | 2010 winter | 2010 summer | 2012 winter | 2012 summer | 2011 summer | 2012 summer | 2012 winter | 2012 summer | 2013 winter |
| Number of tested kernels | 344 | 354 | 372 | 372 | 305 | 372 | 372 | 372 | 369 |
| wt:wt (Homozygous wt) | 9 | 10 | 0 | 0 | 0 | 0 | 0 | 0 | 0 |
| pk6:wt (Heterozygous pk6/wt) | 50 | 56 | 1 | 4 | 0 | 0 | 0 | 0 | 0 |

TABLE 7-continued wt means wild type and NA reflects missing data

|  | RWS × RWK76 | RWS × RWK76 | RWS × RWK76 | RWS × RWK76 | RWS | RWS | RWK76 | RWK76 | RWK76 |
|---|---|---|---|---|---|---|---|---|---|
| pk6:pk6 (homozygous for pk6) | 284 | 282 | 371 | 368 | 305 | 368 | 367 | 368 | 360 |
| NA | 1 | 6 | 0 | 0 | 0 | 4 | 5 | 4 | 9 |

According to these results the two first lots show an insufficient purity to be further used to induce haploids. These findings corroborate the low induction rate of these lots that was below 5% when the normal rate is about 10%. Moreover the more recent lots can be used for inducing new haploid lines.

This molecular test can be done on each kernel individually, but also on a pool of kernel samples obtained by a puncher according to the method described in the patent application FR No. 1450486.

The method currently used for purity control is based on the sowing of these seeds, crossing of each plant with a female to test inducer ability, and sowing of seed obtained from this cross to identify haploid and diploids plants. The phenotypic markers ligule-less or glossy (Lashermes and Beckert 1988, Neuffer, 1997) are currently used for this last test. With the new method according to the invention, the time needed to obtain information on quality control of the lot is drastically reduced and thanks to the number of seeds that can be investigated the accuracy of the results is much higher.

Example 6

Identification of a Zm PL Orthologues
Analysis of the deduced amino acid sequences of the wild-type ZmPL$_{b73}$ protein corresponding to SEQ ID No 26, revealed the presence of two S-palmitoylation sites at position 10 and position 423 as well as an S-farnesylation site at position 423 (Table 8a).

The second site (423) is missing in the truncated ZmPL$_{PK6}$ protein. Together with the fact that the truncated ZmPL$_{PK6}$ protein is no longer localized in the cytoplasmis membrane, this suggests that the presence of a lipid anchor at the C-terminus of ZmPL may be essential for the correct subcellular localization of the protein.

A survey of the deduced amino acids from cereal orthologues showed that the proteins from *Brachypodium dystachion* (SEQ ID 29), *Sorghum bicolor* (SEQ ID 30), *Panicum virgatum* (SEQ ID 31 and SEQ ID 32), *Setaria italica* (SEQ ID 33) and *Oryza sativa* (SEQ ID 34) are all predicted to have lipid anchors at their N-terminus and C-terminus, whereas for *Hordeum vulgare* (SEQ ID 28) only a N-terminal lipid anchor was predicted. The data suggest that the presence of an N-terminal and a C-terminal lipid anchor by S-palmitoylation, S-farnesylation and/or S-geranylgeranylation may be necessary for subcellular localization in the cytoplasmic membrane (Tables 8b to 8h)

The presence of an N-terminal and C-terminal membrane anchor may be a useful additional criterion for the identification of functional orthologues in non-cereals, where phylogenetic analysis, even combined with the criterion of expression in the pollen, is often not sufficient.

Materials and Methods: For the prediction of lipid anchors allowing membrane association, the "GPS-lipid" web site predictor (http://lipid.biocuckoo.org/webserver.php) was used with the following parameters: "Search for palmitoylation, N-myristoylation, farnesylation geranylgeranylation post-translational modifications" and threshold setting "High".

TABLE 8a

| ID | Position | Peptide | Score | Cutoff | Type |
|---|---|---|---|---|---|
| SEQ ID No 26 | 10 | SYSSRRPCNTCSTKA | 3.817 | 3.076 | S-Palmitoylation: Cluster B |
| SEQ ID No 26 | 423 | INPRGSRCASYDI** | 5.806 | 1.983 | S-Palmitoylation: Cluster A |
| SEQ ID No 26 | 423 | INPRGSRCASYDI** | 12.801 | 4.003 | S-Farnesylation: Non-consensus |

TABLE 8b

| ID | Position | Peptide | Score | Cutoff | Type |
|---|---|---|---|---|---|
| SEQ ID No 30 | 11 | YYSSRRPCNACSTKA | 4.969 | 3.076 | S-Palmitoylation: Cluster B |
| SEQ ID No 30 | 14 | SRRPCNACSTKAMAG | 3.224 | 3.076 | S-Palmitoylation: Cluster B |
| SEQ ID No 30 | 141 | KPRYNGKCLRNLIMS | 2.223 | 1.983 | S-Palmitoylation: Cluster A |
| SEQ ID No 30 | 430 | GGASRRTCASKVSNV | 6.338 | 4.003 | S-Farnesylation: Non-consensus |

TABLE 8b-continued

| ID | Position | Peptide | Score | Cutoff | Type |
|---|---|---|---|---|---|
| SEQ ID No 30 | 430 | GGASRRTCASKVSNV | 6.329 | 1.617 | S-Geranylgeranylation: Non-consensus |

TABLE 8c

| ID | Position | Peptide | Score | Cutoff | Type |
|---|---|---|---|---|---|
| SEQ ID No 33 | 10 | SYSSRRPCNACRTKA | 4.493 | 3.076 | S-Palmitoylation: Cluster B |
| SEQ ID No 33 | 13 | SRRPCNACRTKAMAG | 1.979 | 1.396 | S-Palmitoylation: Cluster C |
| SEQ ID No 33 | 415 | ACAGGSRCCSPVKT* | 3.977 | 1.983 | S-Palmitoylation: Cluster A |
| SEQ ID No 33 | 415 | ACAGGSRCCSPVKT* | 8.327 | 4.003 | S-Farnesylation: Non-consensus |
| SEQ ID No 33 | 415 | ACAGGSRCCSPVKT* | 1.112 | 0.486 | S-Geranylgeranylation: CC/CXC |
| SEQ ID No 33 | 416 | CAGGSRCCSPVKT** | 20.687 | 4.003 | S-Farnesylation: Non-consensus |
| SEQ ID No 33 | 416 | CAGGSRCCSPVKT** | 4.008 | 0.486 | S-Geranylgeranylation: CC/CXC |

TABLE 8d

| ID | Position | Peptide | Score | Cutoff | Type |
|---|---|---|---|---|---|
| SEQ ID No 31 | 10 | SYSSRRPCSVCRTKA | 4.212 | 3.076 | S-Palmitoylation: Cluster B |
| SEQ ID No 31 | 13 | SRRPCSVCRTKAMAG | 3.754 | 3.076 | S-Palmitoylation: Cluster B |
| SEQ ID No 31 | 422 | GAAGGSRCCSPVKLY | 3.323 | 1.983 | S-Palmitoylation: Cluster A |
| SEQ ID No 31 | 422 | GAAGGSRCCSPVKLY | 5.441 | 4.003 | S-Farnesylation: Non-consensus |
| SEQ ID No 31 | 422 | GAAGGSRCCSPVKLY | 4.063 | 0.486 | S-Geranylgeranylation: CC/CXC |
| SEQ ID No 31 | 423 | AAGGSRCCSPVKLY* | 21.309 | 4.003 | S-Farnesylation: Non-consensus |
| SEQ ID No 31 | 423 | AAGGSRCCSPVKLY* | 4.572 | 0.486 | S-Geranylgeranylation: CC/CXC |

TABLE 8e

| ID | Position | Peptide | Score | Cutoff | Type |
|---|---|---|---|---|---|
| SEQ ID No 32 | 10 | SYSSRRPCSVCRTKA | 4.212 | 3.076 | S-Palmitoylation: Cluster B |
| SEQ ID No 32 | 13 | SRRPCSVCRTKAMAR | 3.82 | 3.076 | S-Palmitoylation: Cluster B |
| SEQ ID No 32 | 422 | GCAGGSTCCSPVKT* | 4.031 | 1.983 | S-Palmitoylation: Cluster A |
| SEQ ID No 32 | 422 | GCAGGSTCCSPVKT* | 8.189 | 4.003 | S-Farnesylation: Non-consensus |

TABLE 8e-continued

| ID | Position | Peptide | Score | Cutoff | Type |
|---|---|---|---|---|---|
| SEQ ID No 32 | 422 | GCAGGSTCCSPVKT* | 2.906 | 0.486 | S-Geranylgeranylation: CC/CXC |
| SEQ ID No 32 | 423 | CAGGSTCCSPVKT** | 19.819 | 4.003 | S-Farnesylation: Non-consensus |
| SEQ ID No 32 | 423 | CAGGSTCCSPVKT** | 4.822 | 0.486 | S-Geranylgeranylation: CC/CXC |

TABLE 8f

| ID | Position | Peptide | Score | Cutoff | Type |
|---|---|---|---|---|---|
| SEQ ID No 29 | 6 | **MASYACRRPCESC | 1.559 | 1.396 | S-Palmitoylation: Cluster C |
| SEQ ID No 29 | 10 | SYACRRPCESCRTRA | 1.793 | 1.396 | S-Palmitoylation: Cluster C |
| SEQ ID No 29 | 13 | CRRPCESCRTRAMAG | 1.727 | 1.396 | S-Palmitoylation: Cluster C |
| SEQ ID No 29 | 423 | PANGKSRC******* | 10.896 | 4.003 | S-Farnesylation: Non-consensus |
| SEQ ID No 29 | 423 | PANGKSRC******* | 4.688 | 1.617 | S-Geranylgeranylation: Non-consensus |

TABLE 8g

| ID | Position | Peptide | Score | Cutoff | Type |
|---|---|---|---|---|---|
| SEQ ID No 34 | 7 | *MAASYSCRRTCEAC | 1.542 | 1.396 | S-Palmitoylation: Cluster C |
| SEQ ID No 34 | 11 | SYSCRRTCEACSTRA | 7.03 | 3.076 | S-Palmitoylation: Cluster B |
| SEQ ID No 34 | 197 | NALLSDICISTSAAP | 3.092 | 3.076 | S-Palmitoylation: Cluster B |
| SEQ ID No 34 | 430 | GEPSGVACKR***** | 8.222 | 4.003 | S-Farnesylation: Non-consensus |

TABLE 8h

| ID | Position | Peptide | Score | Cutoff | Type |
|---|---|---|---|---|---|
| SEQ ID No 28 | 6 | **MASYWCRRPCESC | 1.698 | 1.396 | S-Palmitoylation: Cluster C |
| SEQ ID No 28 | 10 | SYWCRRPCESCSTRA | 6.059 | 3.076 | S-Palmitoylation: Cluster B |
| SEQ ID No 28 | 13 | CRRPCESCSTRAMAG | 1.855 | 1.396 | S-Palmitoylation: Cluster C |
| SEQ ID No 28 | 195 | NARLADICIGTSAAP | 3.494 | 3.076 | S-Palmitoylation: Cluster B |

Example 7

Identification of a ZmPL Functional Orthologue from *Arabidopsis thaliana*.

To identify the functional ortholog of ZmPL in the genome of the model plant *Arabidopsis thaliana* a phylogenetic tree of all patatin-like phospholipases was constructed. Using preferential expression in pollen and the prediction of an N-terminal and a C-terminal lipid anchor as additional criteria, the gene At1g61850.1 was identified as the best candidate. The mutants N642695, N657713 and N596745 (obtained from NASC), which were in a Col-0 wildtype background, were crossed as male parent to a glabra1 mutant line.

TABLE 9 primers identification

| SEQ ID name | Primer name | Primer sequence (5' to 3') | Primer use |
|---|---|---|---|
| 18 | G471240-attB1 | GGGGACAAGTTTGTACAAAAAAGCAGGCTTTCGACGTCCGAGCAGGGCC | RNAi fragment |
| 19 | G471240-attB2 | GGGGACCACTTTGTACAAGAAAGCTGGGTTCACCGAGGGCATCGGCATTGCTTCC | RNAi fragment |
| 20 | PLPK6_HDPK_F1 | GGGGACAAGTTTGTACAAAAAAGCAGGCTTAGGCAATGGCGAGCTACTC | $PL_{PK6}$-OE, $PL_{HD99}$-OE and $PL_{HD99}$-fusion |
| 21 | PLPK6_PK6_R1 | GGGGACCACTTTGTACAAGAAAGCTGGGTAGCCTTGTTCTCCTCTCCT | $PL_{PK6}$-OE |
| 22 | PLPK6_HD99_R1 | GGGGACCACTTTGTACAAGAAAGCTGGGTAGCCACTTGTCTTAGATAT | $PL_{HD99}$-OE |
| 6 | Pat_qRT_F1 | GAGAAGGAAGCAATGCCGATGCC | qRT-PCR |
| 7 | Pat_qRT_R1 | TGATTGACAGTAAAGCCACTTGTCTTAGATATC | qRT-PCR |
| 8 | actin-q-F | TACCCGATTGAGCATGGCA | qRT-PCR |
| 9 | actin-q-R | TCTTCAGGCGAAACACGGA | qRT-PCR |
| 10 | G471240_A_F | AGTTCATCACTAATCACACTTATTGTGCC | allelic sequencing |
| 11 | G471240_A_R | GGCGGACGTGCCAATGCA | allelic sequencing |
| 17 | G471240_B_F | GAACGCTCTGCTCTCGGACG | allelic sequencing |
| 16 | G471240_B_R | TATATTCAAGAACATATA | allelic sequencing |
| 12 | G471240_C_F | ATGTCCGCGCTGAGGAAGCCA | allelic sequencing |
| 13 | G471240_C_R | GAGCACTGCCGCGCCGTGTA | allelic sequencing |
| 14 | G471240_D_F | GGAGCTGTACCCAGTGAAGCCG | allelic sequencing |
| 15 | G471240_D_R3 | TTAGATATCGTACGACGCACATCTAGA | allelic sequencing |
| 46 | attB4_prom_PL_2576_B73 | GGGGACAACTTTGTATAGAAAAGTTGCTTCAAAATGGTTATGCGTAGGTTGAA | |
| 47 | attB1r_prom_PL_2576_B73 | GGGGACTGCTTTTTTGTACAAACTTGCTGCCGCCTTCGACAACAC | |
| 48 | attB4_promoPL_2534_PK6 | GGGGACAACTTTGTATAGAAAAGTTGCTTTTAGGATAAGCCAGAGTTTGT | |
| 49 | attB1r_promoPL_2534_PK6 | GGGGACTGCTTTTTTGTACAAACTTGCTGCCGCCTTCGACCGCAC | |
| 52 | PL-CDS-F_Dtopo | CACCATGGCGAGCTACTCGTCGCGGCGT | |
| 53 | PL-CDS-HD99-R2 | GATATCGTACGACGCACATCTAGAG | |
| 54 | PL-CDS-PK6-R2 | GCGAGCCCACCGAGGGCAT | |

REFERENCES

Eyal, Y., Curie, C., and McCormick, S. (1995). Pollen specificity elements reside in 30 bp of the proximal promoters of two pollen-expressed genes. Plant Cell 7, 373-384;

Barret P; Brinkmann M; Beckert M., (2008) A major locus expressed in the male gametophyte with incomplete penetrance is responsible for in situ gynogenesis in maize, *Theoretical and Applied Genetics*, 117(4): 581-594;

Bordes J., Création de lignées haploïdes doublées de maës par gynogenèse induite in situ: amélioration de la méthode et intégration dans les schémnas de sélection. Thèse, 2006;

Chia J M, Song C, Bradbury P J, Costich D, de Leon N, Doebley J, Elshire R J, Gaut B, Geller L, Glaubitz J C, Gore M, Guill K E, Holland J, Hufford M B, Lai J, Li M, Liu X, Lu Y, McCombie R, Nelson R, Poland J, Prasanna B M, Pyhäjärvi T, Rong T, Sekhon R S, Sun Q, Tenaillon M I, Tian F, Wang J, Xu X, Zhang Z, Kaeppler S M, Ross-Ibarra J, McMullen M D, Buckler E S, Zhang G, Xu Y, Ware D., Maize HapMap2 identifies extant variation from a genome in flux. Nat Genet. 2012 Jun. 3;44(7): 803-7;

Clough, S. J., and Bent, A. F. (1998). Floral dip: a simplified method for *Agrobacterium*mediated transformation of *Arabidopsis thaliana*. Plant J 16: 735-743.-Coe 1959. A line of maize with high haploid frequency. The American Naturalist, November-december 1959, p381;

Deimling S, Röber F K, Geiger H H, (1997), Methodology and genetics of in vivo haploid induction in maize [in German]. Vortr Pflanzenz üchtg, 38: 203-224;

Dong X; Xu X; Miao J; LI L; Zhang D; Mi X; Liu C; Tian X; Melchinger A E; Chen S., (2013) Fine mapping of qhir1 influencing in vivo haploid induction in maize. *Theoretical And Applied Genetics*, 126(7): 1713-1720;

Gaj T., Gersbach C. A., and C. F. Barbas, ZFN, TALEN, and CRISPR/Cas-based methods for genome engineering. Trends in Biotechnology, July 2013, Vol. 31, No. 7;

Geiger H H; Gordillo G A., (2009) Doubled Haploids In Hybrid Maize Breeding, *Maydica*, 54(4): 485-499;

Greenblatt I M; Bock M., A commercially desirable procedure for detection of monoploids in maize. JOURNAL OF HEREDITY, 58: 9-13;

Ishida, Y., Saito, H., Ohta, S., Hiei, Y., Komari, T., and Kumashiro, T. (1996). High efficiency transformation of maize (*Zea mays* L) mediated by *Agrobacterium tumefaciens*. Nat. Biotechnol., 14, 745-750;

Ishida, Y., Hiei, Y., and Komari, T., (2007). *Agrobacterium*-mediated transformation of maize. Nat Protoc 2, 1614-1621;

Jaillais, Y., Hothorn, M., Belkhadir, Y., Dabi, T., Nimchuk, Z. L., Meyerowitz, E. M., and Chory, J., (2011). Tyrosine phosphorylation controls brassinosteroid receptor activation by triggering membrane release of its kinase inhibitor. Genes Dev., 25, 232-237;

Karimi, M., Bleys, A., Vanderhaeghen, R., and Hilson, P., (2007). Building blocks for plant gene assembly. Plant Physiol., 145, 1183-1191;

Lashermes P; Beckert M., Genetic Control Of Maternal Haploidy In Maize (*Zea Maysl.*) And Selection Of Haploid Inducing Lines. *Theoritical And Applied Genetics*, 76(3): 405-410;

Li, P., Ponnala, L., Gandotra, N., Wang, L., Si, Y., Tausta, S. L., Kebrom, T. H., - Provart, N., Patel, R., Myers, C. R., Reidel, E. J., Turgeon, R., Liu, P., Sun, Q., Nelson T. & T. P. Brutnell. The developmental dynamics of the maize leaf transcriptome, NATURE GENETICS, 2010, 42(12): 10p.;

Logemann, E., Birkenbihl, R. P., Ulker, B., and Somssich, I. E. (2006). An improved method for preparing *Agrobacterium* cells that simplifies the *Arabidopsis* transformation protocol. Plant Methods 2: 16.

Needleman and Wunsch, 1970 A general method applicable to the search for similarities in the amino acid sequence of two proteins. J. Mol. Biol. 48:443-453

Neuffer M G; Coe E H; Wessler S R. *Mutants of maize*; Neuffer M G; Coe E H; Wessler E R SR-1997-Vol: 468p;

Prigge V; Sanchez C; Dhillon B S; Schipprack W; Araus J L; Banziger M; Melchinger A E., (2012) Doubled Haploids in Tropical Maize: I. Effects of Inducers and Source Germplasm on in vivo Haploid Induction Rates., *Crop Science*, 51(4): 1498-1506;

Prigge V; Xu X W; Li L; Babu R; Chen S J; Atlin G N; Melchinger A E. (2011) New insights into the genetics of in vivo induction of maternal haploids, the backbone of doubled haploid technology in maize. *Genetics*, 190(2): 781-793;

Rober F K; Gordillo G A; Geiger H H., (2005) In vivo haploid induction in maize—Performance of new inducers and significance of doubled haploid lines in hybrid breeding. *Maydica*, 50(3-4): 275-283;

Schnable, P. S., Ware, D., Fulton, R. S., Stein, J. C., Wei, F., Pasternak, S., Liang, C., Zhang, J., Fulton, L., Graves, T. A., et al., (2009). The B73 maize genome: complexity, diversity, and dynamics. Science 326, 1112-1115;

Sekhon, R. S., Lin, H., Childs, K. L., Hansey, C. N., Buell, C. R., de Leon, N., and Kaeppler, S. M. (2011)., Genome-wide atlas of transcription during maize development. Plant J. Cell Mol. Biol., 66, 553-563;

Weber D F., (2014) Today's Use of Haploids in Corn Plant Breeding Advances In Agronomy, 123: 123-144;

Winter D., Vinegar B., Nahal. H., Ammar R., Wilson G. V., and N. J. Provar. An "Electronic Fluorescent Pictograph" Browser for Exploring and Analyzing Large-Scale Biological Data Sets. 2007, PLoS One 2(8):e718;

Xu X W; Li L; Dong X; Jin W W; Melchniger A E; Chen S J., (2013) Gametophytic and zygotic selection leads to segregation distortion through in vivo induction of a maternal haploid in maize. Journal Of Experimental Botany, 64(4): 1083-1096.

The invention claimed is:

1. A process for isolating a mutant haploid inducer sequence in a plant other than maize comprising:
   (1) determining the presence in a plant population of a sequence that is orthologous to:
   (a) a polynucleotide comprising or consisting of SEQ ID NO: or
   (b) a polypeptide encoded by the polynucleotide of (a);
   and selecting said sequence as an orthologous sequence if it codes for a polypeptide which is expressed in pollen or a pollen tube of the plant, and which comprises a lipid anchor domain in its C-terminal and N-terminal polypeptide sequence;

(2a) screening a mutant plant population, other than maize, to identify a mutant haploid inducer of the orthologous sequence determined in (1); or (2b) generating a mutant, haploid inducer, of the orthologous sequence selected in (1) by using a gene editing method, wherein said mutant haploid inducer of the orthologous sequence codes for a polypeptide which does not comprise a lipid anchor domain in its C-terminal polypeptide sequence; and (3) isolating said mutant haploid inducer sequence.

2. The process according to claim 1, wherein the orthologous sequence identified in (2a) is a fragment.

3. A plant other than maize having a mutant haploid inducer sequence isolated by the method according to claim 1.

4. The process according to claim 1, wherein the plant other than maize is not a cereal.

* * * * *

UNITED STATES PATENT AND TRADEMARK OFFICE
CERTIFICATE OF CORRECTION

PATENT NO. : 11,445,671 B2
APPLICATION NO. : 15/572110
DATED : September 20, 2022
INVENTOR(S) : Martinant et al.

It is certified that error appears in the above-identified patent and that said Letters Patent is hereby corrected as shown below:

In the Claims

Columns 95, 96 and 97, Claim 1, please change:
"1. A process for isolating a mutant haploid inducer sequence in a plant other than maize comprising:
    (1) determining the presence in a plant population of a sequence that is orthologous to :
        (a) a polynucleotide comprising or consisting of SEQ ID NO: ; or
        (b) a polypeptide encoded by the polynucleotide of (a);
    and selecting said sequence as an orthologous sequence if it codes for a polypeptide which is expressed in pollen or a pollen tube of the plant, and which comprises a lipid anchor domain in its C-terminal and N-terminal polypeptide sequence;
    (2a) screening a mutant plant population, other than maize, to identify a mutant haploid inducer of the orthologous sequence determined in (1); or
    (2b) generating a mutant, haploid inducer, of the orthologous sequence selected in (1) by using a gene editing method, wherein said mutant haploid inducer of the orthologous sequence codes for a polypeptide which does not comprise a lipid anchor domain in its C-terminal polypeptide sequence; and
    (3) isolating said mutant haploid inducer sequence."

To:
-1. A process for isolating a mutant haploid inducer sequence in a plant other than maize comprising:
    (1) determining the presence in a plant population of a sequence that is orthologous to :
        (a) a polynucleotide comprising or consisting of SEQ ID NO: 4; or
        (b) a polypeptide encoded by the polynucleotide of (a);
    and selecting said sequence as an orthologous sequence if it codes for a polypeptide which is expressed in pollen or a pollen tube of the plant, and which comprises a lipid anchor domain in its C-terminal and N-terminal polypeptide sequence;

Signed and Sealed this
Thirteenth Day of February, 2024

Katherine Kelly Vidal
*Director of the United States Patent and Trademark Office*

(2a) screening a mutant plant population, other than maize, to identify a mutant haploid inducer of the orthologous sequence determined in (1); or (2b) generating a mutant, haploid inducer, of the orthologous sequence selected in (1) by using a gene editing method, wherein said mutant haploid inducer of the orthologous sequence codes for a polypeptide which does not comprise a lipid anchor domain in its C-terminal polypeptide sequence; and (3) isolating said mutant haploid inducer sequence.-